(12) United States Patent
Feda

(10) Patent No.: US 7,639,784 B2
(45) Date of Patent: Dec. 29, 2009

(54) SYSTEMS AND METHODS FOR CONTROLLING AN X-RAY SOURCE

(76) Inventor: Francis Michael Feda, 14 Woodmere Dr., Sudbury, MA (US) 01776

(*) Notice: Subject to any disclaimer, the term of this patent is extended or adjusted under 35 U.S.C. 154(b) by 22 days.

(21) Appl. No.: 11/732,374

(22) Filed: Apr. 3, 2007

(65) Prior Publication Data

US 2008/0123815 A1 May 29, 2008

Related U.S. Application Data

(63) Continuation of application No. 10/793,424, filed on Mar. 4, 2004, now Pat. No. 7,233,645.

(60) Provisional application No. 60/451,941, filed on Mar. 4, 2003.

(51) Int. Cl.
H05G 1/54 (2006.01)
H05G 1/22 (2006.01)

(52) U.S. Cl. ............... 378/118; 378/106; 378/112

(58) Field of Classification Search ............ 378/102, 378/104–106, 110, 112, 114, 115, 117, 118
See application file for complete search history.

(56) References Cited

U.S. PATENT DOCUMENTS

| | | | |
|---|---|---|---|
| 3,643,094 A | 2/1972 | Courtois |
| 3,789,289 A | 1/1974 | Bell et al. |
| 3,864,012 A | 2/1975 | Cutchaw |
| 4,047,242 A | 9/1977 | Jakob et al. |
| 4,072,865 A | 2/1978 | Craig et al. |
| 4,139,771 A | 2/1979 | Dennhoven et al. |
| 4,200,796 A | 4/1980 | Murakami et al. |
| 4,646,338 A | 2/1987 | Skillicorn |
| 4,694,480 A | 9/1987 | Skillicorn |
| 4,710,860 A | 12/1987 | Tsuchiya |
| 4,794,506 A | 12/1988 | Hino et al. |
| 4,930,145 A | 5/1990 | Sherwin et al. |
| 4,979,198 A | 12/1990 | Malcolm et al. |
| 5,077,771 A | 12/1991 | Skillicorn et al. |
| 5,153,900 A | 10/1992 | Nomikos et al. |
| 5,267,138 A | 11/1993 | Shores |
| 5,416,816 A | 5/1995 | Wenstrup et al. |
| 5,548,189 A | 8/1996 | Williams |
| 5,550,889 A | 8/1996 | Gard et al. |
| 5,581,590 A | 12/1996 | Mori et al. |
| 5,581,591 A | 12/1996 | Burke et al. |
| 5,754,414 A | 5/1998 | Hanington |
| 5,927,482 A | 7/1999 | Davies |

(Continued)

FOREIGN PATENT DOCUMENTS

GB 2007480 A 5/1979

(Continued)

OTHER PUBLICATIONS 40 kV X-ray Module, Technical Specification from catalog of Inpho, Inc.

(Continued)

*Primary Examiner*—Edward J Glick
*Assistant Examiner*—Thomas R Artman
(74) *Attorney, Agent, or Firm*—Wolf, Greenfield & Sacks, P.C.

(57) ABSTRACT

A control system for an X-ray source includes a sensor interface for receiving one or more sensor signals representative of operation of the X-ray source; a programmable controller operative in response to the one or more sensor signals and a sequence of control instructions for generating one or more control signals for controlling the X-ray source; and a control interface for supplying the one or more control signals to the X-ray source, either directly or indirectly.

1 Claim, 26 Drawing Sheets

U.S. PATENT DOCUMENTS

| | | |
|---|---|---|
| 6,087,787 A | 7/2000 | Williams |
| 6,169,782 B1 | 1/2001 | Zetterlund |
| 6,259,615 B1 | 7/2001 | Lin |
| 6,282,260 B1 * | 8/2001 | Grodzins .................. 378/87 |
| 6,339,635 B1 | 1/2002 | Schardt et al. |
| 6,370,218 B1 | 4/2002 | Toth et al. |
| 6,426,997 B1 | 7/2002 | Fuchs et al. |
| 6,453,009 B2 | 9/2002 | Berezowitz et al. |
| 6,493,419 B1 | 12/2002 | Dinsmore |
| 6,494,618 B1 | 12/2002 | Moulton |
| 6,661,876 B2 | 12/2003 | Turner et al. |
| 6,687,332 B2 | 2/2004 | Smyth |
| 6,738,275 B1 | 5/2004 | Beland |
| 6,778,633 B1 | 8/2004 | Loxley et al. |
| 7,085,351 B2 | 8/2006 | Lu et al. |
| 2004/0109536 A1 | 6/2004 | Shefer et al. |
| 2005/0018817 A1 | 1/2005 | Oettinger et al. |
| 2006/0098778 A1 | 5/2006 | Oettinger et al. |

FOREIGN PATENT DOCUMENTS

JP     05-031740 A     2/1993

OTHER PUBLICATIONS http://www.medphys.ucl.ac.uk/research/acadraphys/photon.htm, 3 pages, Photon Radiosurgery from Department of Medical Physics and Bioengineering at University College London.

* cited by examiner

SYSTEMS AND METHODS FOR CONTROLLING AN X-RAY SOURCE

CROSS REFERENCE TO RELATED APPLICATIONS

The present application claims the benefit, under 35 U.S.C. § 119(e), of U.S. Provisional Application Ser. No. 60/451,941, filed Mar. 4, 2003, and entitled "Microcontroller-based Power Supply and Control System for an X-ray Source Module" and is a continuation of application Ser. No. 10/793,424, filed Mar. 4, 2004, which are hereby incorporated by reference.

FIELD OF THE INVENTION

This invention relates to x-ray sources and, more particularly, to control systems and methods for x-ray sources.

BACKGROUND OF THE INVENTION

X-ray technology has a wide range of uses, including medical applications, x-ray fluorescence (XRF) analysis and other applications. XRF systems analyze materials based on the x-rays that they fluoresce when impacted by other x-rays. XRF systems often are used in scrap metal sorting systems, lead paint detection, hazardous waste site investigation, ore classification in mining, general industrial quality control, and other applications.

A typical XRF system operates as follows. An x-ray source, for example, an x-ray tube or a radioactive isotope, stimulates a material with impacting x-rays. The impact of these x-rays causes the material to fluoresce, and this x-ray induced fluorescence has an energy spectrum that is characteristic of the elemental composition of the material. Accordingly, this energy spectrum may be analyzed to determine one or more identifying characteristics of the material. For example, the material may be identified or classified based on its fluorescence energy spectrum, contaminants may be identified within the material, or the elemental composition of the material may be determined. A variety of XRF systems are in use, including handheld XRF instruments, bench-top systems, and conveyor belt systems in which materials are conveyed into an area in which the material is impacted with x-rays and the resulting fluorescence spectrum detected and analyzed.

XRF systems typically include an x-ray module containing an x-ray source to generate x-rays and a separately housed XRF analysis module to analyze the fluoresced x-rays. In some cases, the x-ray module and the XRF analysis module are not connected, and in some cases the separately housed units are connected by one or more wires. The x-ray module typically includes an x-ray source, an x-ray power supply, and analog control electronics consisting of one or more interconnected, discrete analog devices. The analog control electronics control the x-ray power supply, which supplies power to the x-ray source. In some x-ray modules, the analog control electronics are hardwired to detect voltages or currents associated with the x-ray power supply and to adjust the power supply in response to these voltages or currents. However, the analog control electronics of x-ray modules do not include any centralized processing unit and are not capable of being programmed with instructions (e.g. software).

SUMMARY OF INVENTION

According to the first aspect of the invention, a control system for an X-ray source is provided. The control system comprises a sensor interface for receiving one or more sensor signals representative of operation of the X-ray source; a programmable controller operative in response to the one or more sensor signals and a sequence of control instructions for generating one or more control signals for controlling the X-ray source; and a control interface for supplying the one or more control signals to the X-ray source, either directly or indirectly.

According to a second aspect of the invention, a method for controlling an X-ray source is provided. The method comprises receiving one or more sensor signals representative of operation of the X-ray source; using a programmable controller for generating one or more control signals for controlling the X-ray source in response to the one or more sensor signals and a sequence of control instructions; and supplying the one or more control signals to the X-ray source, either directly or indirectly.

According to a third aspect of the invention, a control system for an X-ray source is provided. The control system comprises a position sensor configured to sense a position of an X-ray output of the X-ray source and for generating a position signal in response to the sensed position; and a controller operative in response to the position signal to generate one or more control signals for adjusting the position of the X-ray output.

According to a fourth aspect of the invention, a control system for an X-ray source is provided. The control system comprises a detector interface for receiving one or more detector signals representative of a characteristic of an X-ray output of the X-ray source; a controller operative in response to the one or more detector signals to generate one or more control signals for controlling the X-ray source; and a control interface for supplying the one or more control signals to the X-ray source, either directly or indirectly.

According to a fifth aspect of the invention, a control system for an X-ray source is provided. The control system comprises a detector interface for receiving one or more detector signals representative of an effect produced by an X-ray output of the X-ray source; a controller operative in response to one or more detector signals to generate one or more control signals for controlling the X-ray source; and a control interface for supplying the one or more control signals to the X-ray source, either directly or indirectly.

DETAILED DESCRIPTION

Figure 1:
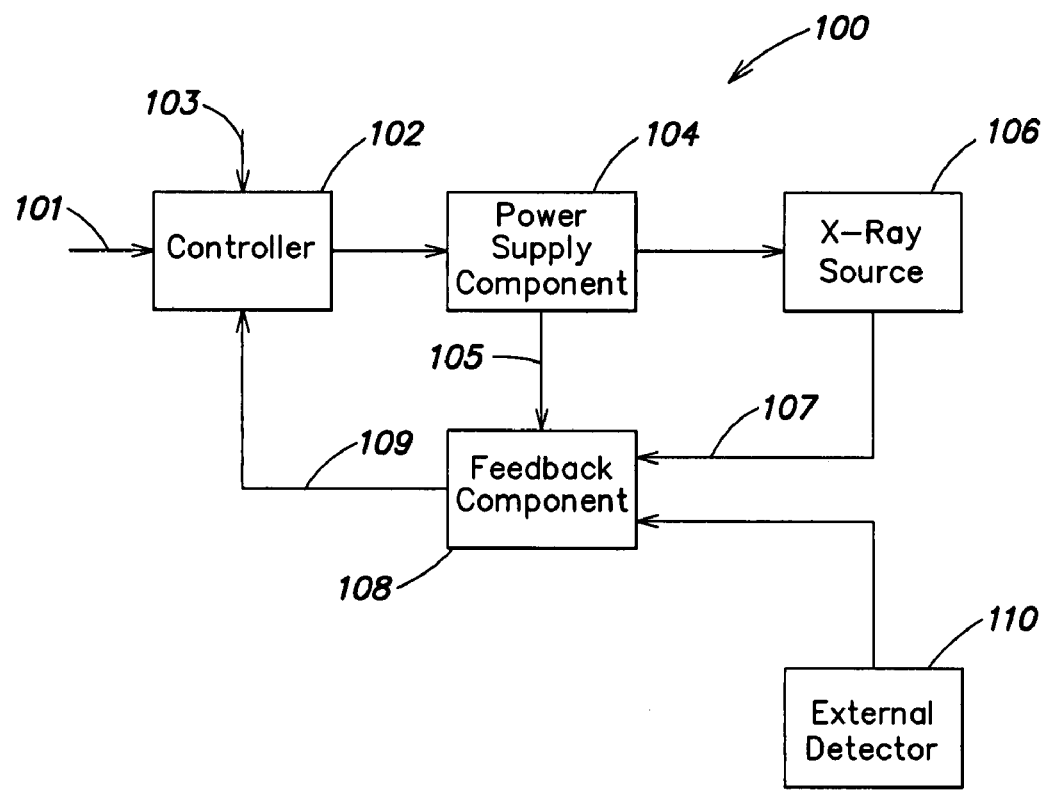
FIG. 1 is a block diagram illustrating an example of a system for controlling the generation of x-rays by an x-ray source.

Disclosed herein is a system for controlling the generation of x-rays using a controller. Such system may be or include a controller-based x-ray module which is a component of a larger system. As used herein, a "controller" is a circuit, comprising a set of one or more interconnected integrated circuits, programmed with or capable of being programmed with a set of instructions, (e.g. software), and including a central processing unit (CPU) to execute the set of instruction to control one or more other circuits, devices, components thereof or any suitable combination thereof. A controller may be or include any of the following: a microcontroller, microprocessor, or a digital signal processor. Although various embodiments of the invention are disclosed primarily in relation to use of a microcontroller, it should be appreciated that the invention is not so limited. Embodiments of the invention may be implemented using a microprocessor, a digital signal processor or other type of processor, for example, in place of a microcontroller.

Further, although various embodiments of the invention are disclosed primarily in relation to use of a controller, it should be appreciated that the invention is not so limited. Embodiments of the invention may be implemented using a control component that is not a controller. For example, embodiments of the invention may be implemented using a control component that is not programmable with instructions and/or does not include a CPU. Examples of such control components include control components formed by one or more interconnected analog circuits, which each may include one or more discrete circuit elements connected by wires (e.g., hard-wired analog circuits), programmable logic circuits (e.g., programmable logic arrays (PLAs) or other types or programmable logic circuits), or any suitable combination thereof.

In some embodiments, a controller may be operative to automatically adapt control of an x-ray source (e.g., an x-ray tube) based on the value of a detected property of a physical phenomenon associated with the generation of the x-rays, or associated with an effect induced by exposure to x-rays. As used herein, a "physical phenomenon" may include any of: an electrical phenomenon, a magnetic phenomenon, a thermal phenomenon, a radiative phenomenon, other physical phenomenon or a combination thereof.

An x-ray module controlled by a controller provides improved performance and additional functionality and flexibility over known x-ray modules using discrete analog or otherwise non-programmable components. Further, a controller-based x-ray module can be manufactured at a lower cost than x-ray modules based on the use of discrete analog control components due to a potential reduction in the number of individual components necessary to implement various functions which may now be performed by the controller software, and because of the improved capability for self-test, reducing otherwise necessary manufacturing resources required for this purpose.

Use of a controller enables "real time" control of an x-ray source (e.g., an x-ray tube), enabling dynamic adjustment of parameters to control the operation of the x-ray tube and its power supply. In contrast, in known systems, parameters defining the behavior of the control system cannot be dynamically adjusted during operation of the x-ray module and typically require physically changing electrical components to different values in order to alter behavior. Use of a controller permits control system parameters to be readily adjusted through programming changes, avoiding the need to change individual component values to alter control system behavior.

X-ray system functionality may be adjusted by reprogramming the controller (e.g., with software) as opposed to having to manually adjust hardware components of the x-ray module. The controller also may be configured to minimize or eliminate hardware errors or temperature effects, which may improve performance and accuracy of the x-ray output. Use of a controller also enables the x-ray module to communicate with external systems and other x-ray modules through one or more communication interfaces. Thus, the controller may be configured to exchange communications (e.g., instructions or information) with remote components.

Also described herein is a system for controlling the generation of x-rays that impact a material and cause the material to produce photonic emissions (e.g., x-rays or optical photons). A control component of this system may be operative to control an x-ray source to generate the x-rays and to adapt automatically the control of the x-ray source based on a value of a detected property of the photonic emissions.

A system for controlling generation of x-rays using one or more deflection coils is also described herein. The x-rays may be generated by an x-ray tube that includes a filament from which an electron beam is generated that impacts a target within the x-ray tube. The one or more deflection coils may be operative to deflect at least a portion of the electron beam. The system may include a control component to automatically adjust the one or more deflection coils based on a value of a detected property (for example, x-ray intensity) of the generated x-rays. In some embodiments, the system includes a plurality of deflection sensors disposed about the output of the x-ray tube, from which a plurality of values of the detected property may be detected. The control component may be configured to automatically adjust the deflection coil based on these values.

In some embodiments, two or more (e.g., an array) of x-ray modules (e.g., any of the x-ray modules described herein) are connected by one or more transmission media, for example, to form a network. Each x-ray module may include a controller to control an x-ray source and an interface to enable communications to be exchanged with one or more of the other x-ray modules. Each of the x-ray modules may be configured to impact a subject and/or detect emissions from the subject, as described in more detail below.

Control of the current in one or more deflection coils enables the positioning of the electron beam on the target of the x-ray tube which may correct otherwise off-center beams, thereby improving manufacturing yields of x-ray tubes. Further, the target may be preconfigured with a variety of different materials, and control of the current in the deflection coils may be utilized to direct the beam to one or more particular materials of the target, thus changing the output of the x-ray tube.

In some embodiments of the invention, the control system of an x-ray module may be configured to automatically perform any of a variety of tests (i.e., self-tests) upon itself. Such tests may include tests performed during operation of the x-ray module to: verify proper operation, identify fault conditions, provide predicted failure analysis, and to perform diagnostic tests. For example, in an x-ray tube containing a heated filament electron source, the metal that serves as the filament gradually evaporates, causing the filament to break. Use of a controller within the x-ray module may enable the x-ray module to be configured to monitor the condition of the filament, and to notify a user of such condition (e.g., impending failure). Further, the self-test capability of an x-ray module may be used during the manufacturing of the x-ray module (e.g., "burn-in testing") to improve the quality control of such x-ray modules.

In some embodiments of the invention, a controller-based x-ray module (e.g., any of the x-ray modules described herein) is part of a hand-held system. For example, the system may be housed within a housing, and the combined weight of the system and housing, and the configuration of the housing, may be such that the system is suitable for being carried and operated in one or both hands of a human.

In some embodiments, a system is provided that includes a modular, controller-based (e.g., microcontroller-based) control system for generating and controlling the output of a miniature x-ray tube. Such a system may include any of integrated, controller-based electronics and a power supply necessary to generate electron beam current for the x-ray tube. For example, if thermionic emission from a hot filament is used to create the electrons in the electron beam, generating an electron beam may include heating the x-ray tube filament under precision control by the controller. The system further may include any of: a resonant converter-based, high-voltage power supply which powers a high-voltage multiplier (used to create high voltage to accelerate the electron beam), and feedback control circuits to monitor and maintain within tight tolerances the beam-accelerating voltage, beam current, and x-ray output. The control system may include any of: a means for deflecting the x-ray tube electron beam to various positions across a target area, and means for sensing the position of the electron beam on the target to permit active control of electron beam position. Examples of these means are described below. In some embodiments, any of the following may be provided: means for interfacing the control system to an external x-ray detector or other x-ray output monitor; means for interfacing the control system to input signals from other external sources for direct control of x-ray output; means for modulating the x-ray output, either in response to commands from an external system or directly by the module itself; modulation synchronization signals allowing external systems to synchronize or otherwise gather real-time data related to the modulation; digital and analog communications interfaces; and modem capability for communications through telephony.

Controller-based control provides improved control, accuracy and stability of an x-ray tube's accelerating voltage, beam current, electron beam position on the target and x-ray output over known systems that do not employ controller-based control. Further, the ability to modulate the x-ray output may be simplified through use of a controller. The controller enables control of the x-ray output by an external device in real-time through a communications interface, and also enables autonomous, or semi-autonomous control of the x-ray tube by allowing the controller to automatically set the x-ray accelerating voltage, beam current or x-ray output to pre-programmed levels. In this manner, the x-ray output can be made to vary automatically to some output profile which might vary with time or in response to external events, without the need for continual intervention by, and communication with, an external device.

Incorporation of a controller also provides the capability for calibration and error compensation, automatic self-test, continual monitoring of x-ray tube performance and performance variations over time and other parameters such as safety checks and monitoring, module identification, data logging, fault diagnosis and logging and limited telephonic servicing. A digital communications interface (either serial or parallel) may be provided to enhance capability for controlling the tube and for communicating information between the x-ray module and an external host computer.

A communications interface also provides the capability for multiple modules to be connected into an overall network, possibly also including an external host computer. This allows for multiple modules to be controlled through the communications network either by the external host computer, or by the modules themselves. A network of modules configured into an array would be capable of generating an x-ray field with characteristics that could not be achieved by a single module. Alternatively, multiple modules which are connected to a network may be distributed, perhaps along an assembly line for quality control purposes, such that each module is operating independently from the others, but all may be in communication with an external host computer which coordinates operation.

The systems and methods described herein, in which a controller is employed, represent an improvement over current state-of-the-art systems that use hardwired electronics to provide control functions. Functions previously accomplished by such hard-wired circuitry may be implemented using any of a controller, associated software, firmware or hardware, or any suitable combination thereof, as described below. Further, additional functionality not readily achievable by current, state-of-the-art systems may be realized, including any of the requisite x-ray tube control, calibration, error correction and compensation, fault monitoring, data logging and communications functions. Such additional functionality provides significant performance advantages and flexibility over current state-of-the-art systems.

Although the control systems and methods are described herein primarily in relation to the use of an x-ray tube in the module that utilizes a heated filament to generate thermionic electrons for an electron beam, the embodiments of the invention are not limited to such implementation, which is merely an illustrative embodiment. Controller-based control systems for x-ray tubes that may generate electron emission using other technologies (e.g., cold cathode or photo emission technologies) may be used to implement one or more embodiments of the systems and methods described herein.

The function and advantage of these and other embodiments of the present invention will be more fully understood from the examples described below. The following examples are intended to facilitate an understanding of the present invention and to illustrate the benefits of the present invention.

1. Overall System

FIG. 1 is a block diagram illustrating an example of a system 100 for controlling the generation of x-rays by an x-ray source 106. System 100 may include any of controller 102, power supply component 104, x-ray source 106 and feedback component 108. Power supply component 104 supplies the power to x-ray source 106 to generate x-rays. Feedback component 108 receives one or more input values 105 from power supply component 104 and one or more input values 107 from x-ray source 106 and external detectors or sensors 110. The feedback component 108 may be configured to provide an output 109, which may include inputs 105, 107 and 110 and/or information derived therefrom to controller 102. Controller 102 may receive feedback output 109 and one or more inputs 101, and may be configured with one or more control parameters 103. Based on the control parameters 103, inputs 101 and feedback output 109, controller 102 may control power supply component 104, which supplies power to x-ray source 106. Thus, controller 102 may control x-ray source 106 based on control parameters 103, inputs 101 and feedback outputs 109.

Figure 2:
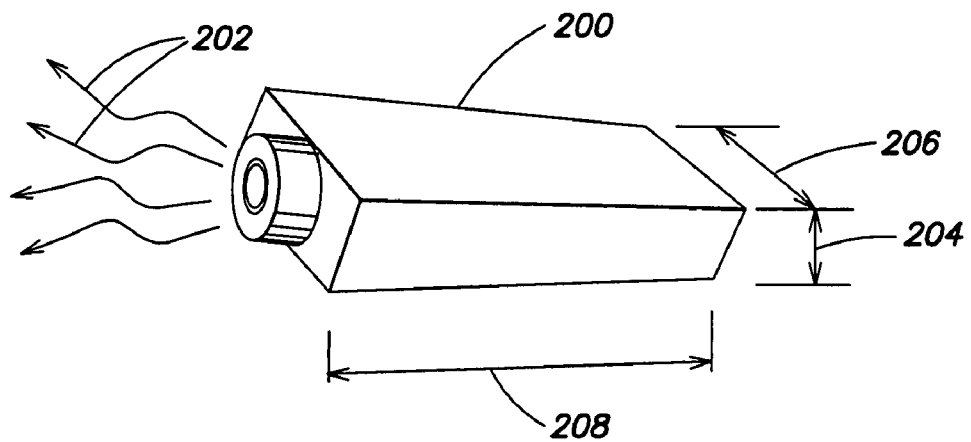
FIG. 2 is a perspective view illustrating an example of a housing for a system for generating x-rays.

Components 102, 104, 106 and 108 of system 100 may be packaged in any of a variety of ways, as described below in more detail. FIG. 2 is a perspective view illustrating an example of a housing 200 for system 100. The housing 200 may include any of components 102, 104, 106 and 108 and may generate x-rays 202. Housing 200 may be constructed and arranged with one or more inputs and outputs (not shown), enabling system 100 to exchange communications with one or more external devices, for example, other x-ray systems, computers, or other devices. Housing 200 may have relatively compact dimensions 204, 206 and 208, as small as one inch, three inches and eight inches, respectively, or even smaller. In some cases, these dimensions may be significantly smaller. Housing 200 is merely an illustrative example of a housing for system 100. This illustrative example is not intended to limit the scope of the invention, as any of numerous other implementations (e.g., other shapes and sizes) of a housing for system 100 are possible and are intended to fall within the scope of the invention.

Figure 3:
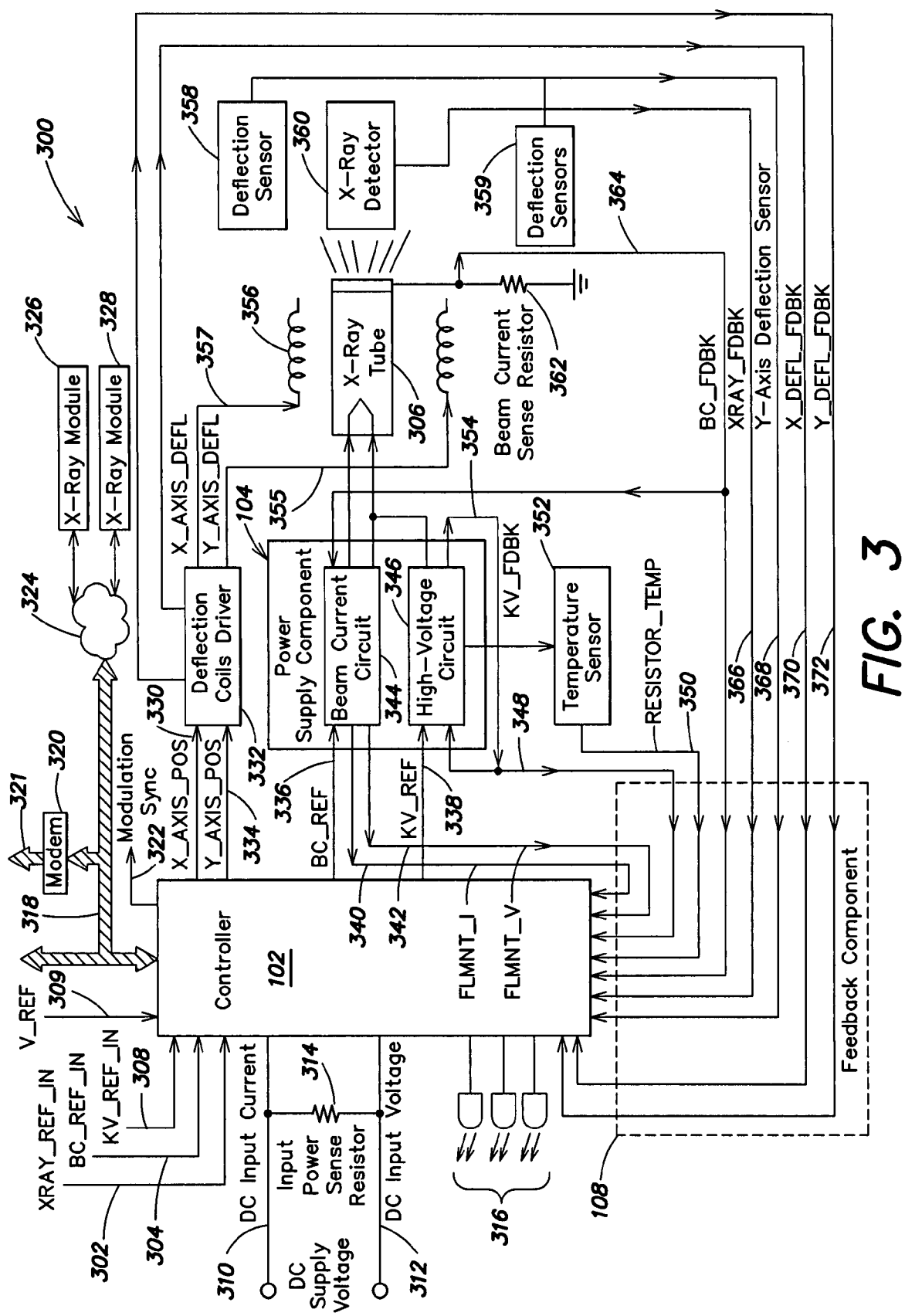
FIG. 3 is a block diagram illustrating an embodiment of the system shown in FIG. 1.

FIG. 3 is a block diagram illustrating an embodiment of the system 100 illustrated in FIG. 1. The elements depicted in FIG. 3 may be integrated into a single module or may be physically partitioned into smaller assemblies which are electrically interconnected.

Figure 4:
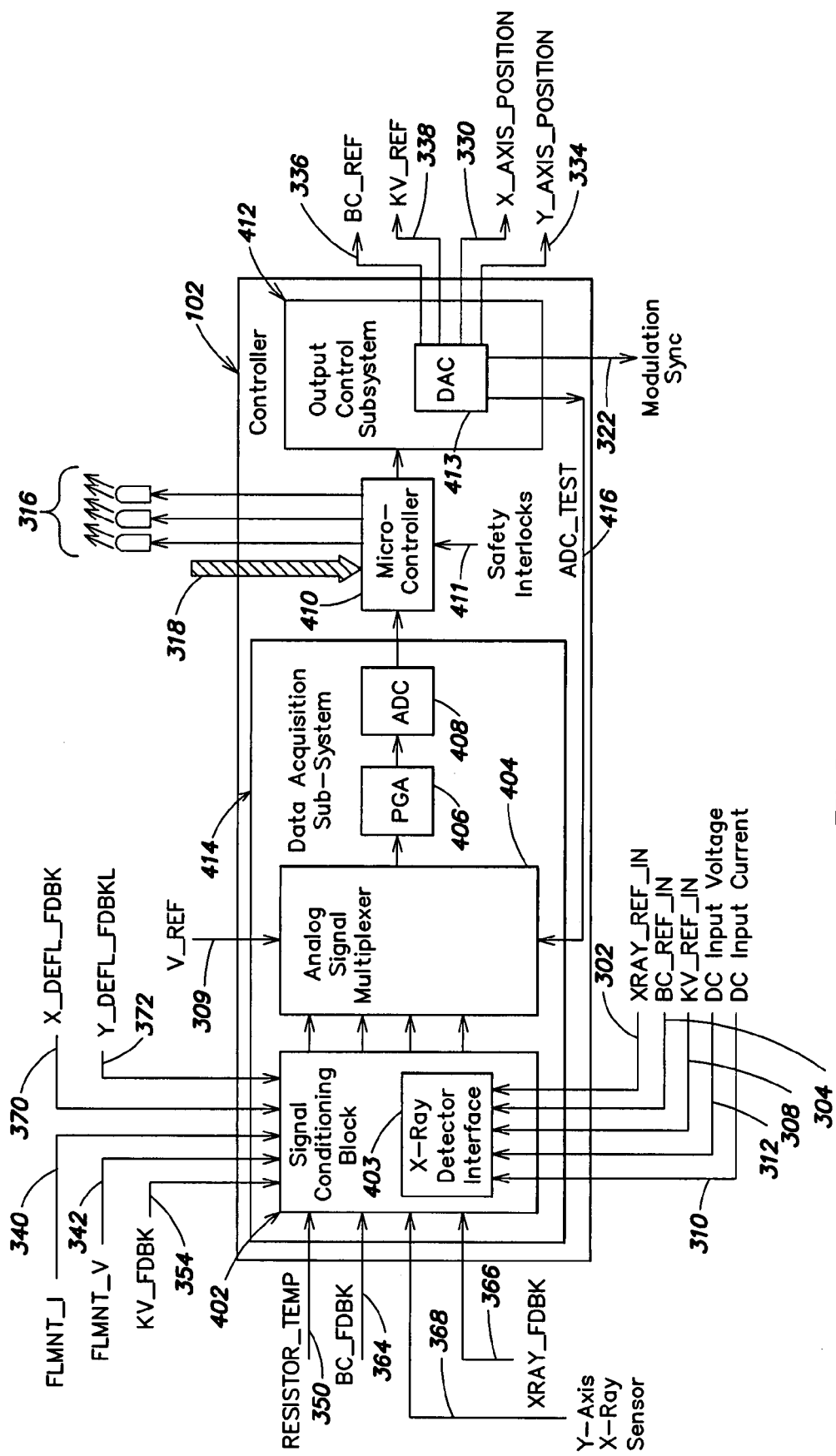
FIG. 4 is a block diagram illustrating an example of the controller shown in FIG. 3.
Figure 5:
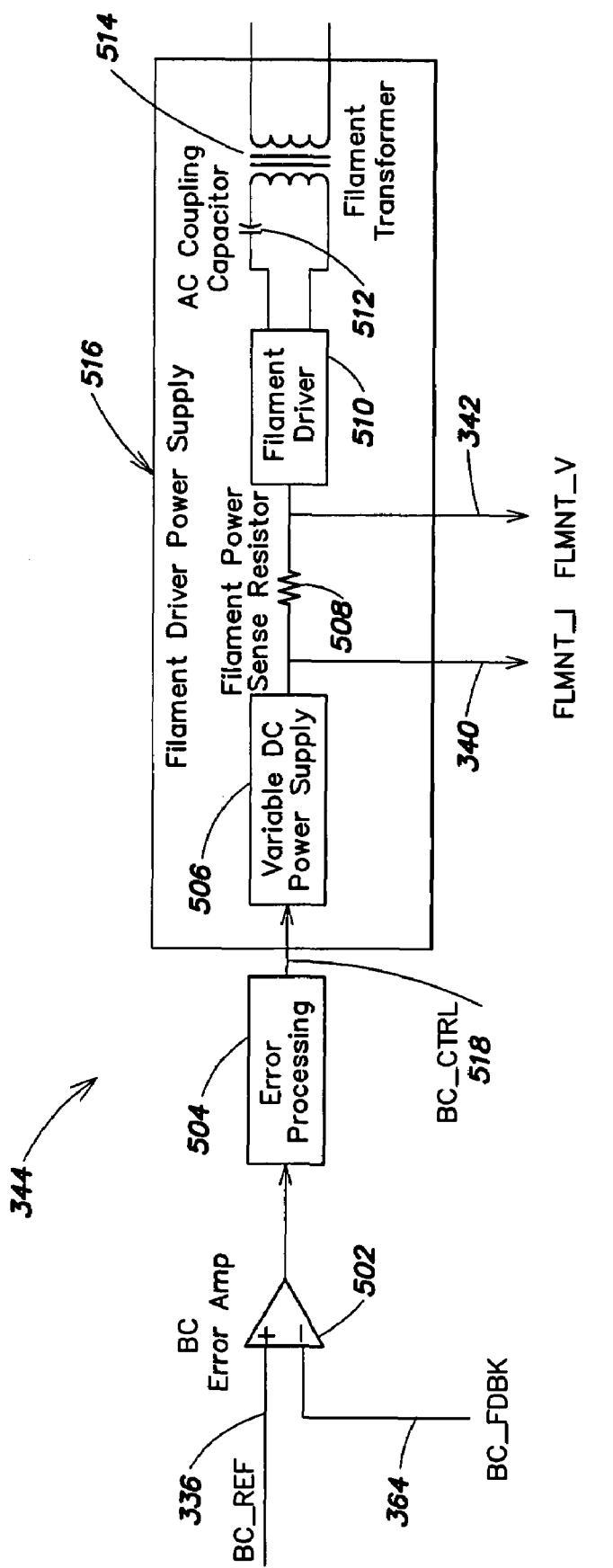
FIG. 5 is a circuit diagram illustrating an example of the beam current circuit shown in FIG. 3.
Figure 6:
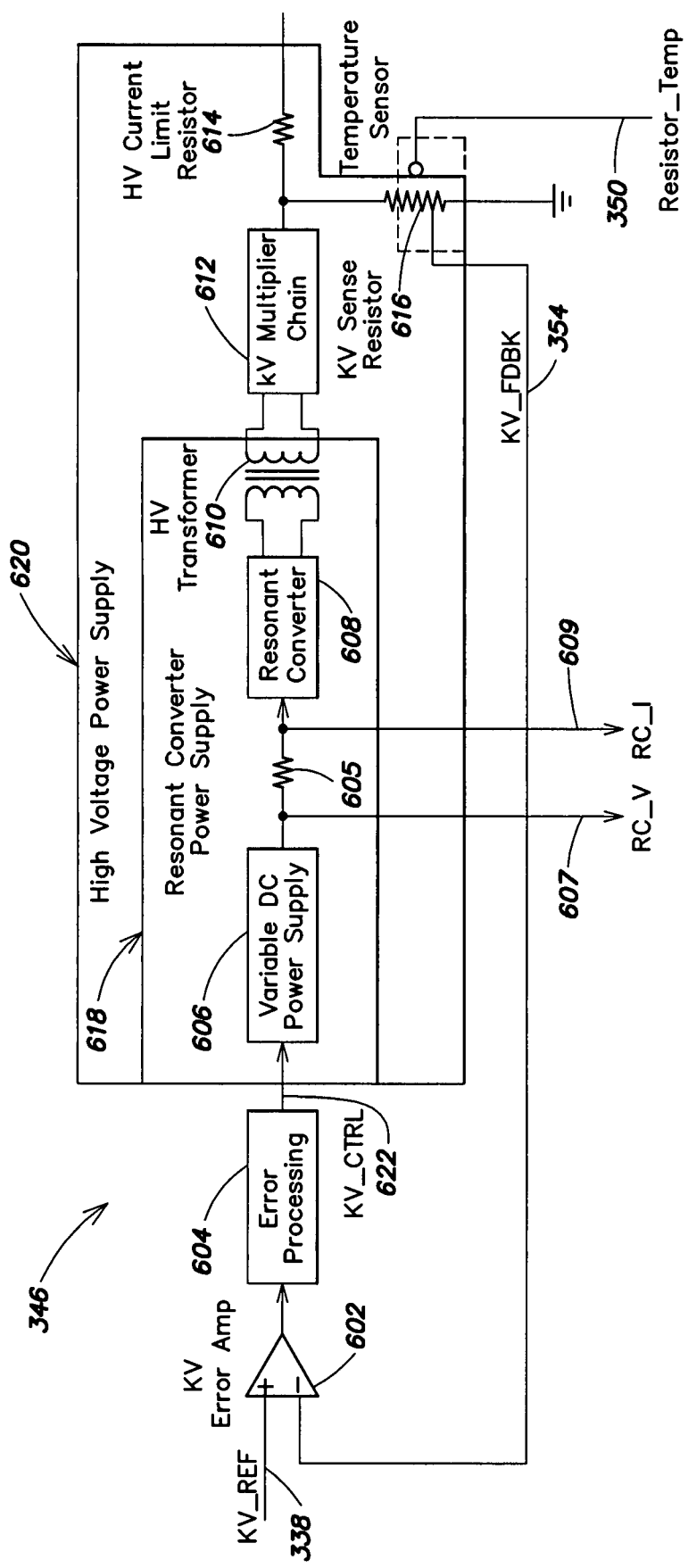
FIG. 6 is a circuit diagram illustrating an example of the high voltage circuit illustrated in FIG. 3.

System 300 may include, among other elements, controller 309 and power supply component 104. Power supply component 104 may include a beam current circuit 344 and a high-voltage circuit 346. FIG. 4 is a block diagram illustrating an example of the controller 102 shown in FIG. 3. FIG. 5 is a circuit diagram illustrating an example of the beam current circuit 344 shown in FIG. 3, and FIG. 6 is a circuit diagram illustrating an example of the high voltage circuit 346 shown in FIG. 3.

Various embodiments of the invention are described with reference to components that are illustrated in any of FIGS. 3-6. Although an x-ray tube 306 is depicted in the FIGS. 3, 14, 18 and 19 to illustrate connections to other components of system 300 and for discussing features and functions of the invention as they relate to the x-ray tube 306, embodiments of the invention are not limited thereto.

1.1 Power Supply and Control Components

A high-efficiency, microcontroller-based power supply architecture is described which minimizes power losses through the electronics and provides a high degree of control, performance and flexibility. Minimal power consumption is important in portable applications of this invention. The high-voltage circuit 346 provides a means of generating and controlling the negative voltage necessary to accelerate the x-ray tube's electron beam. A high-voltage output may be under closed-loop control and may be established through either a digital control value (KV_SET) or an analog input control signal (KV_REF_IN 308). A negative voltage may be used to permit operation of the tube 306 in a grounded-anode configuration, which may be desirable in certain applications. A power supply (not shown) can also provide positive high-voltage output, in which the cathode is at ground potential. In some embodiments, various combinations of a high-voltage multiplier chain 612, kV sense resistor 616 and current limit resistor 614 may be included. In other embodiments, these components may be included in external hardware with only the interface provided as part of system 300.

The beam current circuit 344 provides a means of generating and controlling the electron beam current in the x-ray tube 306. The beam current may be under closed-loop control, its magnitude may be established through either a digital control value (BC_SET) or an analog input control signal (BC_REF_IN 304). In some embodiments of this invention, a filament transformer 514 may be included. In other embodiments, this component may be included in external hardware, with only the interface provided by system 300.

System 300 also may include provisions for interfacing to an x-ray detector 360 for monitoring and control of x-ray output based on parameters characteristic of the x-radiation output such as x-ray energy or output flux, or on parameters induced by the x-radiation, such as x-ray backscatter within the x-ray tube, x-ray fluorescence, absorbed dose, or, in film exposure, changes in optical density. The detector may be placed directly in the beam path or outside of the path, or within the x-ray tube to detect backscattered x-rays, or may be positioned to monitor some aspect of the object of the x-ray exposure rather than monitoring the x-ray beam itself. An example of this is to measure x-ray fluorescence from a target irradiated by the x-rays. Based on the type of detector utilized, the detector output can be used to control and adjust any or all of the variables that affect x-ray emission from the x-ray tube 306, either singly or in combination. Such variables may include any of the x-ray tube beam current, accelerating voltage and electron beam position, and for modulated emission applications, pulse width and pulse frequency, and sinusoidal frequency and phase.

1.2 Microcontroller

Of the many microcontrollers commercially available, there are certain features that are desirable in devices considered for use in one or more aspects of the systems and methods described herein. Some of these features include low power consumption, flash memory for in-circuit reprogramability, serial communications capability, several digital I/O channels, multi-channel, high resolution analog data acquisition sub-system 414 and the ability to generate analog output voltages through a high resolution D/A converter 413 interface. It may be desirable to use devices that are inexpensive, readily available, and have good support hardware and development tools. These attributes are useful but not essential for practicing embodiments of the invention. In some embodiments of the invention, a microcontroller from the following microcontroller family may be used: the Cygnal Integrated Products C8051F020/1/2/3 Mixed Signal Microcontroller family.

1.3 Microcontroller-Based Data Acquisition and Output Control Subsystem

1.3.1 Data Acquisition Sub-System 414

The data acquisition sub-system 414 may include any of: a signal conditioning block 402, an analog signal multiplexer 404, a programmable gain amplifier (PGA) 406 and an A/D converter (ADC) 408. The multi-channel signal conditioning block 402 may provide an interface to the various electrical input signals, and may condition them appropriately for compatibility with the input requirements of the ADC 408. This conditioning may involve altering the gain, polarity, and/or DC offset of the signal. The analog signal multiplexer 404 may be utilized to select an individual input channel for application to the ADC 408.

In some embodiments, a programmable gain amplifier (PGA) 406 is introduced between the output of multiplexer 404 and the input of ADC 408. The PGA 406 may operate under software control and may adjust the gain as necessary to amplify or reduce the amplitude of the selected multiplexer output channel such that the signal amplitude closely matches the full-scale input range of the ADC 408. In this manner, small signals may be amplified prior to A/D conversion, thereby reducing quantization error in the acquired signal. The microcontroller 410 may subsequently divide the value of the acquired signal by the gain of the PGA 406 to arrive at the true value of the input signal.

1.3.2 X-Ray Detector Interface

An interface 403 to an external x-ray detector 360 may be provided, for example, within signal conditioning block 402. The purpose of this interface 403 may be to acquire information from the x-ray detector 360 which can subsequently be used by the microcontroller 410 to monitor and/or control a characteristic of the x-ray output or an effect induced by the x-ray irradiation.

In various embodiments, the interface 403 may be capable of communicating with one or more detectors capable of measuring x-ray energy, spectrum, flux, x-ray fluorescence (XRF), absorbed dose or other x-ray dependent parameters. Detectors sensitive to these parameters may produce a continuous analog or digital output, or a pulse-output mode, commonly seen in detectors operating in a photon counting mode. Detectors of both types include PIN diodes, ion chambers and photomultiplier tubes, and may incorporate a scintillator material in some embodiments.

The detector input signal may be applied first to a signal conditioning stage (e.g., within signal conditioning block 402) depending on the specific characteristics of the detector signal and what signal conditioning might be provided within the detector assembly itself. Signal conditioning can include offset correction, gain scaling, filtering, pulse shaping, threshold detection or other conversion. Subsequently this conditioned signal may be digitized and processed by the microcontroller 410 and the x-ray output adjusted accordingly.

In embodiments where the system 300 is interfaced to a detector, such as an XRF detector, the x-ray output may be controlled based on the nature of the x-ray fluorescence excited in an external substance. In this manner, control of the x-ray tube 306 may not be based solely on characteristics of the x-ray output (energy, flux) but also based on effects that the x-rays are producing as they interact with the ambient environment.

In embodiments where the system 300 is interfaced to an absorbed dose detector, such as an ion chamber, the time duration over which the x-rays are produced also may be controlled based on the output from the detector.

In applications where x-ray tube output control is based on feedback from a detector used to monitor some parameter of the effects induced in an irradiated sample, such as fluorescence or absorbed dose, the amplitude of the signal of the monitored parameter may be made independent of distance between the x-ray tube 306 and the surface, depending on the specific geometry of the application and the configuration of the detector. Control circuitry may be configured to respond to changes in detector feedback signal and to adjust the x-ray tube 306 accordingly to maintain a constant feedback signal, and thus the x-rays at the surface being monitored, at a constant value. The ability to irradiate a surface and maintain a constant x-ray state at the material surface may be of significant advantage in some portable applications in which, for example, an XRF analyzer cannot be brought into direct contact with the surface being irradiated.

1.3.3 Output Control Sub-System

The output control subsystem 412 may include a multi-channel D/A converter (DAC) 413, which may be interfaced to the microcontroller 410. The microcontroller 410 may be configured to set the output signals (BC_CTRL 518, KV_CTRL 622) as appropriate to control the filament drive power supply 516 and the high voltage power supply 620, respectively, based on the data acquired from the data acquisition subsystem 414.

In addition, an output signal (ADC_TEST 416) may be used in a loop-back mode to provide a known input voltage to the data acquisition sub-system 414 for self test and calibration purposes.

In some embodiments, the output control subsystem 412 also may include components to perform the functions performed by any of BC Error Amp 502, Error processing component 504, KV error amp 602 and error processing component 604. These functions are described in more detail below.

1.3.4 Self-Test and Calibration Feature

To achieve high accuracy, the data acquisition and output control sub-systems 414 and 412 may be provided with a means for self-test and calibration. In the embodiment shown in FIG. 4, a precision voltage reference input signal (V_REF) 309 and an output from the DAC 413 (ADC_TEST 416) may be provided as inputs to the analog signal multiplexer 404 of the data acquisition sub-system 414. Providing this information may enable determination of gain and offset errors in the data acquisition and output control subsystems 414 and 412. Self-testing and calibration may be implemented as follows.

To verify functionality of the DAC output and the PGA 406, the PGA 406 gain and the DAC output signal ADC_TEST 416 may be set to a known value. Signal ADC_TEST 416 may be acquired through the data acquisition sub-system 414, and the error between the actual and expected values may be calculated and stored. The PGA 406 gain then may be changed and signal ADC_TEST 416 acquired again. In this manner, a calibration curve of gain error versus gain setting for the PGA 406 may be developed.

As a cross-check, the fixed, precision input signal V_REF 309 also may be acquired at multiple PGA 406 gain settings, and errors between actual and expected values determined. This second error set may be compared to the calibration curve determined through signal ADC_TEST 416. Assuming that the DAC output contains no error, the comparison of these two sets of errors as a function of PGA 406 gain setting should be the same. Any differences can be explained by errors in the DAC outputs.

Loop-back testing also may be performed. The signal ADC_TEST 416 may be stepped through a range of output voltages with the data acquisition sub-system 414 acquiring a digital value resulting from each step. The error between expected value and the acquired value (after compensation for any PGA 406 gain error) may be calculated at each step. Errors are compared against allowable tolerance variations to verify proper function.

Figure 7:
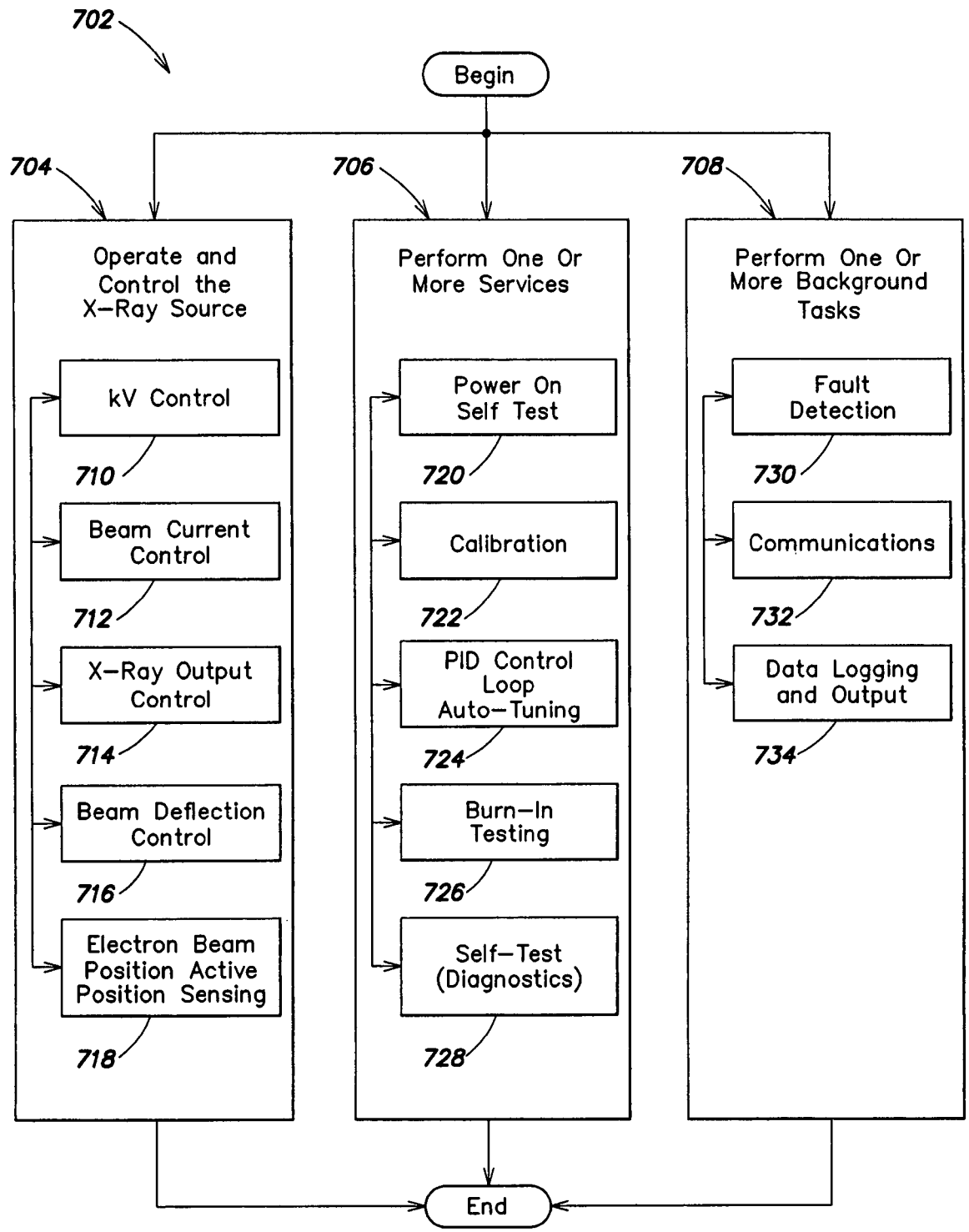
FIG. 7 is a flow chart illustrating an example of a method of controlling the generation of x-rays by an x-ray source using a controller.

FIG. 7 is a flow chart that illustrates an example of a method 702 for controlling the generation of x-rays by an x-ray source using a controller. In process 704, the x-ray source may be operated and controlled. Operating and controlling the x-ray source may include any of kV control step 710, described below in more detail in Section 1.4.2, beam current control step 712 described below in more detail in Section 1.4.3, X-Ray output control step 714 described below in more detail in Section 1.4.4, beam deflection control step 716 described below in more detail in Section 1.10.1, and electron beam position active position sensing step 718 described below in more detail in Section 1.11.

As illustrated in FIG. 7, any of steps 710, 712, 714, 716 and 718, and portions thereof, may be performed either in parallel (i.e., concurrently) or sequentially. Further, it should be appreciated that any of processes 704, 706 and 708, and portions thereof, may be performed in parallel or sequentially.

In process 706, one or more services may be performed. Services may include any of power-on self test step 720 described below in more detail in Section 1.17.2, calibration step 722 described below in more detail in Section 1.15.1.5.1, PID control loop auto tuning step 724 described below in more detail in Section 1.16.3, burn-in testing step 726 described below in more detail in Section 1.15.1.5.2, and self-test (diagnostics) step 728 described below in more detail in Section 2.16.5. Any of steps 720-728, and portions thereof, may be performed either in parallel or sequentially.

In process 708, one or more background tasks may be performed. The one or more background tasks may include any of fault detection step 730 described below in more detail in Section 1.16.4, communications step 732 described below in more detail in Section 1.16.8, and data logging and output step 734 described below in more detail in Section 1.16.7. Any of steps 730, 732 and 734, and any portion thereof, may be performed either in parallel or sequentially.

1.4 X-Ray Tube Control

1.4.1 Control System Approach

A generalized approach to control of the x-ray output is now described. In various embodiments, one or more desired characteristics of the x-ray output may be produced by controlling any of the x-ray tube's electron beam accelerating voltage, electron beam current, electron beam position on the target, beam deflection across the target, or any suitable combination thereof. These parameters may be monitored by the controller 102 to establish their current states. Microcontroller output signals may be utilized to drive one or more circuit elements which are used to adjust, in various embodiments, one or more of these parameters based on errors between the actual and desired values.

Referring to FIG. 3, sensors, detectors, other means and combinations thereof may be utilized to provide feedback information to the controller 102 regarding the current state of one or more variables that can affect the x-ray output, such as accelerating voltage or beam current. One or more of these system components also may be used to provide information on the state of the x-ray output, such as energy, spectrum or flux, or of the effects induced by irradiation from the x-ray output, such as x-ray fluorescence or absorbed dose.

In various embodiments, sensors may include circuit elements such as a high voltage sense resistor 616 to measure the accelerating voltage, a current sense resistor 362 for beam current measurement, and other circuit elements which may be employed to establish, directly or indirectly, electron beam position on the target. In addition, detectors, such as PIN diodes, ion chambers, photomultiplier tubes and scintillator-based detectors, may be utilized to measure some aspect of the x-ray output, such as energy, spectrum or spectrally-resolved emission, or flux, or to measure some aspect of the effects induced by irradiation from the x-ray output, such as x-ray fluorescence or absorbed dose.

The controller 102 may be operative to read the feedback inputs from each of the various sensor and detector inputs which may be provided in various embodiments. The controller 102 may adjust each of the various electrical outputs based on the combination of information provided by any or all of the feedback inputs and/or the difference between the actual and desired values of those inputs. In this manner, the control loop architecture is not limited to one feedback input dedicated to adjusting a single output. A combination of feedback inputs can be used, in various combinations, manners and weightings to provide better and more accurate control of each of the output parameters than is provided in known systems.

For example, cross-coupling effects that may exist between the electron beam accelerating voltage and beam current may be reduced. Due to component tolerances, ground drops or other circuit errors, a condition may be present such that a change in electron beam accelerating voltage may result in a small change in the electron beam current. By monitoring the accelerating voltage, and with prior knowledge of how the beam current varies with accelerating voltage, developed analytically or empirically, possibly through a calibration process, this information can be used to correct for any cross-coupling effects that may occur in the beam current as the voltage is changed. Thus, beam current may not controlled only by the feedback signal from beam current sense resistor 362, but also may be based on a feedback signal from the high voltage sense resistor 616.

Thus, in general, the controller 102 may be configured to accept input signals from a variety of sensors and detectors that monitor the relevant variables, parameters and induced effects of the x-ray output. Controller 102 uses that information in combination to adjust each of the control outputs, such as accelerating voltage, beam current or electron beam position on the target face. This results in the ability to achieve independent and more accurate control than can be achieved by known systems. Typically, in known systems, a specific control output is governed by a single control input. For example, the accelerating voltage is controlled based on feedback input solely from a high voltage sense resistor.

In addition, because the microcontroller 410 may be a component of each of the feedback control loops, a high degree of flexibility in control loop architecture can be realized. The controller 102 may be used to implement standard proportional-integral-derivative (PID) control, non-linear or multivariate control approaches, or, because of the flexibility that software provides, any arbitrary control loop approach.

In some embodiments, the performance achieved from a control loop architecture, whereby a single feedback input may be used to control a dedicated output, may be adequate. More detailed descriptions of embodiments of a PID control loop architecture based on this approach, as applied to the control of the electron beam accelerating voltage, beam current and x-ray output, are provided in the following sections.

1.4.2 KV Control Loop

In some embodiments, a standard proportional-integral-derivative (PID) control loop architecture may be implemented by the controller 102 to control the high voltage. Three scale factors, $K_p$, $K_i$ and $K_d$, corresponding to each of the three PID terms and specific to this control loop may be used to scale the error signal described below to create a control voltage output. By adjusting the values of these scale factors, the accuracy and transient response of the control loop can be modified. Other control loop architectures, including non-linear and multivariate architectures, can also be implemented. Multivariate control refers to an approach whereby the control output signal is a function of more than one feedback input signal and/or other input signals that are combined in some defined manner to produce the control output signal.

Operation of the high-voltage control loop circuit is now described. A reference digital input value (KV_SET) or analog input (KV_REF_IN 308) establishes the desired high voltage output. A feedback signal developed from the actual high voltage output (KV_FDBK 354) may be compared to the reference signal and an error signal may be developed by the controller 102. The three PID scale factors Kp, Ki and Kd, each may be individually multiplied by the error signal, the integral of the error signal and the derivative of the error signal respectively. The resulting three products may be summed together to create the control voltage (KV_CTRL 622), which may be then applied to the input of a high voltage power supply 620, which includes a resonant converter power supply 618. Power supplies based on a resonant converter architecture are well known for their high efficiency in performing DC-DC voltage conversion.

In this embodiment, the output of the resonant converter 608 may be applied to a step-up transformer 610. The output of the transformer then may be applied to the input of a multiplier chain 612, for example, a diode-capacitor voltage multiplier of a standard Cockroft-Walton configuration. The diodes in the multiplier chain 612 may be oriented to provide a negative high voltage output relative to electrical ground. In the grounded anode configuration, the output of the multiplier may be applied to the cathode of the x-ray tube 306 as the accelerating voltage. The output also may be sensed through a high voltage sense resistor 616 to develop the feedback signal (KV_FDBK 354) as discussed above. Other embodiments which do not include the step-up transformer 610, high voltage multiplier chain 612 or high voltage sense resistor 616, or combinations thereof, but instead rely on these components to be provided as hardware external to this system 300 are also possible.

Control of the high voltage output may be provided through adjustment of the reference digital input value (KV_SET) or analog input value (KV_REF_IN 308).

The parameter KV_SET, not shown explicitly in FIG. 3, may be a digital value provided to the controller 102 through a digital communications interface 318.

Figure 8:
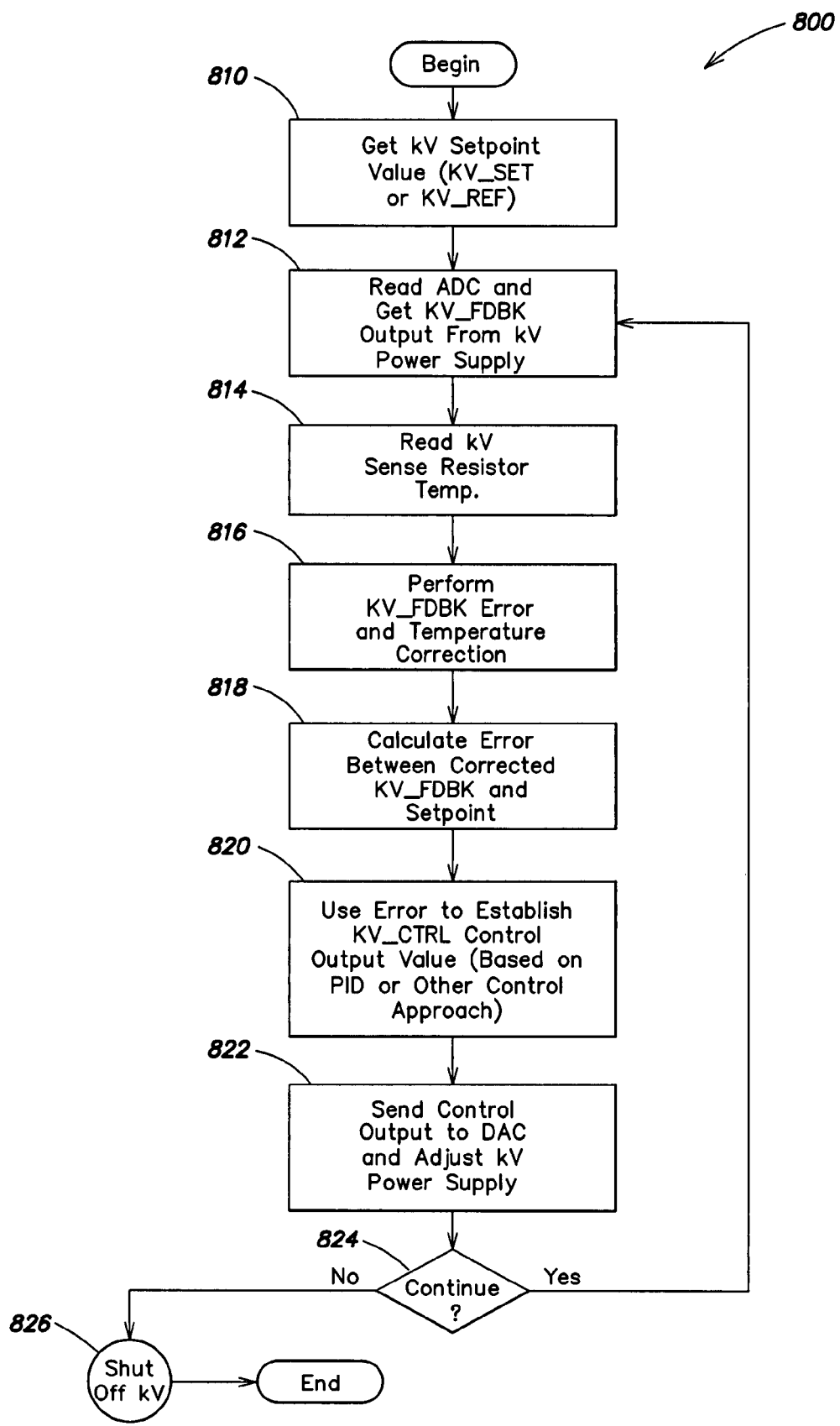
FIG. 8 is a flow chart illustrating a method of implementing a high voltage control loop.

High voltage control may be implemented as shown in FIG. 8. FIG. 8 is a flow chart that illustrates an example of a method 800 for implementing high voltage control, for example, as part of step 710. In step 810, a high voltage set point value (KV_SET or KV_REF) is obtained. In step 812, ADC 408 is read to obtain the KV_FDBK output from the high voltage power supply. In step 814, the sense resistor 616 temperature is sensed. In step 816, KV_FDBK error and temperature correction are performed. In step 818, an error between the corrected KV_FDBK value and the kV setpoint is calculated. In step 820, the calculated error is used to establish a KV_CTRL control output value, based on PID or other control approach. In step 822, the control output value is sent to DAC 413 to adjust the high voltage power supply. The process continues in step 824 by returning to step 812, or terminates in step 824 by shutting off the high voltage power supply in step 826.

1.4.3 Beam Current Control Loop

In some embodiments, a standard proportional-integral-derivative (PID) control loop architecture may be implemented by the controller 102 to control the beam current. Three scale factors $K_p$, $K_i$ and $K_d$, corresponding to each of the three PID terms and specific to this control loop may be used to scale the error signal described below to create a control voltage output. By adjusting the values of these scale factors, the accuracy and transient response of the control loop can be modified. Other control loop architectures, including non-linear and multivariate architectures, can also be implemented.

One embodiment of the operation of the beam current circuit 344 is now described. A reference digital input value (BC_SET) or analog input (BC_REF_IN 304) establishes the desired x-ray tube beam current output. A feedback signal developed from the actual beam current (BC_FDBK 364) may be compared to the reference signal and an error signal may be developed by the controller 102. The three PID scale factors Kp, Ki and Kd, may be each individually multiplied by the error signal, the integral of the error signal and the derivative of the error signal respectively. The resulting three products then may be summed together. In some embodiments, this summed signal may be applied to a linearization stage, which takes the fourth root of the summation. Configurations that do not employ this linearization stage, or employ variants of this stage are also possible. The output from any linearization stage employed may be the BC_CTRL signal 518, which may be applied to the input of a filament driver power supply 516 that provides heater current to the filament. The output of a filament driver 510 in power supply 516 may be applied to a high-voltage isolation filament transformer 514 that couples the filament supply output power to the x-ray tube filament maintained at a negative high voltage relative to the power supply output. Control of the beam current output is provided through adjustment of the reference digital input value (BC_SET) or the analog input value (BC_REF_IN 304).

The parameter BC_SET, not shown explicitly in FIG. 3, may be a digital value provided to the controller 102 through the digital communications interface 318 shown in FIG. 3.

The above-described embodiments included an x-ray tube 306 utilizing a heated filament to generate beam current by thermionic emission, and a BC_CTRL 518 signal applied to a filament drive power supply 516 to change the filament temperature in order to vary the thermionic emission. In other embodiments, x-ray tubes utilizing different technology to generate beam current, such as cold cathode x-ray tubes or photoemission based x-ray tubes, may be utilized. Such other types of x-ray tubes may not utilize a heated filament and rely on other techniques to generate the beam current. In these embodiments, a power supply tailored to the requirements of the specific x-ray tube 306 for generating beam current may be employed. The BC_CTRL signal 518 may be applied to that power supply to adjust the beam current in a manner similar to that described for the embodiment which incorporates filament drive power supply 516.

Figure 9:
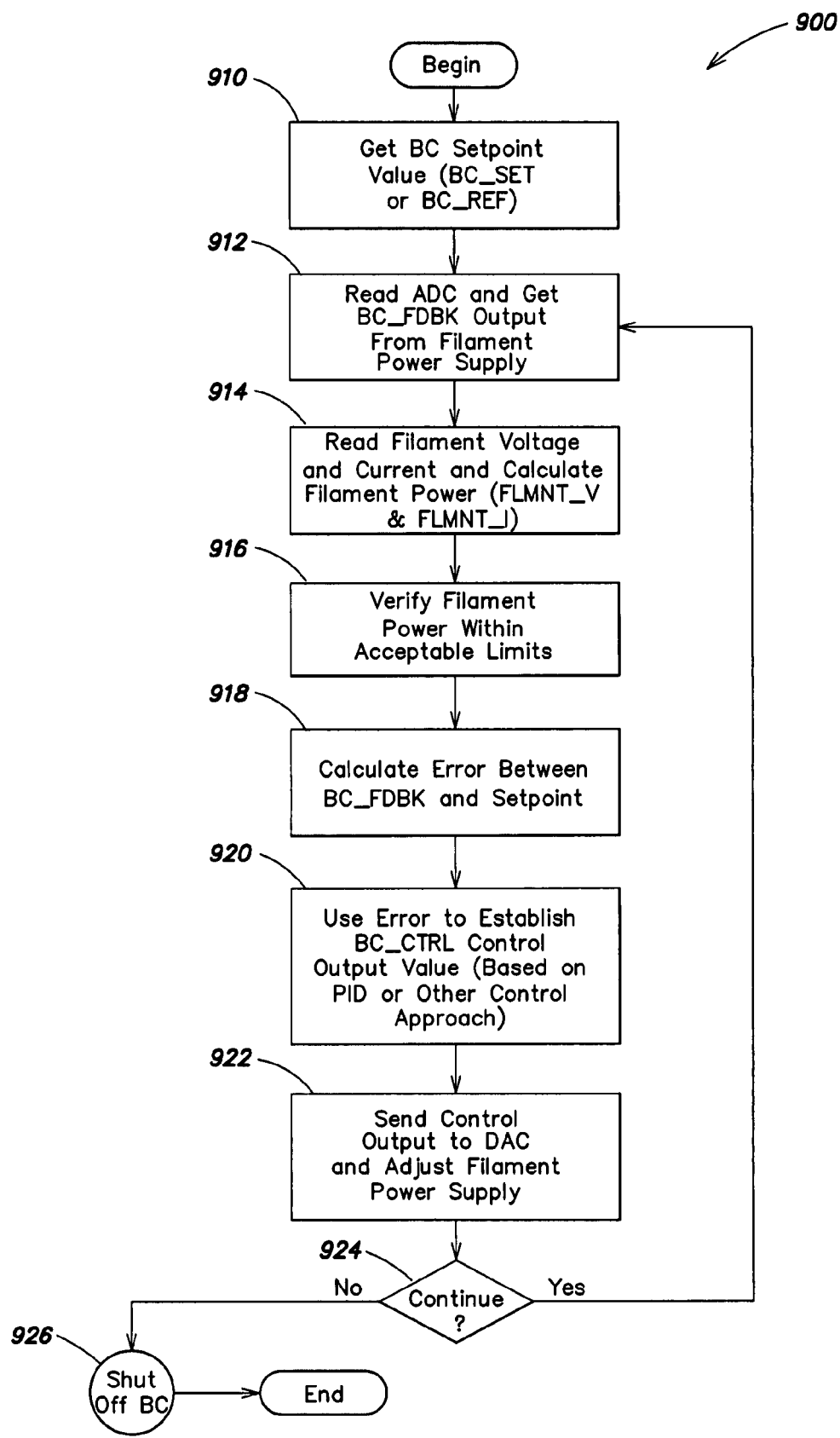
FIG. 9 is a flow chart illustrating an example of a method of implementing beam current control.

Beam current control may be implemented as shown in FIG. 9. FIG. 9 is a flow chart that illustrates an example of a method 900 for implementing beam current control, for example, as part of step 712. In step 910, a beam current set point value (BC_SET or BC_REF) is obtained. In step 912, the ADC 408 is read to obtain beam current feedback output BC_FDBK from the filament power supply. In step 914, the filament voltage and current are read, and a filament power is calculated. In step 916, the calculated filament power is verified to be within acceptable limits. In step 918, an error between the beam current feedback output BC_FDBK and the beam current setpoint is calculated. In step 920, the calculated error is used to establish a BC_CTRL control output value, based on PID or other control approach. In step 922, the control output value is sent to DAC 413 to adjust the filament power supply. The process continues in step 924 by returning to step 912, or terminates by shutting off the beam current power supply in step 926.

1.4.4 X-Ray Output Control Loop

In some embodiments, a standard proportional-integral-derivative (PID) control loop architecture may be implemented by the controller 102 to control the x-ray output. Three scale factors $K_p$, $K_i$ and $K_d$, corresponding to each of the three PID terms and specific to this control loop may be used to scale the error signal described below to create a control voltage output. By adjusting the values of these scale factors, the accuracy and transient response of the control loop can be modified. Other control loop architectures, including non-linear and multivariate architectures, can also be implemented.

In some embodiments, use of an x-ray detector 360 provides a means to control the x-ray output directly. As shown in FIG. 3, a detector 360 may be positioned in the path of the x-ray output such that it intercepts at least some of the beam. In other embodiments, the x-ray detector 360 may be positioned in other locations relative to the path of the x-ray output. The detector 360 may produce an output signal which may be a function of the x-ray output. Signal conditioning may be applied to the signal which then may be digitized and read by the controller 102. Processing algorithms may adjust the x-ray tube accelerating voltage and beam current as necessary to maintain the desired output as measured by the detector.

One embodiment of the operation of the x-ray control circuit is now described. A reference digital input value (XRAY_SET) or analog input (XRAY_REF_IN 302) establishes the desired x-ray tube beam current output. A feedback signal developed from the detector output (XRAY_FDBK 366) may be compared to the reference signal and an error signal developed by the controller 102. The three PID scale factors, Kp, Ki and Kd, each may be individually multiplied by the error signal, the integral of the error signal and the derivative of the error signal respectively. The resulting three products may be summed together to create the control voltage (XRAY_CTRL), which may be then applied as appropriate to either the input of the filament-drive power supply in order to adjust beam current or to the input of the resonant converter 608 to adjust the high voltage. Control of the x-ray output may be provided through adjustment of the reference digital input value (XRAY_SET) or the analog input value (XRAY_REF_IN 302).

The parameter XRAY_SET, not shown explicitly in FIG. 3, may be a digital value provided to the controller 102 through the digital communications interface 318.

Figure 10:
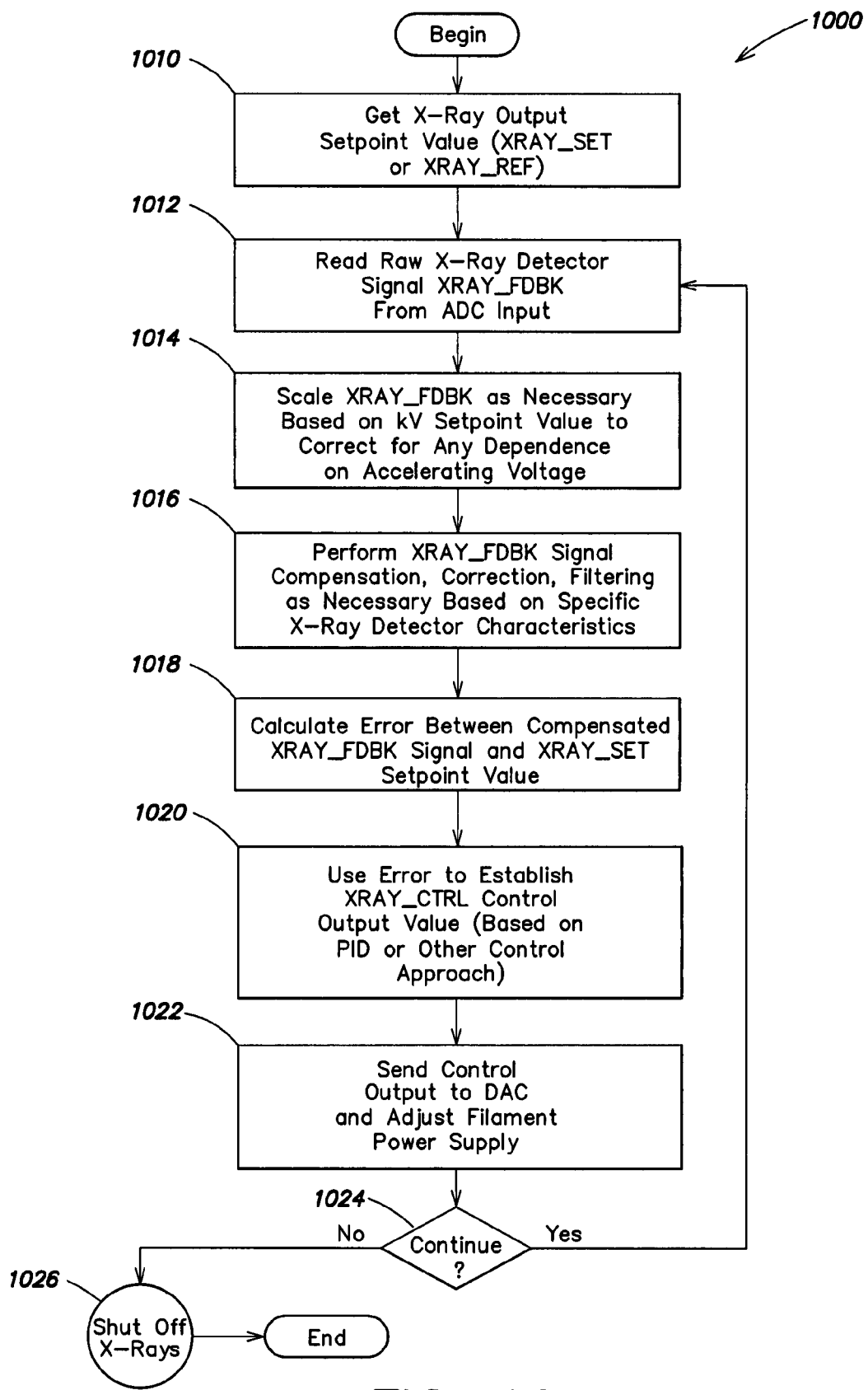
FIG. 10 is a flow chart illustrating an example of a method for implementing x-ray output control.

X-ray output control may be implemented as shown in FIG. 10. FIG. 10 is a flow chart that illustrates an example of a method 1000 for implementing x-ray output control, for example, as part of step 714. In step 1010, an x-ray output set point value (XRAY_SET or XRAY_REF) is obtained. In step 1012, the X-ray detector signal XRAY_FDBK is read from ADC 408. In step 1014, the X-ray detector signal XRAY_FDBK is scaled as necessary, based on the high voltage setpoint value, to correct for any dependence on accelerating voltage. In step 1016, signal compensation, correction and filtering of the x-ray feedback signal XRAY_FDBK are performed as necessary, based on specific x-ray detector characteristics. In step 1018, an error between the compensated X-ray detector signal XRAY_FDBK and the X-ray setpoint value is calculated. In step 1020, the calculated error is used to establish a control output value XRAY_CTRL, based on PID or other control approach. In step 1022, the control output value is sent to DAC 413 to adjust the filament power supply. The process continues in step 1024 by returning to step 1012, or terminates by shutting off the filament power supply in step 1026.

1.4.5 Analog Control Inputs

In some embodiments, analog control voltages (KV_REF_IN 308, BC_REF_IN 304, XRAY_REF_IN 302) may be used instead of, or in conjunction with, the digital values (KV_SET, BC_SET, XRAY_SET) to establish the HV accelerating voltage output, the beam current or x-ray output, respectively. Provision for use of analog control inputs provide added flexibility for interfacing to a variety of external hardware.

The analog control input voltage, KV_REF_IN 308 may be digitized with the resultant digital value used as KV_SET to establish the high voltage output. In a similar manner, BC_REF_IN 304 and XRAY_REF_IN 302 analog input voltages may be digitized with the resultant digital values used to establish the beam current and x-ray outputs, respectively.

Use of analog or digital input values to establish KV_SET, BC_SET and XRAY_SET values may be independent, allowing both mixed analog and digital means of control for added flexibility.

1.4.6 Alternate Control Loop Embodiments

In the preceding sections, a general control system approach has been described whereby software may participate in all aspects of setting and controlling an output parameter, based on an error between desired and actual values. In some applications, it may not be possible or desirable for software to participate in setting and/or actively controlling the plant. This may be due to considerations of microcontroller speed, resolution or cost, or considerations of system operational reliability or functional safety.

In this context, the "plant" may be the generalized output function, which represents any block under feedback control, for example, the high voltage power supply 620 (high voltage output and feedback) or the filament drive power supply 516 and x-ray tube 306 (beam current output and feedback).

Figure 11:
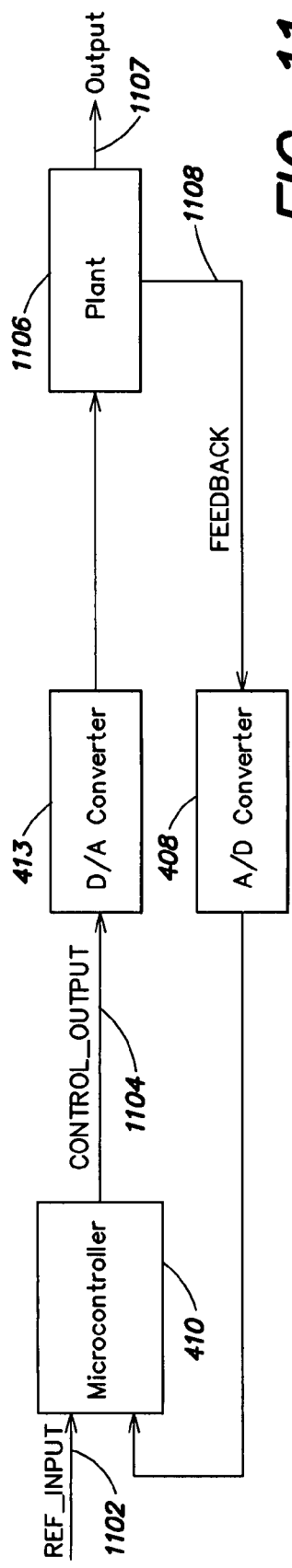
FIG. 11 is a block diagram illustrating an example of a software-based control system for controlling an x-ray source.
Figure 12:
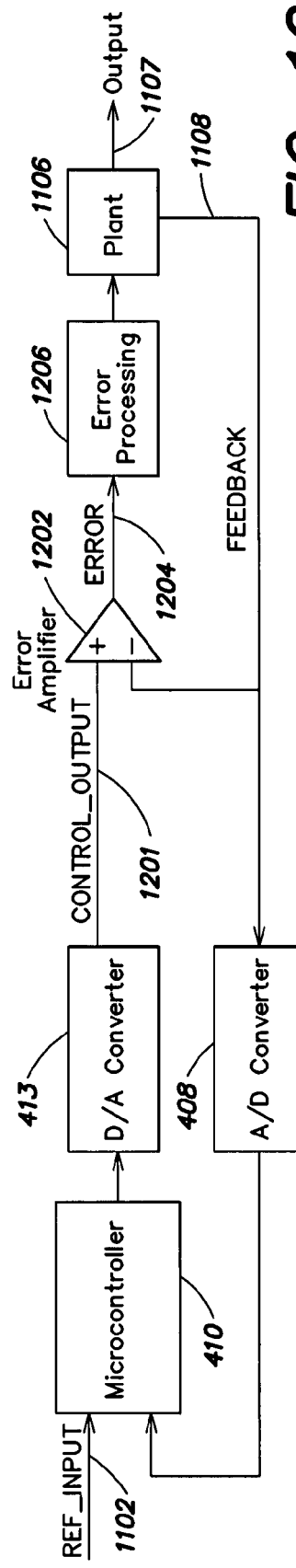
FIG. 12 is a block diagram illustrating an example of a software- and hardware-based control system for controlling an x-ray source.
Figure 13:
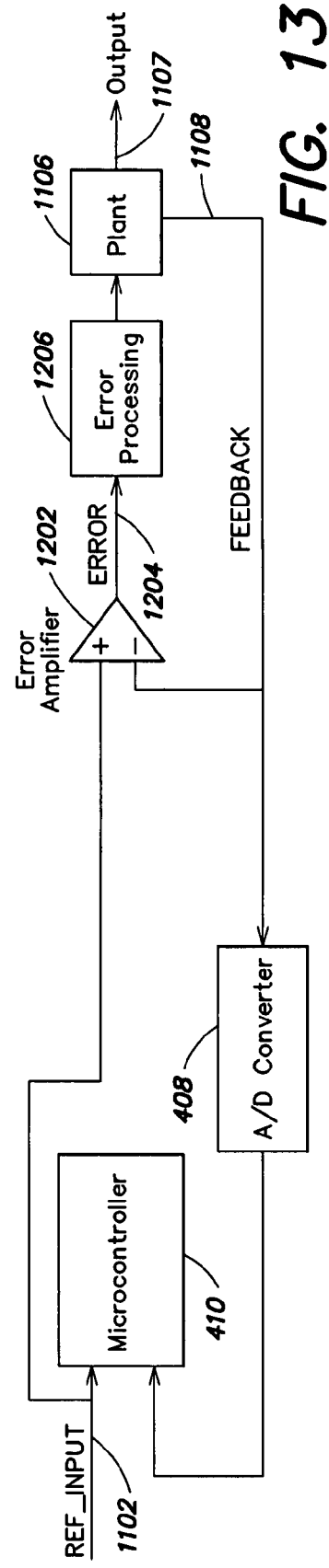
FIG. 13 is a block diagram illustrating an example of a software- and hardware-based control system for controlling an x-ray source.

FIGS. 11-13 depict three different control loop architectures with varying degrees of software participation in each. FIG. 11 is a block diagram illustrating an example of a software-based control system for controlling an x-ray source, where the plant output 1107 is both set and controlled through software. This is the architecture that has been discussed above. FIG. 12 shows an alternative architecture whereby software is allowed to establish the plant output 1107 but does not participate in the active real-time control. FIG. 13 shows another alternative architecture whereby software has no role in either setting or controlling the plant output 1107 and functions only to monitor the control loop behavior.

In various embodiments of this invention, any or all of these approaches may be applied independently to the different control loops within the overall system.

1.4.6.1 Full Software Control

In the preceding sections, a general control system approach has been described whereby software may read feedback inputs, develop an error based on the actual and desired values of those inputs, and adjust control output signals as necessary to reduce the error. FIG. 11 shows a generalized block diagram of this embodiment. A reference input (REF_INPUT 1102) may be provided to the microcontroller 410. The microcontroller 410 may set the desired operating output level of the plant 1106 by developing a control output (CONTROL_OUTPUT 1104) based on an error between the reference input and the feedback signal. Within the microcontroller 410, various control loop implementations, such as PID control, non-linear or multivariate (through use of multiple feedback signals from various sources), can be implemented.

1.4.6.2 Hardware-Based Feedback and Error Processing

FIG. 12 is a block diagram illustrating an example of a software and hardware-based control system for controlling an x-ray source. FIG. 12 shows another generalized control loop architecture based on a hardware implementation that can be implemented in different embodiments of the invention. In this approach, software may be used to set the output level of the plant 1106, but may not otherwise participate in the active control of the plant 1106. The error processing and control function in this architecture instead may be implemented in hardware. The reference input (REF_INPUT 1102) and plant feedback (FEEDBACK 1108) signals are still input to the microcontroller 410, which may be used to monitor those parameters. This provides the opportunity for the microcontroller 410 to detect fault conditions without directly participating in the active control of the plant 1106.

The microcontroller 410 also may output a control output (CONTROL_OUTPUT 1201) which establishes the operating point of the plant output 1107. Because software may establish this control output, it can assume an arbitrary relationship to the reference input signal 1102. In a simple case, the control output may be a copy of the reference input, which may be simply passed through the microcontroller 410. However, more complex or non-linear relationships are also possible. In another embodiment, the reference input signal may not be used at all. Rather, the microcontroller 410 may set the control output based on some pre-programmed set of instructions and not upon an external reference input signal.

The control output signal 1201 may be applied to an error amplifier 1202, which may develop an error signal (ERROR) 1204 based on a difference between the control output and the feedback signals. This error signal 1204 then may be applied to an error processing block 1206, which may be used to implement the specific control approach, such as PID control, non-linear or multivariate. In a multivariate embodiment, signals from other sensors or plants may be input to the error processing block 1206 and used in some combination to produce an output from the block that may be used to control the plant 1106.

1.4.6.3 Hardware Control, Software Monitoring Only

FIG. 13 is a block diagram illustrating another example of a software and hardware-based control system for controlling an x-ray source. FIG. 13 shows a third embodiment of a control architecture whereby software may not participate in any aspect of setting or controlling the plant output 1107. In this architecture, the reference input signal (REF_INPUT) 1102 may be applied directly to the error amplifier 1202 rather than being used by software to develop the control output shown in FIG. 12. The microcontroller 410 may be used only to monitor the reference input and the feedback signals, for purposes such as fault detection, but otherwise may play no role in establishing the plant output 1107.

1.5 Switching Power Supply Marker Pulse and Synchronization

For high efficiency, a resonant converter-based switching power supply may be used to drive the high voltage power supply 620. A switching power supply of a different configuration also may be utilized as the basis for the filament driver power supply 516, or x-ray tubes wherein a hot filament thermionically emits the electrons. Both radiated and conducted switching noise can be emitted from these power supplies. These noise components can potentially interfere with the operation and/or performance of external equipment, including in particular sensitive data acquisition systems. While good design practice can minimize this noise, it may not be possible to eliminate noise under all conditions. Accordingly, described below are means for mitigating its effects.

1.5.1 Marker Pulse

In sensitive data acquisition sub-systems (including, but not limited to analog, pulse-counting and pulse-amplitude acquisition sub-systems), the occurrence of a switching noise spike during the time interval during which data is being acquired can result in corrupted data compromising the ultimate performance of that system.

In some embodiments of the invention, a marker pulse output signal may be provided to the external hardware as an indication that a switching power supply has switched. The purpose of this marker pulse is to identify the time at which the switching occurs, and therefore the time at which switching noise may be present. In some embodiments, rising and falling edges of the marker pulse indicate switching turn-on and turn-off events for a particular switching power supply.

The marker pulse enables external hardware to take appropriate action upon its occurrence. This action could include rejection of any data which may have been acquired while the marker pulse became active. In this manner, external equipment has the ability to collect data only during the 'quiet' time interval between switching transitions in the power supplies, reducing the total noise which enters the external hardware.

Marker pulses may be provided for one or more switching power supplies in the x-ray module, providing comprehensive information regarding the switching state of the one or more power supplies. In different embodiments, these marker pulses can be output individually or multiplexed into a single marker pulse data stream.

1.5.2 Power Supply Synchronization

In some embodiments of this invention, the filament drive power supply 516 switching frequency may be derived from a clock oscillator, running asynchronously to the resonant frequency of the high voltage power supply 620. A particular disadvantage of operating these power supplies asynchronously is the independent occurrence of radiated and conducted switching noise at the switching frequencies of each supply. The combined rate of switching transitions between these power supplies is additive, such that noise spikes occur at a rate equal to the sum of the individual switching power supply frequencies. This may increase the difficulty for external hardware to filter or otherwise compensate for switching noise.

In embodiments where marker pulses are used to identify the occurrence of switching transitions, the total number of marker pulses which occur also is additive, resulting in a large number of marker pulses. External hardware responding to these marker pulses may experience a degradation in performance speed due to the need to respond to each marker.

In some embodiments, the filament driver and HV power supplies 516 and 620 are amplitude modulated and operated synchronously, such that their respective rising and falling edge switching transitions occur simultaneously. In these implementations, the clock oscillator of the filament drive power supply 516 may be replaced with a signal derived from the resonant frequency of the HV power supply 620. Thus, the HV power supply 620 continues to operate at resonance, which may be desirable to achieve high efficiency, and the filament drive power supply 516 runs synchronously with this resonant frequency. In this manner, the rate of switching noise transients, and therefore the number of marker pulses, may be reduced since switching transitions from both power supplies occur simultaneously, rather than independently as in the case of asynchronous operation.

1.6 Input Power Measurement

In some embodiments, x-ray module input voltage and current may be measured. In this manner, input power consumption can be established. This information can have several applications including self-test and performance checks of the x-ray tube 306.

In some embodiments, an input power sense resistor 314 may be placed in series with the DC Input Voltage 312 from an external power source. The voltages on either side of the resistor are measured to establish the voltage drop across the resistor and therefore current through the resistor, based on Ohm's law. The product of the voltage at the output side of the resistor and the current through the resistor may be a direct measure of the input power consumption. These measurements and calculations may be performed by the microcontroller 410.

1.7 Filament Power Measurement

The invention may have the means to measure filament voltage and filament current. In this manner, filament power consumption can be established. This information can have several applications including being used during testing as a means of filament quality control and identification of out-of-specification behavior, and as an indicator of filament aging and predictor of filament lifetime.

In some embodiments, a filament power sense resistor 508 may be placed in series with the output from the filament drive power supply 516. The voltages on either side of the resistor 508 may be measured to establish the voltage drop across the resistor 508 and therefore current through the resistor, based on Ohm's law. The product of the voltage at the output side of the resistor and the current through the resistor may be a direct measure of the filament power consumption. These measurements and calculations may be performed by the controller 102.

1.8 High Voltage Power Measurement

In some embodiments, power consumption by the high voltage power supply 620 may be measured. In some embodiments, the power consumption may be calculated, based on knowledge of any of the quiescent input power (the high voltage power supply 620 and the filament drive power supply 516 disabled), the filament drive power consumption, and the total power consumption. The high voltage power consumption in this case may be the result when the quiescent power consumption and the filament drive power consumption are both subtracted from the total input power consumption.

In other embodiments, a current sense resistor 605 inserted into the current path of the primary side winding of the resonant converter step up transformer 610 may be utilized. The voltages on one or both sides of this resistor RC_V 607 and RC_I 609, (depending on the embodiment) may be measured to determine current flow through, and voltage across the resistor 605 to determine the input power consumption to the resonant converter. In addition, the amplitude of the power supply input voltage to the resonant converter 608, or the peak amplitude of the resonant waveform may be used in conjunction with the sensed resistor current to determine power consumption.

In other embodiments, the duty cycle of the power supply 606 (which may be pulse-width-modulated switching power supply), which may be used to drive the resonant converter high voltage step-up transformer 610, may be measured by the controller 102. This information, in conjunction with knowledge of the supply voltage and component values may be utilized to calculate power consumption.

1.9 Temperature Measurement of KV Sense Resistor

The KV sense resistor 616 may be a high ohmic valued voltage divider connected to the high voltage output of the high voltage power supply 620. The output of this high voltage sense resistor 616 at the tap output may be a scaled representation of the high voltage impressed across it. For high accuracy in setting and maintaining the high voltage across variations in temperature, it may be desirable to know the divide ratio of the high voltage sense resistor 616, and for the divide ratio to be stable across the temperature range of interest. Since the divide ratio may vary with temperature per manufacturers specifications, high voltage output accuracy may be compromised without a means to compensate for this temperature-induced variation.

In some embodiments, a means to measure temperature and provide that information to the controller 102 may be provided. In different embodiments, an electronic temperature sensor 352 such as a thermistor, thermocouple or active temperature measurement device such as the Analog Devices AD590 may be utilized as the sensing element.

This temperature information may be provided to the microcontroller 410 through the A/D conversion of the analog signal from the temperature sensor 352. With the temperature of the KV sense resistor 616 known, the microcontroller 410 can calculate an adjustment to the control loop and alter the drive to the resonant converter 608 to compensate for the change in divide ratio and maintain the high voltage at a constant value independent of temperature. These calculations may be based on manufacturers' specifications on how the divide ratio changes with temperature, and/or based on information acquired during calibration of the invention by measurement of high voltage performance across temperature, measurement of the divide ratio variation with temperature, or both.

1.10 X-Ray Tube Beam Deflection

For some applications, it may be desirable to deflect the x-ray tube electron beam. There are several applications where the ability to deflect the beam provides significant advantages, including those described in the following examples.

In some embodiments, due to mechanical tolerances of components, assembly techniques and other factors, the location that the electron beam impinges on the x-ray tube target can vary from tube to tube. This can result in device-to-device variation in x-ray output due to the variability of the electron beam location on the tube 306. In extreme cases, it may result in x-ray tubes being rejected for not meeting output specifications and thereby reducing manufacturing yields and increasing unit cost. The ability to deflect the beam allows a means to overcome variations in initial beam location on the target by allowing for adjustment of the beam to a target location that results in the desired x-ray output. This ability to adjust the beam results in improved consistency of x-ray output across devices, improving yields and lowering cost.

In some embodiments, it may be desirable to utilize beam scanning as a means of mapping out the spatial x-ray emission characteristics of the x-ray tube 306, and in particular the x-ray target in the tube. In this approach, the electron beam may be scanned in some defined manner across an area of the target. At each position in the scan, a suitable x-ray detector may monitor some characteristic of the x-ray output such as energy, spectrum or flux. In this manner, a map of the x-ray tube emission characteristics across the face of the target as a function of electron beam position on the target can be established. Such monitoring and mapping may have application in areas of x-ray tube quality control, or to permit x-ray output optimization by operating the tube 306 with the beam positioned on a particular area of the target to achieve the desired output characteristics.

In another embodiment, it may be desirable to utilize beam scanning to position the beam on the target in a desired position relative to external filters, collimators or other devices to permit selective conditioning of the output beam. In one possible application, a small block of tungsten or similar material used for radiation shielding is placed over the front of the tube 306. Small collimator holes passing through the tungsten block allow x-rays to pass through only when the electron beam is positioned on the target in line with the axis of a particular collimator hole. By varying the location of the beam on the target, the x-ray output can be selectively directed to one of the collimator holes. These holes can also contain x-ray filters or other beam conditioning devices, providing a means to selectively condition some parameter of the x-ray output emission.

In another embodiment, an x-ray tube 306 with an internal target comprised of different materials delineated in some manner across the face of the target may be used. Characteristic x-ray emission, and in particular certain spectral emission lines in the x-ray output energy spectrum are related to the specific target material upon which the electron beam impinges.

The ability to deflect the electron beam onto different areas of this target enables the ability to change the x-ray output energy spectrum of the x-ray tube 306. This ability to change the spectrum, and in particular the locations of the characteristic spectral lines in the spectrum, without the need for external hardware, filters and related mechanical complexity has advantage in certain x-ray fluorescence applications to aid in materials analysis and identification.

In another embodiment, it may be desirable to modulate the intensity of the x-ray output. An x-ray tube 306 may have a target material that has a thickness which varies in some manner, either continuously or in discreet steps across the face of the target. Deflecting the beam across this target would result in a variation in x-ray intensity depending on the target thickness at the point where the electron beam impinges. In an extreme case, an area of the target can be made radio-opaque such that no x-rays are produced. Thus a means to terminate x-ray emission from the tube 306 by deflecting the beam onto this target area can be realized. Alternatively, the electron beam may be caused to deflect sufficiently to strike the internal sidewalls of the x-ray tube 306 to essentially terminate x-ray production in certain x-ray tube embodiments.

Use of beam deflection as a means of x-ray output intensity modulation has important advantages over the method whereby the filament temperature is varied to modulate the flux in the electron beam, and thereby modulate the x-ray emission intensity. The filament has an inherent thermal time constant based in part on filament wire diameter, length and the specific configuration of some number of coiled turns, or a hairpin bend (common filament configurations). This thermal time constant sets an upper limit on the modulation rate and creates a tradeoff between use of small diameter filament wire to achieve a short thermal time constant and fast modulation response, and a larger diameter filament wire for longer lifetime but with a longer thermal time constant and slower dynamic response. In addition, cycling the filament temperature induces temporally varying thermal stresses in the filament material which may lead to premature failure.

Use of a beam deflection approach to intensity modulation avoids these problems. The filament temperature, and consequently the electron beam flux may be held constant, and instead the beam may be deflected to different areas of the target to achieve different x-ray output emission levels. Beam deflection can be made to occur at significantly higher rates; thus the x-ray output can be made to vary more rapidly than through the filament temperature modulation approach, and avoids the trade-off between filament wire diameter and thermal time constant.

In another embodiment, it may be desirable to implement beam deflection to compensate for electron beam wander over the face of the target. In certain instances, due to inherent characteristics and behavior of the x-ray tube 306, the electron beam may not remain at a fixed position, but may wander about the target face in an uncontrolled manner. This wander can result in undesirable variations in x-ray output emission characteristics. Incorporation of an active means of controlling beam position, whereby the instantaneous position of the electron beam on the target is detected, and this information fed back into circuitry that adjusts the beam position to compensate for the beam wander, can be used to maintain the beam at a fixed and stable location on the target.

Figure 14:
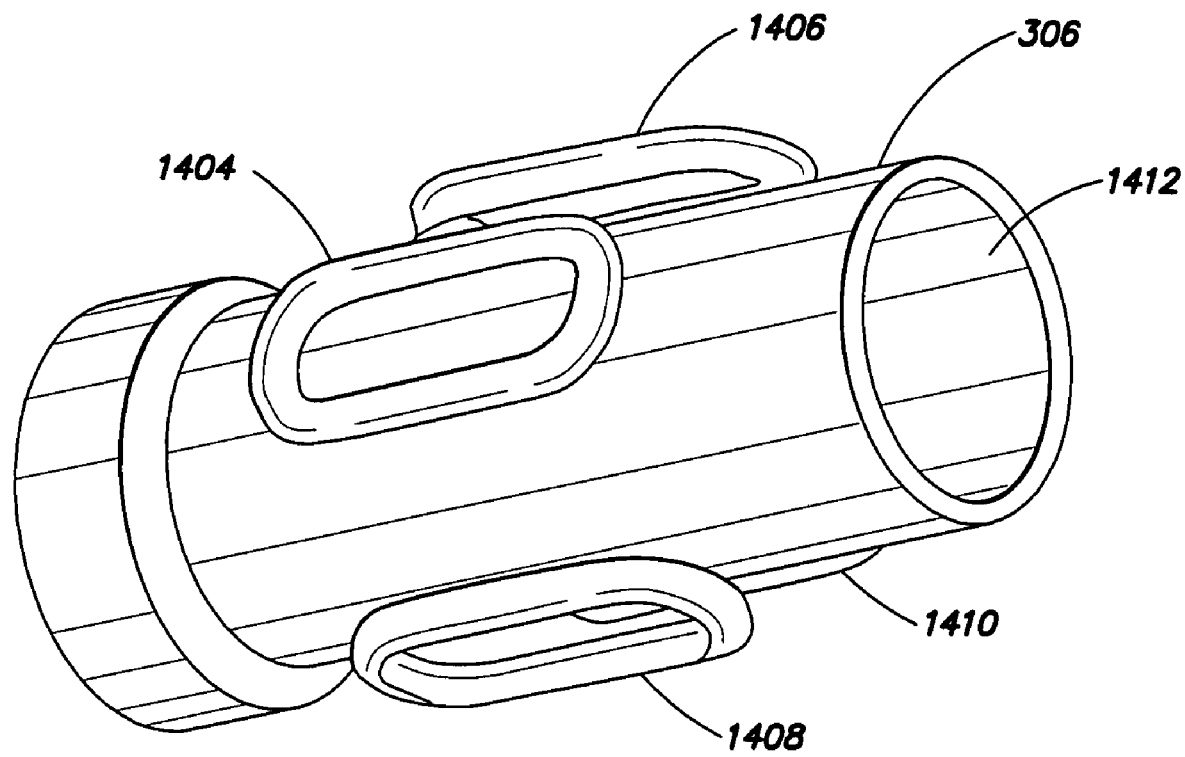
FIG. 14 is a perspective view of an example of an x-ray tube including a plurality of deflection coils.

FIG. 14 is a diagram illustrating an x-ray tube 306 including a plurality of deflection coils 1404, 1406, 1408 and 1410. To implement beam deflection, in some embodiments, four deflection coils 1404, 1406, 1408 and 1410 may be positioned 90 degrees apart around the tube 306 as shown in FIG. 14. Opposing coils (e.g., 1404 and 1410, and 1406 and 1408, respectively) may be paired and wired in series, operating in conjunction to provide deflection in each of the X and Y axes respectively. A variable DC current may be passed through the coils 1404, 1406, 1408 and 1410 to create a magnetic field through the x-ray tube 306. The interaction of this magnetic field with the electron beam may result in a deflection of the beam as it passes through the field. By varying the magnitude of the current passing through the coils 1404, 1406, 1408 and 1410, the magnitude of the magnetic field, and the resulting electron beam deflection and position of impact on the target can be made to vary. Reversing the direction of the current flowing through a pair of coils results in a reversal of beam deflection direction. In this manner, both positive and negative deflections of varying magnitude along an axis may be realized. Use of two pairs of coils oriented at 90 degrees to one another results in the ability to independently deflect the electron beam along two orthogonal axes, X and Y. This allows complete positional control of the beam across the face of the target, and allows the beam to be scanned in any arbitrary manner or pattern.

Four coils arranged in orthogonal pairs (e.g., 1404 and 1410, and 1406 and 1408, respectively) may be utilized to achieve independent control of electron beam deflection along mutually perpendicular axes. In another embodiment, three coils may be utilized, preferably arranged at 120 degrees apart around the x-ray tube 306. This configuration has the potential advantages of reducing the packaging size and cost, which may be important in some applications. Because of this coil arrangement, electron beam deflection requires all three coils to participate; that is, beam position is dependent on the magnetic field contributions of all three coils. Algorithms may be configured to establish the required magnitude and direction of currents flowing in each coil, with this information being used to control the deflection coil drive electronics in order to control the position of the electron beam on the target.

Figure 15:
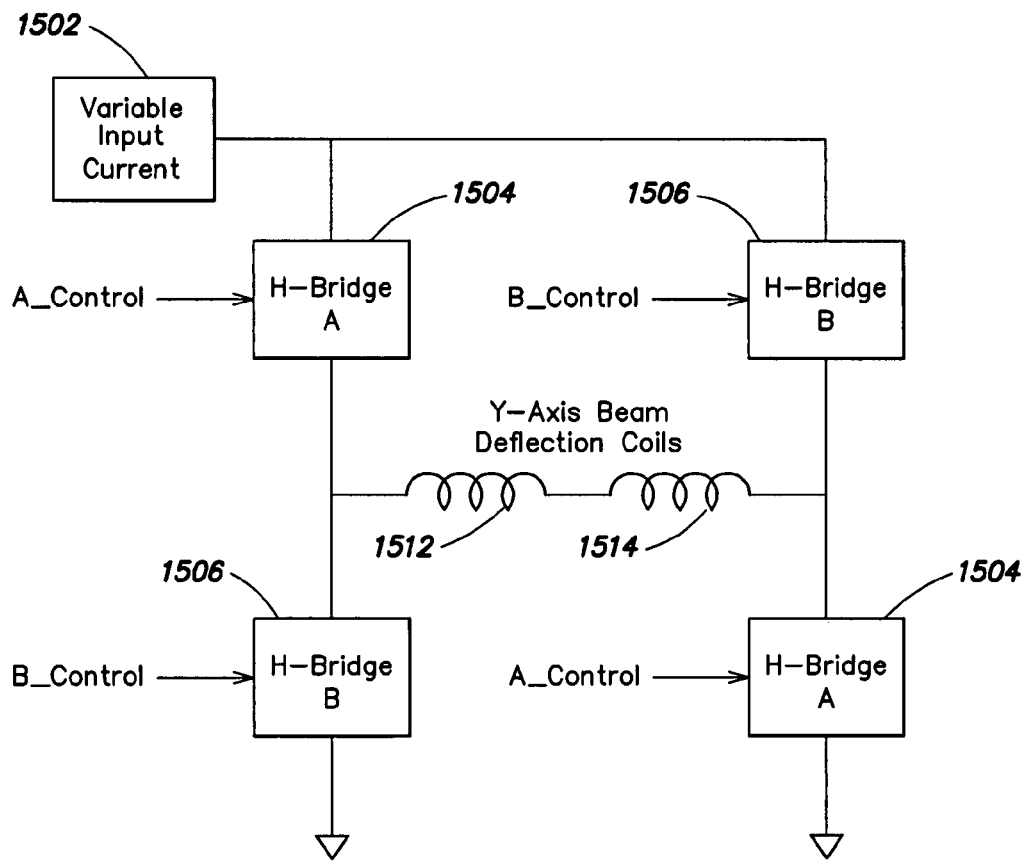
FIG. 15 is a circuit diagram illustrating an example of a system for driving deflection coils using an H-bridge configuration.
Figure 16:
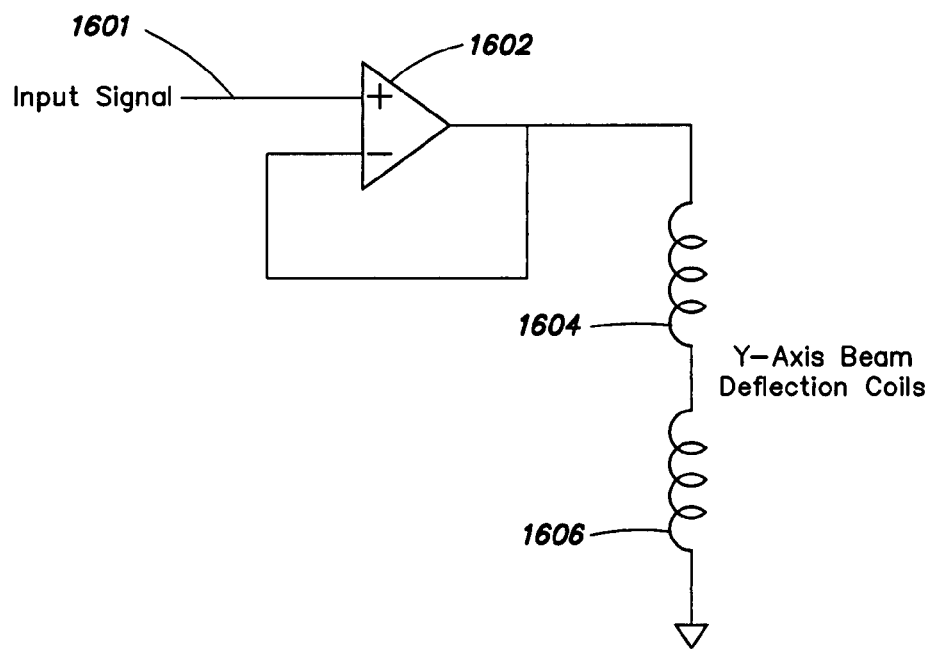
FIG. 16 is a circuit diagram illustrating an example of a circuit for driving deflection coils using a power operational amplifier.

FIGS. 15 and 16 depict two possible embodiments of means to drive the deflection coils. FIG. 15 is a circuit diagram illustrating an example of a system for driving deflection coils using an H-bridge configuration. In FIG. 15, the H-bridge configuration is a standard means of reversing current flow through a device, in this case the deflection coils 1512 and 1514, located in the middle of the bridge. H-Bridge blocks A 1504 and B 1506 are switches which are opened or closed based on the A_Control and B_Control signals. Blocks A and B are turned on and off alternately, such that when the switches in blocks A are open, the switches in blocks B are closed. This results in current flowing through the coils 1512 and 1514 from right to left in the FIG. 3. Closing the A switches and opening the B switches result in current flow through the coils 1512 and 1514 from left to right. In this manner, the polarity of the magnetic field induced through the x-ray tube 306 can be reversed. The amplitude of the field can be adjusted by varying the input current which feeds the top of the H-bridge.

FIG. 16 is a circuit diagram illustrating an example of a circuit for driving deflection coils using a power operational amplifier 1602. In FIG. 16, a power op amp 1602, or an op amp and suitable power output driver, may be used to drive the deflection coils 1604 and 1606 directly. The bipolar output 1603 from the op amp 1602 results in the ability to reverse the direction of current flow in the coils 1604 and 1606 without the need for additional switches. Since the op amp output 1603 is proportional to the input signal 1601, the magnitude of the current flowing through the coils 1604 and 1606 can be varied based on the input signal in order to adjust the magnitude of the resultant magnetic field.

1.10.1 Beam Deflection—Closed Loop Control

To achieve a high degree of positional accuracy, closed loop control of the beam output may be performed. This closed loop control requires knowledge of the position of the electron beam on the target, such that an error signal between the desired and actual position can be established.

Once established, a standard PID control loop or some other control loop architecture based on this error signal, similar to architectures discussed elsewhere in this document including non-linear and multivariate can be implemented in the controller 102 to set and maintain the beam at the desired location.

An important consideration for closed loop control is in establishing the actual position of the electron beam on the target. This can be accomplished as follows. In one approach, a calibration curve is established a priori. That is, during a calibration test, using appropriate external equipment, the relationship of the position of electron beam on the target and the corresponding electrical current necessary to drive the deflection coils to achieve that position may be established. This information can be stored in system memory. In operation, the controller 102 may monitor the current flowing through the deflection coils, and use that information to infer the electron beam location on the target. Closed loop control of the deflection coil current thus may be implemented to control the beam position on the target.

This general approach is depicted in FIG. 3, where the control signals X_AXIS_POS and Y_AXIS_POS control signals 330 and 334 may be generated by the controller 102 to set the beam position on the target. Feedback signals X_DEFL_FDBK 370 and Y_DEFL_FDBK 372 may provide information to the controller 102 on the deflection coil current, and therefore, through the use of calibration data, an indirect indication of the actual electron beam position.

One implication of this first approach is that it assumes that that the calibrated relationship between beam position on the target and the deflection coil drive current remains constant. This may not necessarily be true long term, as over time, the accuracy of this calibration data may be lost as the characteristics of the physical hardware change due to component aging or other effects. A second approach is described which overcomes this difficulty, and permits calibration to be maintained for the life of the system.

This second approach relies on the use of an x-ray detector responsive to x-ray output. In this approach, the electron beam may be scanned across the target such that it falls off the edge of the target on either side, causing a change in x-ray emission that is sensed by the x-ray detector when it does. The x-ray detector may be located either outside of the x-ray tube or within the tube, where in either case it would monitor backscattered x rays from the target in the tube. By monitoring the detector output as the beam is scanned, the edges of the target can be located. The corresponding deflection coil currents then may be noted at each target edge. Thus, with the deflection and the corresponding deflection coil current known at two points, a relationship between them, typically linear, can be established. This relationship can be used during subsequent operation of the system, in conjunction with monitoring the deflection coil current to establish the location of the electron beam on the target. In essence, a calibration of electron beam position on the target and deflection coil current may be performed. Because this approach relies on input from an x-ray detector that in some embodiments may be part of the total x-ray module, this calibration can be performed on an as-needed basis. That is, the overall system may be self-calibrating. This is in contrast to the first approach, which may require a separate calibration test to be performed, with the resulting calibration data coded into software.

Calibration in two axes may be performed as follows. First, the electron beam may be scanned along the X-axis to find both edges of the target, as indicated by an x-ray detector. The midpoint of the scan may be established as the average value of the deflection coil currents at both edges of the target. For circular targets, this establishes a point on the diameter of the target along the Y-axis. With the X-axis deflection coil current set to this average midpoint value, the Y-axis deflection coil then may be scanned to find the edges of the target along the Y-axis. The midpoint of this scan, which may be based on the average values of the Y-axis deflection coil currents measured at each edge of the target, may be calculated to establish the midpoint of the center of the target. With the Y-axis deflection coil current set to the average value to position the beam at the midpoint of the Y-axis, the X-axis then may be scanned a second time to again establish the edges of the target. The average of the deflection coil currents as measured at each target edge along the X-axis may establish the midpoint of the X-axis deflection. Thus, the center of the target, and the X and Y axis deflection scale factors as a function of deflection coil current, may be established. This data subsequently may be used to set the beam to a specific point on the target, and to use closed loop control on the deflection coil currents to maintain the electron beam at this target position.

Figure 17A:
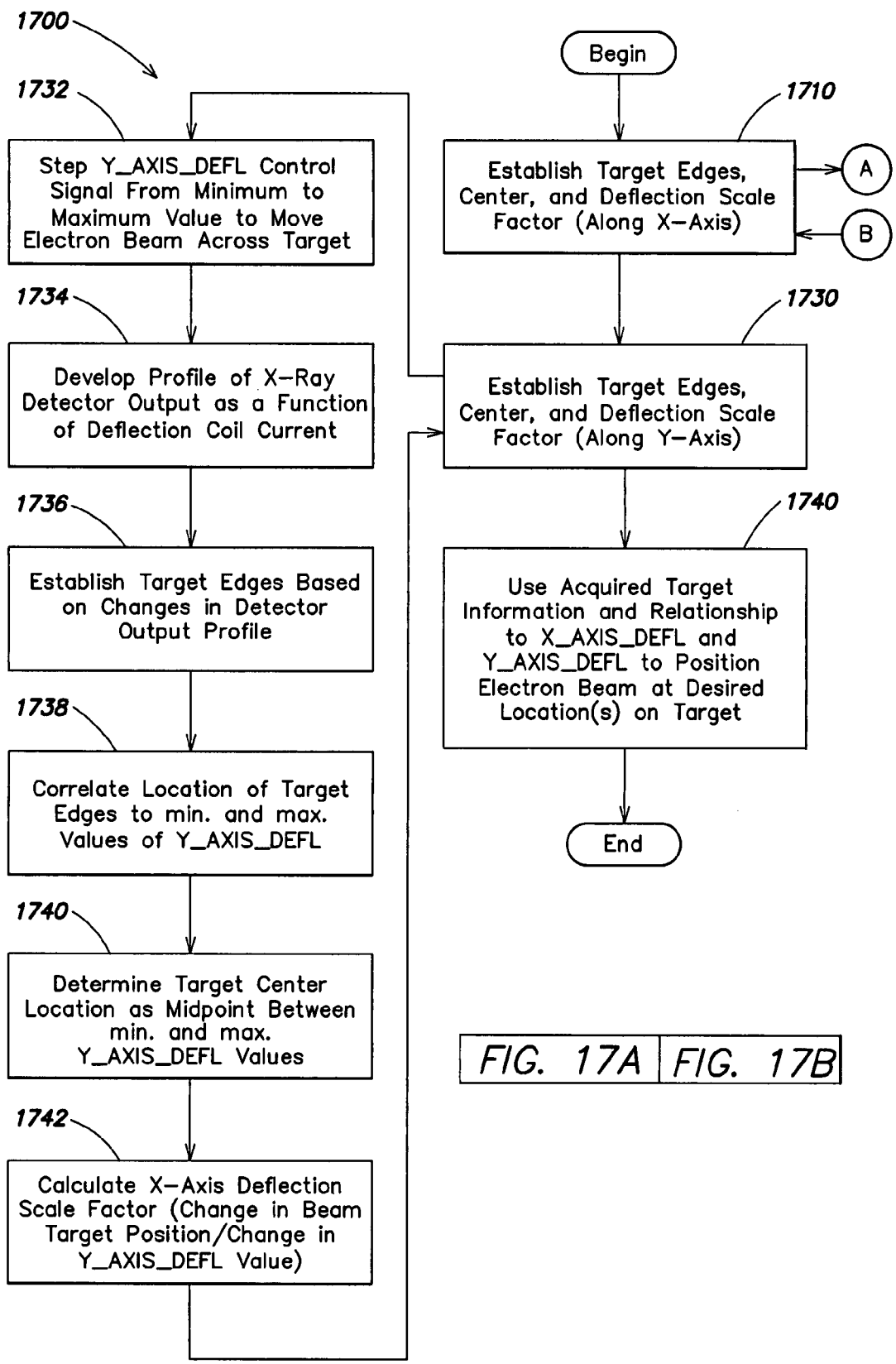
FIG. 17 is a flow chart illustrating an example of a method of implementing beam deflection control.
Figure 17B:
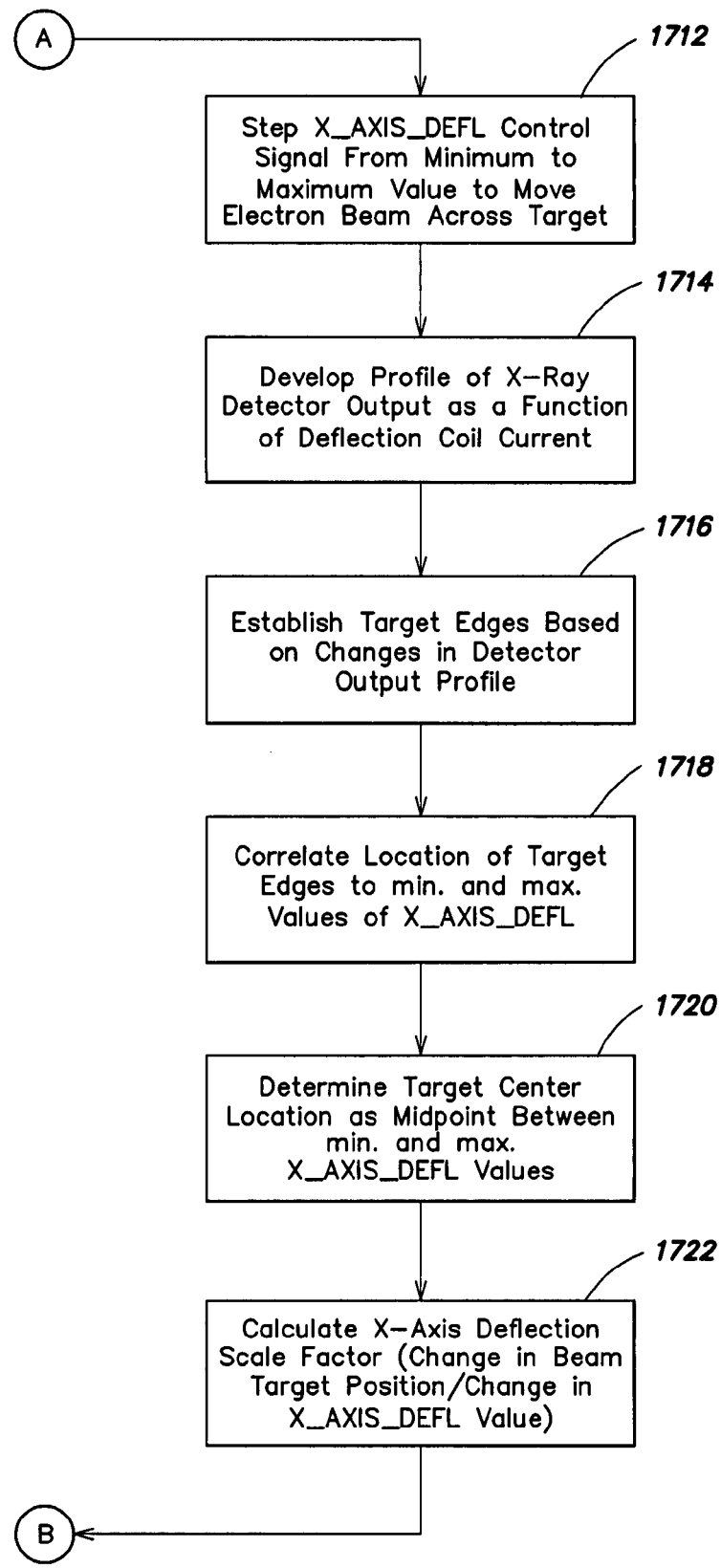

Beam deflection control may be implemented as shown in FIG. 17. FIG. 17 is a flow chart that illustrates an example of a method 1700 for implementing beam deflection control, for example, as part of step 716. In step 1710, the target edges, center and deflection scale factor along the X-axis are determined. Step 17 is detailed in substeps 1712-1722. In substep 1712, an X-axis deflection control signal is stepped from minimum to maximum value to move the electron beam across the target. In substep 1714, a profile of the x-ray detector output as a function of deflection coil current is determined. In substep 1716, target edges are established based on changes in the detector output profile. In substep 1718, the locations of the target edges are correlated to minimum and maximum values of the X-axis deflection control signal. In substep 1720, the target center location is determined as the midpoint between the minimum and maximum X-axis deflection control signal values. In substep 1722, the X-axis deflection scale factor is calculated as the ratio of the change in beam target position to change in X-axis deflection control signal value. In step 1730, the target edges, center and deflection scale factor are established along the X-axis. Substeps 1732-1742 of step 1730 correspond to substeps 1712-1722, respectively, with the X-axis replaced by the Y-axis. In step 1740, the acquired target information and the relationship to the X-axis deflection control signal and the Y-axis deflection control signal are used to position the electron beam at a desired location on the target in the X-ray tube.

1.10.2 Beam Deflection—Passive Implementation

In certain embodiments, an active beam deflection control system as described above may not be used. Alternatively, positioning the beam at a specific target location and maintaining it there on a permanent basis may be adequate. In such embodiments, a permanent magnet may be used as a passive means of inducing beam deflection.

In some embodiments, a small permanent magnet may be placed in proximity to the x-ray tube 306 in order to induce a magnetic field within the x-ray tube 306, oriented in such a manner as to cause the electron beam to deflect as it passes through the field. The amount of deflection may be dependent on any of a variety of variables, including any of: the strength of the field, the length of interaction between the field and the electron beam or a combination thereof. The resultant angle deflection of the electron beam also may depend on the electron beam accelerating voltage, which may cause the electron beam to change position on the target as the accelerating voltage is changed. Thus, this passive approach may provide maximum benefit in applications where the electron beam is operated at a fixed accelerating voltage, or in embodiments where it is desired to scan or otherwise move the beam to a different target position as a function of accelerating voltage.

The electron beam produced in an x-ray tube 306 may not hit the target at an acceptable location due to mechanical and assembly tolerances during x-ray tube manufacture. Such inaccuracy may be sufficient cause to reject the x-ray tube 306, which has an overall negative effect on production yield and cost. Accordingly, in some embodiments, a magnet may be used to induce sufficient deflection in the beam to cause it to hit the target at an acceptable position, thereby permitting an x-ray tube 306 that would otherwise be rejected to be utilized.

1.11 Electron Beam Position—Active Position Sensing

The previously discussed approaches to sensing beam position use a calibration procedure performed between beam position and deflection coil drive signals to establish the relationship between these two parameters. One implication of this approach is that it is performed in advance of actual tube operation, which in some applications may not be desirable.

Another implication to relying on a calibration process based on deflection coil current to establish beam position is that closed-loop control systems used to set and maintain beam position cannot compensate for changes in position due to influences other than those induced by deflection coils. For example, it has been observed that in some x-ray tubes, the electron beam exhibits random fluctuation of beam position due to inherent characteristics of the tube; that is, the beam position is not constant with time. Thus, even with a closed loop control system maintaining deflection coil current at a steady value, the beam position may change.

Another technique for establishing beam position which has the ability to directly detect the actual beam location on the target will now be described. This ability to directly sense beam position may result in significantly improved accuracy and stability over closed-loop control approaches that rely on calibration curves or other indirect means to establish beam position.

Using this technique, multiple x-ray detectors, such as PIN diodes may be arranged around the circumference of the x-ray tube 306 such that they are each responsive to the x-ray emission. With the electron beam initially in a known position, the output signals from each detector may be recorded. Changes in the position of the electron beam on the target result in the electron beam moving closer to some detectors and farther from others, causing some detector signals to correspondingly increase and others to decrease in response.

If the x-ray tube output remains constant, the value of the sum total of all detector signals may remain constant even though the individual detector signals might change in response to changes in electron beam position. Changes in the total x-ray output may affect all detector signals, causing the value of the sum of the detector signals to increase or decrease in response. By considering changes in individual detector signals, and of the sum total of all the signals, a means for distinguishing changes in electron beam position from changes in x-ray output intensity can be established.

Since the actual electron beam position on the target can be determined in real time using this approach, it allows a means for implementation of electron beam position control and/or position stabilization to be achieved.

Figure 18:
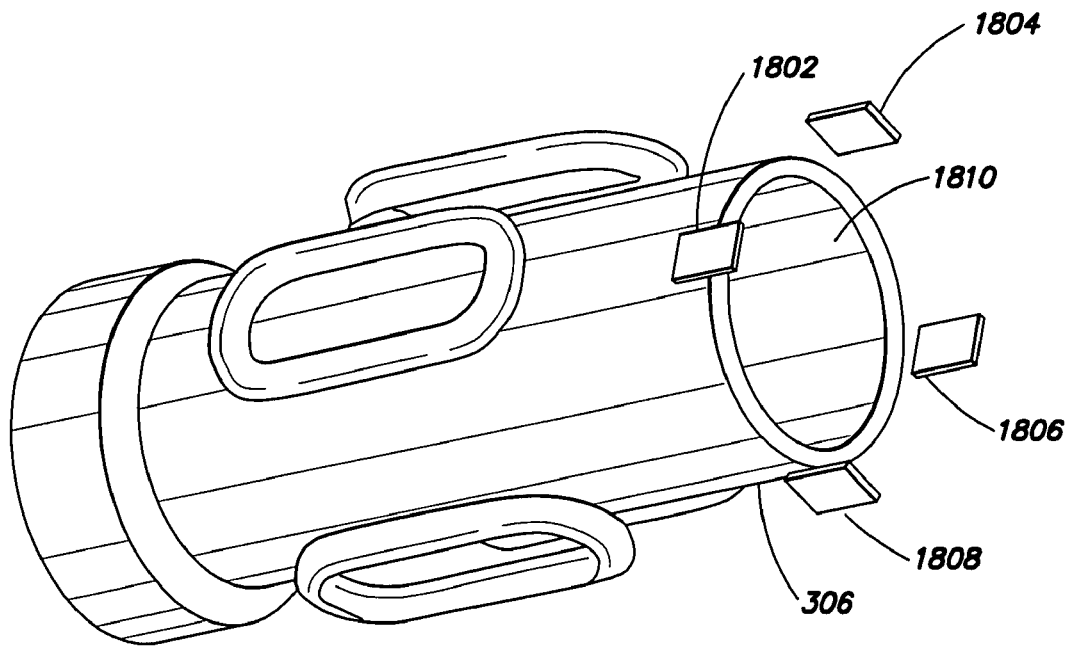
FIG. 18 is a perspective view of an example of an x-ray tube having detectors positioned forward of an x-ray output window.
Figure 19:
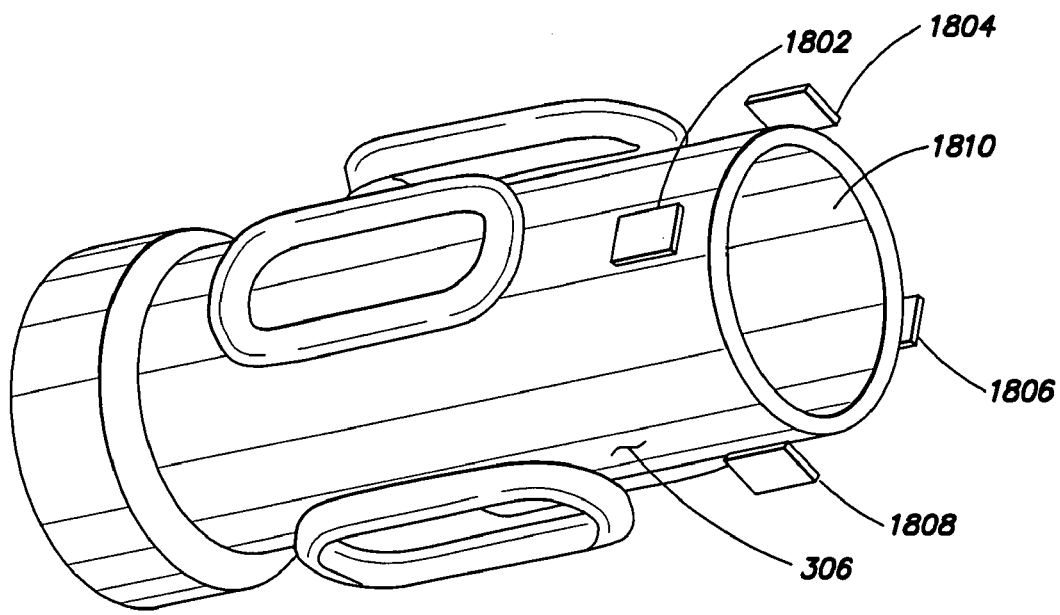
FIG. 19 is a perspective view of an example of an x-ray tube including detectors positioned behind an x-ray output window.

In some embodiments of this approach, four x-ray sensitive detectors may be arranged in orthogonal pairs around the circumference of the x-ray tube anode, with their active surfaces oriented such that they are each responsive to the x-ray emission as shown in FIGS. 18 and 19.

FIG. 18 is a diagram illustrating an example of an x-ray tube 306 having detectors 1802, 1804, 1806 and 1808 positioned forward of x-ray output window 810. In other embodiments, the detectors 1802, 1804, 1808 and 1810 may be located behind the window 1810 as shown in FIG. 19.

FIG. 19 is a block diagram illustrating an example of an x-ray tube 306 including detectors 1802, 1804, 1806 and 1808 positioned behind x-ray output window 1810. In such embodiments, the detectors may detect backscattered radiation from the target window. Optionally, the detectors may be aligned along the same axes as four deflection coils, also arranged pair wise along orthogonal axes around the x-ray tube 306 to establish X and Y deflection axes, but other arrangements are also possible. Opposing detectors may be aligned along the X-axis of associated X-axis deflection coils, and the other two detectors may be aligned along the Y-axis. FIG. 3 depicts this arrangement, whereby two opposing Y-axis deflection sensors 358 and 359 are shown at the output end of the x-ray tube 306. Each of the four detector signals may be acquired by the controller 102, which may perform the following computations and develop appropriate drive signals to the deflection coils to maintain the electron beam at the desired position. In alternative embodiments, these computations may be performed by dedicated hardware, firmware, or a combination thereof, possibly in combination with software.

The sum value of all four detectors may be defined as:

$$Det\_sum = X1 + X2 + Y1 + Y2$$

where $X1$=output signal from X-axis detector along positive X-axis $X2$=output signal from X-axis detector along negative X-axis $Y1$=output signal from Y-axis detector along positive Y-axis $Y2$=output signal from Y-axis detector along negative Y-axis The normalized X-axis and Y axis positions of the electron beam on the target may be defined as:

$$X\_pos = C1*(X1-X2)/Det\_Sum$$

$$Y\_pos = C2*(Y1-Y2)/Det\_Sum$$

Where C1 and C2 are generalized scale factors used to convert detector signals into units of displacement or other useful parameter.

If the electron beam moves off of the target along the positive X-axis, the X1 detector signal may increase by an amount $\Delta X$ and the X2 detector signal may decrease by a similar amount. The Y-axis detector output signals may remain constant. Thus, the change in electron beam position along the X-axis may be defined as:

$$\Delta X\_pos = \text{Final Position} - \text{Initial Position}$$

$$\Delta X\_pos = \text{Final Position} - \text{Initial Position}$$

$$\text{Final Position} = [(X1+\Delta X)-(X2-\Delta X)]/Det\_Sum$$

$$\text{Initial Position} = (X1-X2)/Det\_Sum$$

Therefore, the change in position may be defined as:

$$\text{Change in Position} = \text{Final Position} - \text{Initial Position}$$

or $$\Delta X\_pos = (2*\Delta X)/Det\_Sum$$

This signal, $\Delta X\_pos$ may then be utilized to drive the control circuitry for the X-axis deflection coil to induce a change to the coil current to null this signal, resulting in the electron beam being repositioned to the desired location.

Other embodiments of this approach are envisioned, including those with a different number of detectors, incorporation of additional detector signal conditioning including gain and offset correction, software algorithms to account for other error effects including non-uniformities in the x-ray output beam and cross-coupling between detector channels along X and Y axes, or any suitable combination thereof. Different embodiments may implement one or more of this approach, including computation of the change in electron beam X and Y axis position, using software, firmware, hardware or any suitable combination thereof.

Figure 20A:
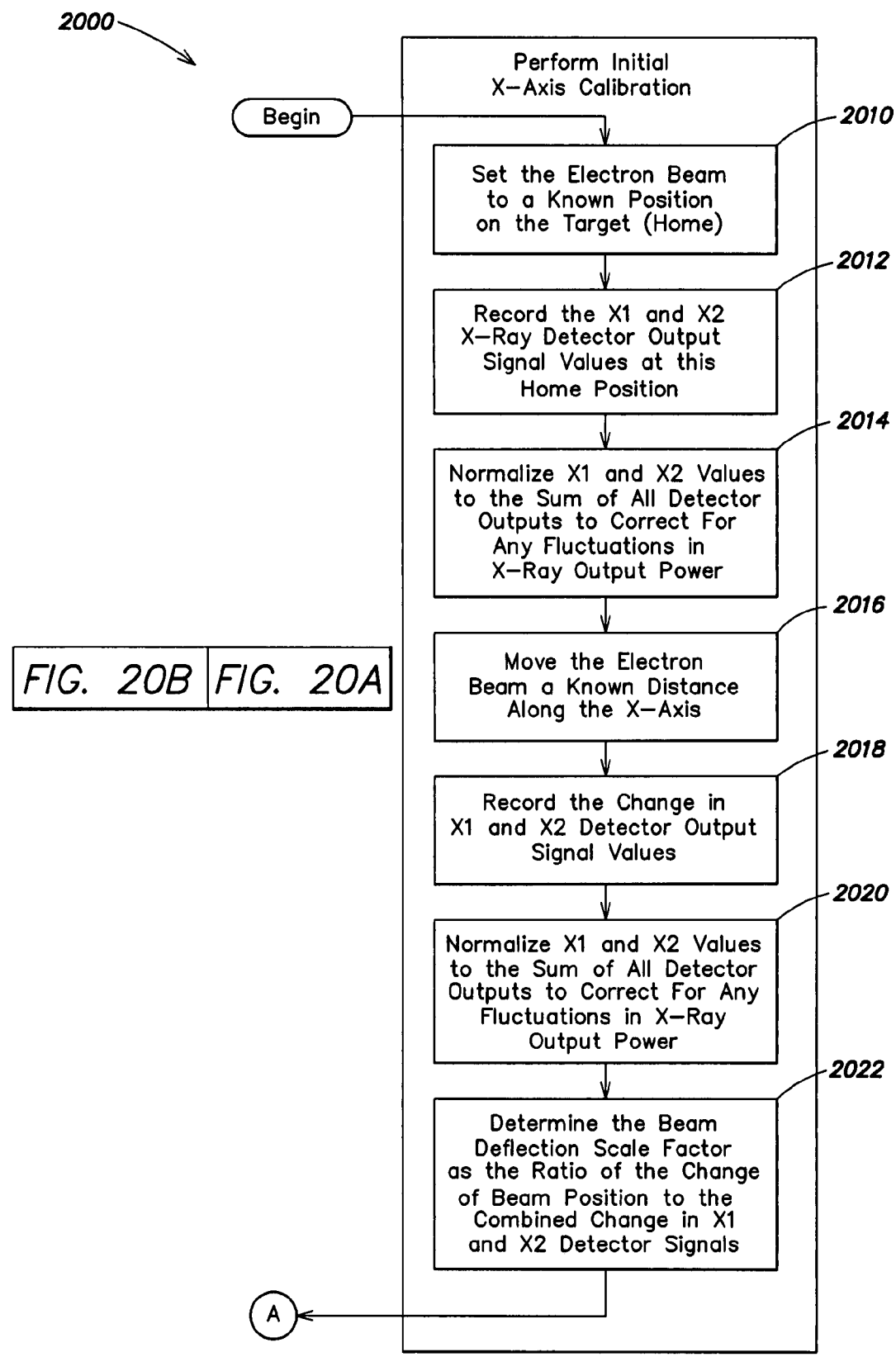
FIG. 20 is a flow chart illustrating an example of a method of implementing electron beam position active position sensing.
Figure 20B:
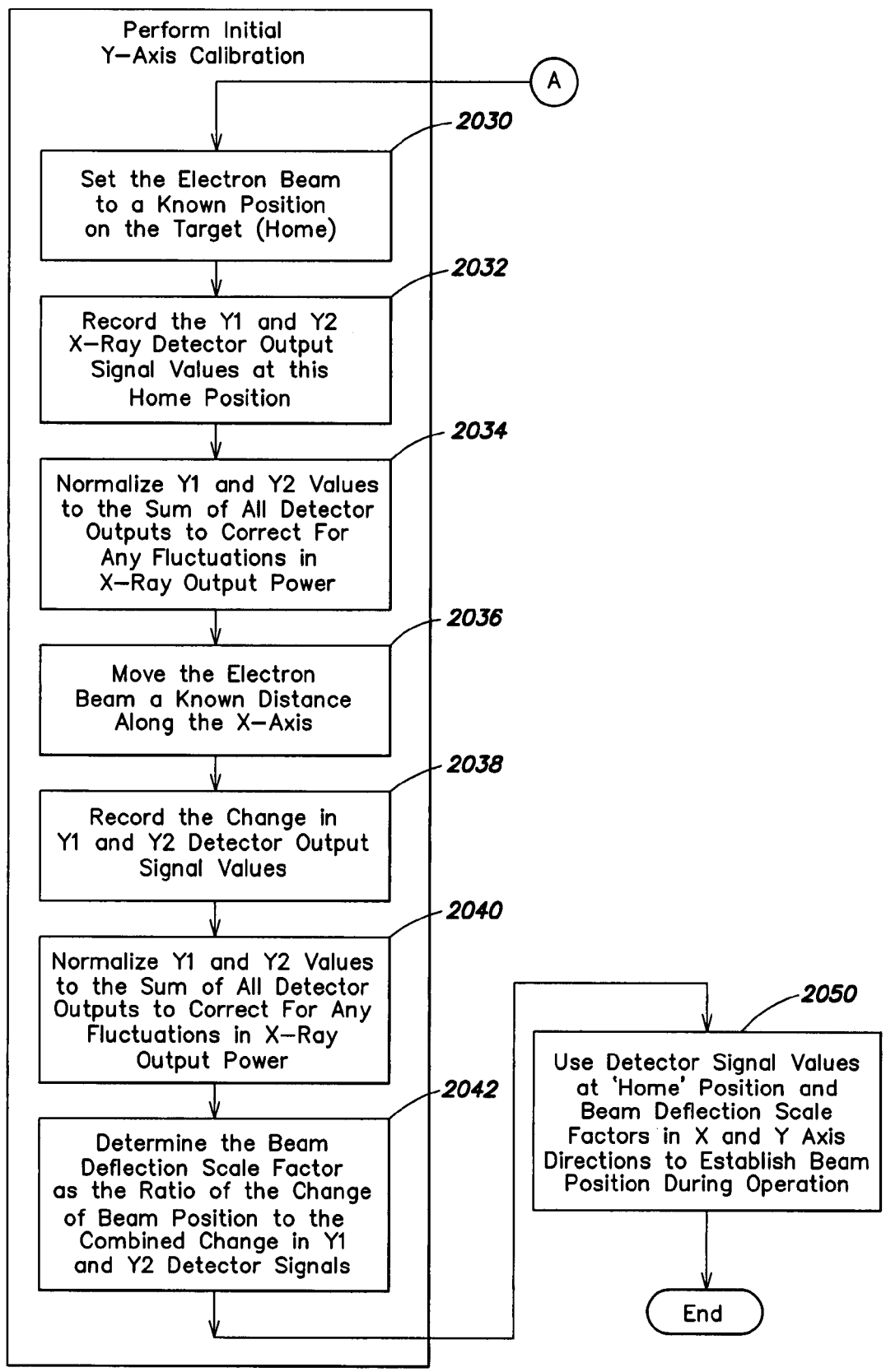

Electron beam position active position sensing may be performed as illustrated in FIG. 20. FIG. 20 is a flow chart that illustrates an example of a method 2000 for implementing electron beam position active position sensing, for example, as part of step 718. In step 2010, the electron beam is set to a known home position on the target. In step 2012, the X1 and X2 x-ray detector output signal values are recorded at the home position. In step 2014, the X1 and X2 detector output signal values are normalized to the sum of all detector outputs to correct for fluctuations in x-ray output power. In step 2016, the electron beam is moved a known distance along the X-axis. In step 2018, the change in X1 and X2 detector output signal values is recorded. In step 2020, the new X1 and X2 detector output signal values are normalized to the sum of all detector outputs to correct for fluctuations in x-ray output power. In step 2022, the beam deflection scale factor is determined as the ratio of the change of beam position to the combined change in X1 and X2 detector signals. Steps 2010-2022 are involved in initial X-axis calibration. Steps 2030-2042 for initial Y-axis calibration correspond to steps 2010-2022, respectively. In step 2050, the detector signal values at the home position and the beam deflection scale factors in the X-axis and Y-axis directions are used to establish beam position during operation.

1.12 X-Ray Module Networking Capability

In some embodiments, multiple x-ray modules may be connected together in a network or array such that their individual x-ray outputs combine to provide a field of x-radiation with characteristics that are not achievable through use of a single module. Example characteristics include a radiation field that is larger, more intense, more uniform, at multiple energy levels, or possibly a modulated x-ray field on top of a steady state background x-radiation level. Some embodiments may utilize multiple x-ray modules for security purposes, or for redundant or fault tolerant operation. In these embodiments, it may be desirable for modules to communicate with one another for integrated autonomous control and data exchange purposes. In other embodiments, multiple x-ray modules may be connected together in a network, but instead of being physically arranged in an array where their outputs combine in some manner as described previously, the modules may be separated and operated independently. This networked arrangement could have utility in a manufacturing operation, where individual x-ray modules may be located at different locations in the operation, such as at quality control inspection stations on an assembly line, or at incoming inspection for inspection of incoming materials.

Figure 21:
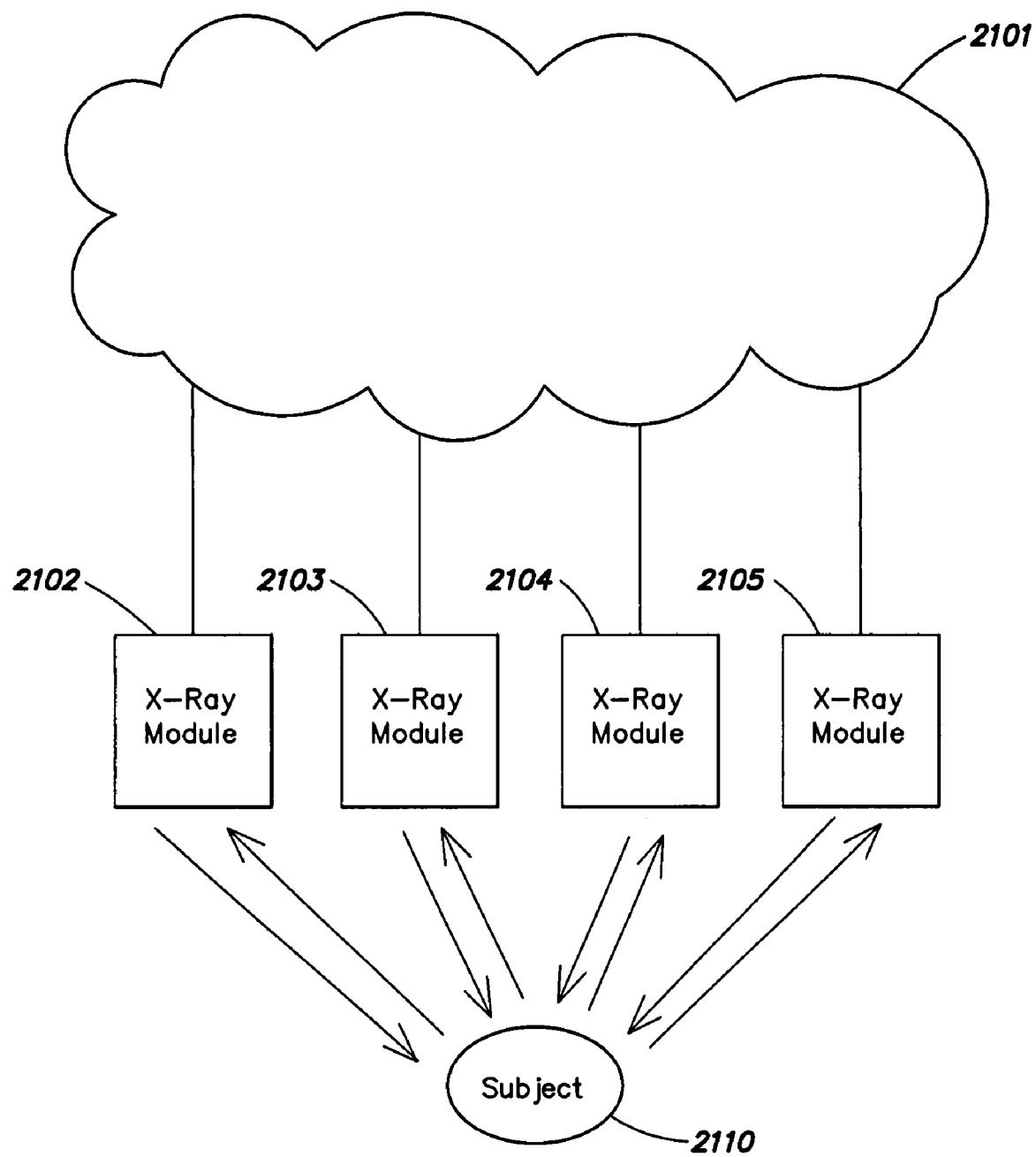
FIG. 21 is a block diagram illustrating an example of an array of interconnected x-ray modules.

FIG. 21 is a block diagram illustrating an example of a plurality (e.g., an array) of x-ray modules 2102-2105 interconnected as part of a network 2102. Two or more of the x-ray modules 2102-2105 may be configured to irradiate a subject 2110 and/or detect x-rays from one or more of the x-ray modules and/or the subject 2110. As used herein, a "network" is a group of two or more components interconnected by one or more segments of transmission media on which communications may be exchanged between the components. Each segment may be any of a plurality of types of transmission media, including one or more electrical or optical wires or cables made of metal and/or optical fiber, air (e.g., using wireless transmission over carrier waves) or any combination of these transmission media. As used herein, "plurality" means two or more. It should be appreciated that a network may be as simple as two components connected by a single wire, bus, wireless connection or other type of segments. Further, it should be appreciated that when a network is illustrated in a drawing of this application as being connected to an element in the drawing, the connected element itself is considered part of the network.

In some embodiments, a communications port and associated software may be provided and used to communicate with other x-ray modules connected to one another in an integrated network. The controller 102 may be configured to transmit and/or receive status and control information between modules. In this mode of operation, each module may be provided with a unique identifier to distinguish it from others connected to the network. In this manner, data packets can be transmitted along the network and received by the module for which it was specifically intended. Other means of accessing individual modules, including use of hardware control or enable lines is also possible.

1.12.1 Master—Slave Operation

In multiple module configurations, it may be desirable for one of the modules to assume the responsibility of supervising and coordinating the other modules in a typical master-slave configuration. In this operational mode, one module, designated the master communicates with the other modules in the network and functions as the overall supervisor. In this role, the master issues commands to the slave modules which respond accordingly. Data exchanged between modules may be used by the master to monitor and confirm proper operation, and by the slave to adjust x-ray output based on input commands from the master.

1.12.2 External Host Operation

In other multiple module configurations, it may be desirable for a separate, external host computer to be connected to the network of modules. In this configuration, the individual modules in the network may communicate with and be controlled by the external host. Thus, all modules function in a slave mode to the external host which functions as the master. This network configuration allows an external host to perform overall control and coordination of the operation of each networked module.

1.13 Automatic Identification

In some embodiments, where the low voltage control components, including the microcontroller 410, may be connected to the encapsulated high voltage power supply 620 and x-ray tube assembly through a detachable electrical cable, it may be desirable for the microcontroller 410 to be able to automatically and uniquely identify the encapsulated assembly, or in the case where the x-ray tube 306 is encapsulated independently from the high voltage power supply 620, to identify either or both of these components.

This automatic identification ability enables the microcontroller 410 to customize, configure or otherwise adapt its performance or behavior to the specific encapsulated assembly. Information such as calibration data, control loop parameters such as PID control constants, fault history, and usage and operating history can be maintained by identification number in non-volatile system memory and be stored and subsequently recalled based on the unique identification code established for each assembly.

In some embodiments, a unique digital identifier that can be read by a controller 102 is provided in the encapsulated module. Several means of accomplishing this are possible, including use of DIP switches in the encapsulated module to set a value in an on-board data register to a unique value prior to encapsulation, that can subsequently be read by the controller 102.

In some embodiments, a serial number identification component, such as the Maxim (Dallas Semiconductor) DS1990A Serial Number iButton may be employed. This component is purchased with a unique serial number identifier permanently stored within the device. This device may be packaged with the x-ray tube 306 and high voltage power supply 620, and may communicate with the controller 102 through a suitable interface.

Software, hardware or firmware, or a combination thereof, may be configured to read this serial number, and subsequently taking appropriate action including device specific initializations, setting of parameters and recording and reporting data based on that serial number.

In different embodiments, this concept can be extended to provide the ability to identify any or all assemblies connected to the microprocessor platform through use of multiple digital identifier components, with each one associated with an individual assembly to be identified.

1.14 Modem Communications

In some applications it may be desirable to establish communications between the invention and an external device through a telephony connection. This invention provides a means for communication and control through telephony by providing an integrated modem capability. In essence, a modem translates digital signals into acoustic tones that can be transmitted over a standard telephone connection. These tones are decoded at the other end of the connection by another modem, thereby establishing a communications link across a telephone connection. In addition, various additional signals may be employed to monitor and control the state of the telephone connection.

These modem functions can be provided by a single integrated circuit, such as the TDK Semiconductor 73M2901CL device. In various embodiments of this invention, a device such as this may be included, along with appropriate software to support operation of and communications through the device. A standard telephone connector would also be provided for direct interface to a telephone line.

This feature provides the ability for either the invention or an external host to place a telephone call to the other and establish a communications link. Once established, many functions such as control or monitoring of the x-ray module status, or data upload to or download from the x-ray module are possible. In addition, the ability to reprogram the x-ray module by uploading new software into memory is possible. This has significant benefit for updating or upgrading the software as necessary. Downloading a copy of the x-ray module software would also be possible. This could be useful for fault diagnosis. Another use of a modem link would be to permit selective enabling or disabling of functionality in the x-ray module. This could be employed for field diagnostic purposes, or as an element of an equipment leasing or purchase agreement, whereby features would be enabled based on payment, for example.

1.15 Controller Capabilities

A description of some of the architectures and algorithms that may be implemented in embodiments of the invention, for example, by the controller 102 and/or the microcontroller 410 is provided as follows. Other architectures and algorithms are possible and are intended to fall within the scope of the invention. Various embodiments may utilize all or some of the modes, functions and features described below.

1.15.1 Operational Modes

Several operational modes of the invention are possible, some of which can be identified as follows.

1.15.1.1 Power on Self Test (POST)

Upon application of power to the controller 102, the controller 102 may be configured to perform a power on self-test. Several parameters may be verified for functionality, including: system memory, the data acquisition and output control subsystem 412 and any safety and interlock features provided. Key signals may be monitored to verify that they are within tolerance.

1.15.1.2 Ready Mode

In a READY mode, the system 300 may be fully powered and operational but not producing or preparing to produce x-rays. In this mode, digital communications may be established through the digital communications interface 318 allowing the device to respond to external commands. This may be the top level mode of the system, from which all other modes of operation can be entered. When in this state the 'READY' indicator may illuminate in embodiments provided with such an indicator.

1.15.1.3 Arm Mode

In an "Arm" mode, the controller 102 may be configured to prepare the hardware for making x-rays. The controller 102 may verify that any safety interlock signals provided in certain embodiments are satisfied, and also may verify that appropriate input parameters and control voltages are within acceptable tolerances. If all conditions are satisfied, the controller 102 may be configured to enable the resonant converter power supply 618 and set the high voltage output to the desired value. The beam current may be disabled and the filament in the x-ray tube 306 may not be powered. When in this state the 'ARMED' indicator may be configured to illuminate in embodiments provided with such an indicator.

In some embodiments of the controller 102, certain controller functions such as certain types of digital communications may be disabled in the Arm mode.

1.15.1.4 X-Rays On Mode

In "X-RAYS On" mode, power to the filament may be enabled and beam current production may be initiated, resulting in x-ray output from the tube 306. In this mode, the controller 102 may participate in any of: the active control of the high voltage, the beam current and, for specific embodiments fitted with an appropriate x-ray detector, x-ray output. In each case, the controller 102 may read the appropriate feedback signal and may calculate an error value based on the difference between the feedback signal and the respective set point value (KV_SET, BC_SET or XRAY_SET, depending on the specific embodiment). This error then may be used to calculate updated values for KV_CTRL 622 and BC_CTRL 518. These values then may be applied to the resonant converter 608 to adjust the high voltage power supply 620, and to the filament drive power supply 516 to adjust the beam current. In embodiments where the high voltage, beam current or x-ray output is to be modulated, the controller 102 may update the KV_SET, BC_SET and XRAY_SET set point parameters as required to achieve the desired modulation.

While in this mode, filament power consumption may be monitored continuously by the controller 102. Filament power consumption provides an indication of the health of the filament and the remaining lifetime. Filament impedance, and therefore filament power consumption is expected to increase as the filament ages. Power consumption may be stored and compared against prior values to identify and assess any changes in filament impedance.

Input power consumption also may be continuously monitored by the controller 102. Comparing filament power consumption to input power consumption provides a measure of x-ray tube output efficiency, particularly in embodiments where an x-ray detector is used to directly monitor x-ray emissions. In cases where an x-ray tube 306 is inefficient in producing x-rays, a higher input power than normally required may be necessary to produce adequate emission, which may help to identify a faulty, or failing x-ray tube 306.

X-ray production may continue until either a hardware input signal or digital input command is received to terminate x-ray production or if any interlock signals that may have been provided in certain embodiments are no longer satisfied. For safety purposes, a timer may be configured to cause x-ray production to cease if a termination signal is not otherwise received within the maximum allotted time. When in this state the 'X-RAYS ON' indicator may illuminate in embodiments provided with such an indicator.

In some embodiments of the controller 102, certain controller functions such as certain types of digital communications may be disabled in this mode.

1.15.1.5 Service Mode

This mode may provide additional functionality that assists manufacturing and service personnel in performing calibration, test, fault diagnosis and other service functions. Service mode is a mode of operation which permits full access to all the microcontroller capabilities and access to special functions and capabilities not provided to the end user. It is a mode that in certain embodiments may require specific permissions to access certain services. For example, a password or other code not generally available to the end user may be provided.

Examples of functions that may be provided in this mode include:

Self-test: To test the functionality of the system across the range of operating parameters and determine if all relevant parameters are within acceptable tolerance limits and to indicate a fault otherwise.

Calibration: To calibrate high voltage, beam current and x-ray output to input control commands across the full range of system operating parameters and environments.

Control Loop Tuning: To automatically tune the high voltage, filament drive and x-ray output control loops for desired behavior including transient response and steady-state operating characteristics.

Burn-In Testing: To enable the system to operate autonomously over an extended period of time to evaluate and verify system reliability.

Diagnostic Testing: To provide extensive diagnostic test capability for x-ray tube 306 and system electronics to assist in identification and localization of identified faults. Special test routines may permit direct access to system memory, and include special diagnostic functions, not generally performed during self-test, that may more readily identify specific faults.

1.15.1.5.1 Calibration

In addition, or as an alternative, to the POST tests described above, calibration of x-ray output may be performed. X-ray output may be initiated at a specific accelerating voltage and output flux. Actual values may be measured using appropriate test equipment. Differences between the set values and the actual may be utilized to develop a calibration curve to be stored in system memory. Correction factors based on this calibration curve may be determined and applied to the KV_SET, BC_SET and XRAY_SET control values as appropriate to adjust the actual x-ray output to more closely match expected values. This testing may be performed across a range of x-ray outputs and operating conditions, including temperature, to fully characterize behavior.

Figure 22:
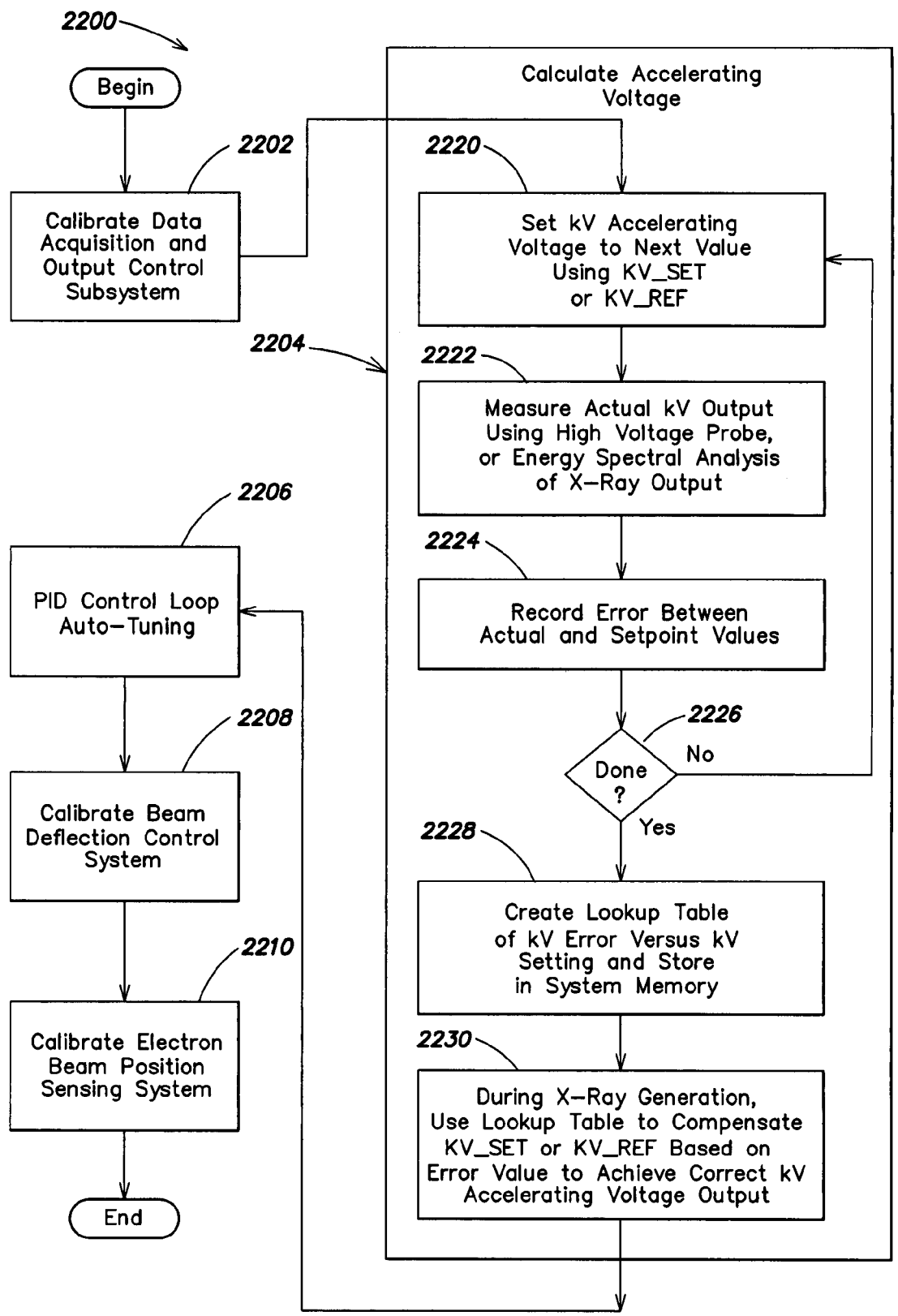
FIG. 22 is a flow chart illustrating an example of a method of implementing calibration.

Calibration may be implemented as shown in FIG. 22. FIG. 22 is a flow chart that illustrates an example of a method 2200 for implementing calibration, for example, as part of step 722. Steps 2202, 2206, 2208 and 2210 may be implemented as described in §1.3.4, 1.16.3, 1.10.1 and 2.11, respectively. In step 2202, the data acquisition and output control subsystem is calibrated. In step 2204, the accelerating voltage is calibrated. Step 2204 includes substeps 2220-2230. In substep 2220, the kV accelerating voltage is set to a next value using KV_SET or KV_REF. In substep 2222, an actual kV output voltage is measured using a high voltage probe, or energy spectral analysis of the x-ray output. In substep 2224, an error between actual kV output and the kV setpoint values is determined. The process continues in substep 2226 by returning to substep 2220, or proceeds to substep 2228. In substep 2228, a lookup table of kV error versus kV setting is created, and the table is stored in the system memory. During x-ray generation, the lookup table is used in substep 2230 to compensate KV_SET or KV_REF values based on an error value to achieve a correct kV accelerating voltage output. In step 2206, PID control loop auto-tuning is performed. In step 2208, the beam deflection control system is calibrated. In step 2210, the electron beam position sensing system is calibrated.

1.15.1.5.2 Burn-In Testing

Autonomous burn-in testing of x-ray modules may be performed by the controller 102. Burn-in testing may include running the x-ray tube 306 and associated electronics under a variety of operating conditions and output levels for a period of time. The specific test profiles may be stored in system memory, or, depending on specific embodiments, test parameters may be uploaded through the digital communications interface 318 to permit more flexible control of the testing process.

Testing may be initiated in any of a variety of ways, for example, through a digital input command, or through a hardware trigger or control bit. The controller 102 may monitor system behavior during testing and record pertinent data for subsequent output and review.

Figure 23:
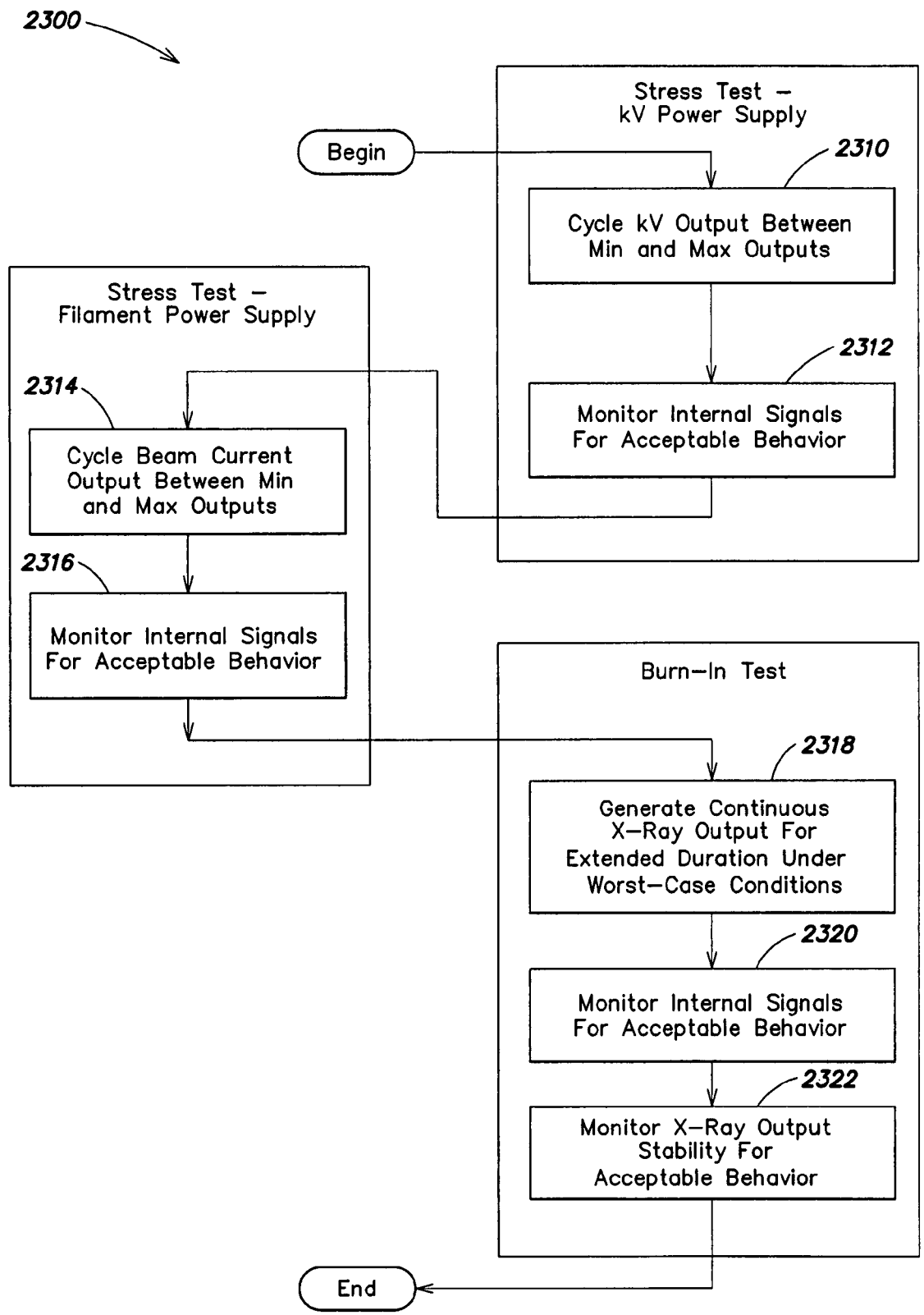
FIG. 23 is a flow chart illustrating an example of a method of implementing burn-in testing.

Burn-in testing may be implemented as shown in FIG. 23. FIG. 23 is a flow chart that illustrates an example of a method 2300 for implementing burn-in testing, for example, as part of step 726. In steps 2310 and 2312, high voltage power supply is stress tested. In step 2310, the high voltage output is cycled between minimum and maximum outputs. In step 2312, internal signals in the high voltage power supply are monitored for acceptable behavior. In steps 2314 and 2316, the filament power supply is stress tested. In step 2314 the beam current output is cycled between minimum and maximum outputs. In step 2316, internal signals in the filament power supply are monitored for acceptable behavior. Burn-in test includes steps 2318-2322. In step 2318, a continuous x-ray output is generated for an extended duration under worst-case conditions. In step 2320, internal signals are monitored for acceptable behavior. In step 2322, x-ray output stability is monitored for acceptable behavior.

1.15.1.6 Datalogging Mode

Datalogging mode may be provided to permit continuous reporting of system operational parameters through the digital communications interface 318. In this manner, real-time data acquisition of such parameters as high voltage power supply 620 output, beam current, filament power consumption, input power consumption can be provided. Data logging may be enabled and disabled during any of the other operational modes of the system.

1.15.2 Control Modes

In some embodiments, the control loops in this invention may have the ability to set the x-ray output to a fixed value that is maintained with a high degree of accuracy and precision. In some embodiments, it may be desirable to vary the x-ray output as a function of time, or in response to external signals or events. Thus, different control modes may be used to enable this ability to change the x-ray output.

1.15.2.1 Manual Control

Manual control mode is an operational mode whereby the controller 102 may respond continually to external input commands (e.g. KV_SET, BC_SET, XRAY_SET) for setting x-ray output parameters such as high voltage and beam current. In this mode, external hardware may be operative to, and responsible for, adjusting the x-ray output as desired. This adjusting may require the external hardware (or in some cases possibly the end-user) to intervene each time the x-ray output is adjusted. Such intervention may require a certain level of capability in this external hardware but may provide maximum flexibility for setting the x-ray output.

1.15.2.2 Semi-Autonomous Control

In semi-autonomous control mode, the controller 102 may contain preprogrammed values or discrete settings for setting the x-ray output. In this mode, external hardware simply may request that the high voltage be turned on, without the need to specify a particular output voltage value. The controller 102 may turn on the high voltage and set the output to a predetermined value. A series of predefined values for the input control signals also may be established, such that a request to set the high voltage to a particular value (e.g., three) may be sufficient for the controller 102 to turn on the high voltage and set the appropriate value.

An advantage of this type of control is that it may simplify the interface to external hardware. Rather than requiring a communications interface, the external hardware could simply assert or deassert digital data lines through the use of switches or other means to signal the controller 102 as to how to set and maintain the x-ray output. These preset values may be fixed by the controller 102, or capability may be provided to permit these values to be pre-determined and stored in memory, which would provide a high degree of flexibility in setting the x-ray output.

1.15.2.3 Autonomous Control

In autonomous control, the controller 102 may contain pre-programmed x-ray output profiles which are executed autonomously upon receipt of an appropriate input trigger. These profiles may be fixed or may be programmable by a user, thereby providing greater flexibility and utility. For example, the ability for the end user to define these profiles may be provided. Thus, automatic control may be tailored for each specific application.

An example of automatic control will now be described. The x-ray tube accelerating high voltage may be made to sweep over a preprogrammed voltage range at a predefined rate in response to an appropriate input command being received by the controller 102. Additional communications input from the external hardware may not be required during the sweep process. After completing the sweep, the high voltage may be shut off or held at some final endpoint value.

An advantage of this control mode is that it may permit an extremely simple communications interface. A single digital control line (such as could be developed from a trigger switch or other contact closure) may be sufficient to initiate x-ray production and control x-ray output to a predefined profile. In another embodiment, the trigger event may be based on time, such that at a predetermined time, or at predetermined intervals, an x-ray output profile may be initiated.

This control approach may have use in applications whereby repetitive tasks are performed on an ongoing basis, such as in manufacturing or automated inspection. In such applications, a single input command may be sufficient to instruct the controller 102 to set the x-ray tube output and have it follow a profile.

1.15.3 Fault Monitoring and Diagnostics

The controller 102 may be configured to provide the capability for a variety of fault monitoring and diagnostics. In the various operational modes of the invention, fault monitoring may be performed on an appropriate basis. This fault monitoring may involve monitoring signals provided as inputs to the controller 102, either as analog signals through the data acquisition sub-system 414 or as digital signals through various inputs to the controller 102.

These inputs may be compared to acceptable values and tolerance ranges based in part on the mode of operation of the system. Inputs falling outside of acceptable ranges may cause a fault indication to be raised. The controller 102 may be configured to take appropriate action based on the nature of the fault.

In the event that a fault condition is detected, diagnostic information may be provided through the digital communications interface 318 to assist in determining the nature and cause of the fault.

1.15.4 Control Loop Architecture Configurability

The controller 102 provides the means by which to easily implement various control loop architectures for optimum control of the x-ray tube accelerating high voltage and beam current. In some embodiments, a PID control architecture may be implemented, whereby each control loop (high voltage and beam current, respectively) operates independently and controls the output based on a weighted combination of the proportional, integral and derivatives of the error between the actual and desired output.

Other architectures are possible. For example, non-linear behavior may be incorporated, perhaps to compensate for the non-linear characteristics of the x-ray tube filament, and/or feedback inputs from multiple sources may be utilized. A cross-coupled control architecture between the high voltage and beam current may be used. In cases where the beam current and high voltage are not truly independent parameters, the control loop for the high voltage may require knowledge of the beam current output. Other variants of cross-coupled control based on feedback signals from external detector systems or other sources may also be implemented in various embodiments.

Other control architectures, in which feedback from external detectors may be used in place of, or in conjunction with, high voltage and beam current feedback are also possible.

1.16 Controller Algorithms

1.16.1 X-Ray Output Control

The controller 102 may be configured to enable and provide closed-loop control of the x-ray output. A set point value may be input through an analog or digital communications interface 318 for each parameter that establishes some characteristic of the x-ray output emission that is to be placed under closed-loop control. Such set point values may include any of: set point values for power supply high voltage (to establish electron beam accelerating voltage and resultant maximum x-ray output energy), beam current, x-ray output flux and electron beam position on the target. The controller 102 may be configured to enable and provide monitoring of the actual values (feedback values) of these parameters. For each parameter under closed-loop control, algorithms may determine the error between the set point and actual values of the parameter. This error may be used to generate a corresponding control signal, which may be used to adjust the appropriate circuit elements in order to set and maintain the controlled parameter at the specific set point value. A PID control loop architecture may be employed in this embodiment. Other linear, non-linear or multivariate control methodologies may be implemented in other embodiments. Multivariate control refers to an approach whereby the control output signal is a function of more than one feedback input signal and/or other input signals that are combined in some defined manner to produce the control output signal.

The controller 102 may be configured to respond to commands that set a variety of x-ray output control modes and x-ray output versus time profiles. Two examples of these control modes are as follows:

Constant Output
  Mode: The controller 102 maintains the x-ray output at a constant value
  Modulation: The controller 102 modulates the x-ray output in a specified manner. Examples include pulsing the accelerating voltage and/or beam current on and off in a prescribed manner, and/or varying the accelerating voltage or current up or down as some function of time. Another example would be in embodiments provided with electron beam deflection capability, whereby modulation of the electron beam position on the target to affect x-ray output in some manner.

1.16.1.1 X-Ray Output Modulation

In some applications, it may be desirable to modulate some aspect of the x-ray output emission, such as spectrum or output flux. One or more of the variables which influence the x-ray emission from the x-ray tube 306, including accelerating voltage, beam current and beam position on target, may be used, singly or in combination as a means of modulating the x-ray emission.

Modulation may take the form of temporal modulation, whereby some aspect of the x-ray output is made to vary as a function of time. Other forms of modulation are also possible, whereby some aspect of the x-ray emission or variable used to establish the emission is made to vary in response to one or more other variables. An example of this is to modulate the beam current as a function of accelerating voltage. Thus, a change in accelerating voltage may be made to induce a change in beam current, and therefore x-ray emission output, without any specific or predetermined temporal dependence. In this generalized definition of modulation, any arbitrary combination of input variables can be used as a means to modulate some aspect of the x-ray output. A possible application of this approach would be to maintain a constant electron beam power (defined as the product of the accelerating voltage and the beam current), as the accelerating voltage is changed.

1.16.1.1.1 Modulation Approaches

Modulation of the x-ray emission may be implemented in different manners in various embodiments of this invention, depending on where the modulation signal originates and the degree of configurability provided. Any or all of the following modulation approaches may be implemented in various combinations and sequences in various embodiments of the invention.

1.16.1.1.1.1 External Modulation

In this approach, modulation may be achieved by allowing an external host to directly vary the input control parameters that affect x-ray emission during the emission. Adjustment of these control parameters may be performed through the analog or digital interface provided for purposes of communication with an external host. This adjustment enables the external host to dynamically and directly alter aspects of the x-ray output during x-ray emission in an arbitrary and continuous manner, giving the external host complete control over the x-ray emission.

In one example, the BC_SET parameter, an input control parameter used to establish the x-ray tube beam current and the corresponding x-ray output intensity, may be continuously adjusted by the external host as a means to modulate the output intensity. In this manner, the external host may establish sinusoidal or pulse modulation, or any arbitrary modulation of the x-ray output desired.

1.16.1.1.1.2 Preprogrammed Modulation

In this modulation approach, the controller 102 may be configured with predefined modulation profiles that an external host can modify by sending configuration parameters through a communications interface. Profiles such as sinusoidal, ramp, saw tooth and pulse, and various combinations and sequences of these profiles, may be used. In addition, capability for the external host to upload into the x-ray module custom modulation profiles also may be provided. Thus, a completely general approach to defining the modulation profile to be utilized may be implemented. A benefit to this approach is that the external host does not need to continuously participate in the modulation. Instead, it establishes a modulation configuration through use of the configuration parameters, and allows the controller 102 to perform the modulation during x-ray emission.

In various embodiments, configuration parameters used to tailor each modulation profile may be changed dynamically during x-ray emission, providing a high degree of flexibility. For example, a frequency sweep may be performed on a sinusoidal modulation by having the external host transmit a series of frequency values to the sinusoidal modulation algorithm in the microcontroller code during the modulation process, to dynamically alter the modulation. Alternatively, in other embodiments, these frequency values may be transmitted to the controller 102 and stored in memory in advance. After the modulation process has begun, these frequency values may be read from memory at a specified rate, or in general in response to the occurrence of specific events such as from a timing signal, to continuously adjust the modulation frequency based on these stored frequency values.

For example, the controller 102 may contain a pre-defined sinusoidal modulation algorithm, which may be utilized to produce a sinusoidally varying output such as beam current. The external host may send modulation configuration parameters such as frequency, amplitude and offset to configure this sinusoidal modulation profile as desired. No other involvement by the external host may be necessary after the modulation profile has been configured. The controller 102 may be configured modulate the beam current, which may in turn result in a corresponding modulation of the x-ray output intensity, based on this modulation profile.

1.16.1.1.1.3 Local Modulation

In the local modulation approach, the controller 102 may contain particular modulation profiles that can be applied to specific parameters, similar to the above description of Preprogrammed Modulation. However, in this approach, configuration of specific modulation parameters, such as frequency and amplitude, may be performed without reliance on a communications interface between the x-ray module and an external host.

Instead, modulation parameters may be set through use of digital and analog input signals, either created within the x-ray module, or provided as input signals from the external host. The controller 102 may read these signals and configure the modulation profile accordingly. An advantage of this approach is that it preserves the configurability and flexibility of the other approaches without need for the complexities associated with establishing a communications interface. Thus, modulation profiles can be selected or enabled through use of digital bits, switches or other simple signals read through an appropriate interface.

As an example, a digital input pin, which the controller 102 can read, may be provided as input to the x-ray module to enable and disable sinusoidal modulation of the x-ray tube beam current. When the logic level of this bit is set to logic low, modulation may be disabled and the beam current may assume a constant value during x-ray emission. When the logic level is set high, sinusoidal modulation of the beam current may be enabled. For simplicity, all other parameters which define the modulation, such as frequency and amplitude may be fixed, and otherwise not adjustable by an external host (local modulation). Alternatively, any or all of these parameters may be made controllable through use of other analog or digital input signals.

1.16.1.1.2 Modulation Synchronization

In certain applications such as synchronous detection, it may be useful for an external system to be able to synchronize to the modulation being impressed on the x-ray output emission. In some embodiments, a modulation synchronization signal 322 may be provided, for example, as shown as an output from the D/A converter 413 in FIG. 4. This signal may assume several forms, and may follow, in general, the modulation waveform being impressed on the x-ray output, or otherwise may convey real-time information about the modulation to an external system. In cases where multiple modulation is being employed, such as independent modulation of accelerating voltage and beam current, independent modulation synchronization signal 322s may be provided for each, or alternatively a single modulation synchronization signal 322 comprised of some combination of independent modulation profiles may be generated.

In some embodiments, a sinusoidal modulation may be impressed on the beam current. The modulation synchronization signal 322 also may be a sinusoidal waveform with a frequency and phase synchronized to the beam current modulation. The amplitude of this synchronization signal may be fixed or it may vary in some relationship to the amplitude of the actual beam current modulation. In another embodiment, the synchronization waveform may be a square wave output such that the edge transitions occur at some defined point of the modulation waveform, for example at points of maximum amplitude or maximum slope.

In FIG. 4, the modulation synchronization signal 322 may be an output from a D/A converter 413. In other embodiments, the signal may be generated directly by electronic circuits without software intervention. In other additional embodiments, the synchronization signal may be provided directly as digital values sent through a communications interface.

1.16.2 Error Compensation

Errors in x-ray accelerating voltage, beam current and x-ray output may result from tolerance variations in components as well as from temperature, impressed voltage, input voltage, and other effects. The controller 102 may be configured to compensate for these errors by applying correction factors to the x-ray tube control signals during operation. This compensation may occur initially prior to x-ray turn on, or continuously during x-ray production. In some embodiments, correction factor information may be stored in non-volatile memory in the x-ray module. Alternatives, such as uploading correction factors through a communications link from an external system, are also possible.

Any of a variety of techniques may be employed to determine appropriate correction factors. Manufacturer's component specifications provide information on component temperature and voltage coefficients. Additionally, calibration tests of the x-ray module and/or key components such as the high-voltage sense resistor 616 may provide information about the behavior of components and of the module due to temperature, impressed voltage on or current through the component, input voltage, and other factors.

Sensors, such at temperature sensors or x-ray detectors may be utilized to monitor key variables to permit selection of appropriate correction factors.

1.16.2.1 Temperature Compensation

Certain control components may have a specified temperature coefficient such that their values change in a predictable manner with variations in temperature. The high voltage sense high voltage sense resistor 616 in the high voltage power supply 620 is one example of such a component, where the divide ratio, an important factor in achieving an accurate high voltage output, may vary with temperature. This variation can lead to errors in the x-ray output energy. The controller 102 may have the capability to read a temperature sensor located on or in proximity to each of these sensitive components and introduce compensation into the control circuits to correct for temperature-induced error.

Alternatively, temperature correction factors may be determined during calibration, based on measurement of x-ray tube parameters and comparison to desired values. This correction data may be stored subsequently in system memory. These correction factors may be applied to the x-ray output control circuitry either initially or continuously during x-ray production to adjust the control signals to compensate for the error.

1.16.2.2 Accelerating Voltage Compensation

The accuracy of the accelerating voltage output from the high voltage power supply 620 may depend in part on components with values that have a voltage coefficient. That is, the component value may change with variations in impressed voltage across the component. This variation in component value can lead to errors in x-ray output. For example, for the high voltage sense resistor 616 that may be used to directly sense x-ray accelerating high voltage, the resistive divide ratio may vary with impressed voltage across the high voltage sense resistor 616 It should be appreciated that the high voltage sense resistor 616 acts as a resistive voltage divider to the voltage output by kV multiplier chain 612. The controller 102 may be configured to determine a correction factor based on the specified voltage coefficient and the requested voltage to be impressed across the component, which may then be applied to the appropriate control circuits to correct for this error.

Alternatively, correction factors for voltage coefficients may be determined during calibration, based on measured errors between desired and actual accelerating voltage output. This correction data subsequently may be stored in system memory. These correction factors may be applied to the x-ray output control circuitry either initially or continuously during x-ray production to adjust the control signals as necessary to compensate for the error.

1.16.3 PID Control Loop Auto-Tuning

To achieve high accuracy in the x-ray output, closed loop control may be used. In some embodiments, any of closed loop control of the high voltage, the beam current, and the x-ray output may be used individually or in some combination. In hardware-based implementations, the transient behavior of the control loop, stability, step response time and other factors may depend on the specific type of control loop configuration and the component values selected.

After being selected, the control loop may behave in a fixed and predictable manner, but may be inflexible and/or incapable of accommodating wide variation in performance of the x-ray tube characteristics without changes to component values. Selecting component values that work across the range of x-ray tube performance may result in a control loop configuration that compromises performance when mated to a specific tube.

Accordingly, in some embodiments, the control loop is implemented by the controller 102. Software values (e.g., variables) may replace fixed component values for determining the behavior and transient response of the control loop. In this manner, the controller 102 may tune the control loop parameters to the characteristics of an individual x-ray tube 306, permitting optimum performance to be achieved on an individual basis.

To tune each control loop, a technique for establishing the proportional, integral and derivative scale factors, $K_p$, $K_i$ and $K_d$, respectively, for each loop may be used. For example, a technique of automatically tuning the control loop to set these parameters, based on the output response of the x-ray tube as indicated by the behavior of the KV_FDBK 354, BC_FDBK 364 and XRAY_FDBK 366 signals may be employed.

One approach to establishing these parameters employs a standard Ziegler-Nichols approach to PID control loop tuning. This is a well known method widely published in the literature. In essence, with $K_i$ and $K_d$ set to zero, the proportional gain factor, $K_p$, is increased until the control loop begins to oscillate. Based on this value of gain, the final values of all three factors may be determined by applying appropriate Ziegler-Nichols scale factors to this gain value. Other well-known methods of tuning PID control loops based on transient response to step inputs may also be implemented in specific embodiments.

Due to the non-linear behavior of the x-ray tube filament, in some embodiments a set of PID scale factors may be established at multiple beam current and high voltage settings to achieve optimal performance at each setting. In this case, control loop tuning may be performed at each setting and the three PID scale factors corresponding to that setting may be determined. Interpolation or other means may be used in some embodiments to estimate PID scale factor coefficients at intermediate beam current and high voltage settings.

Figure 24:
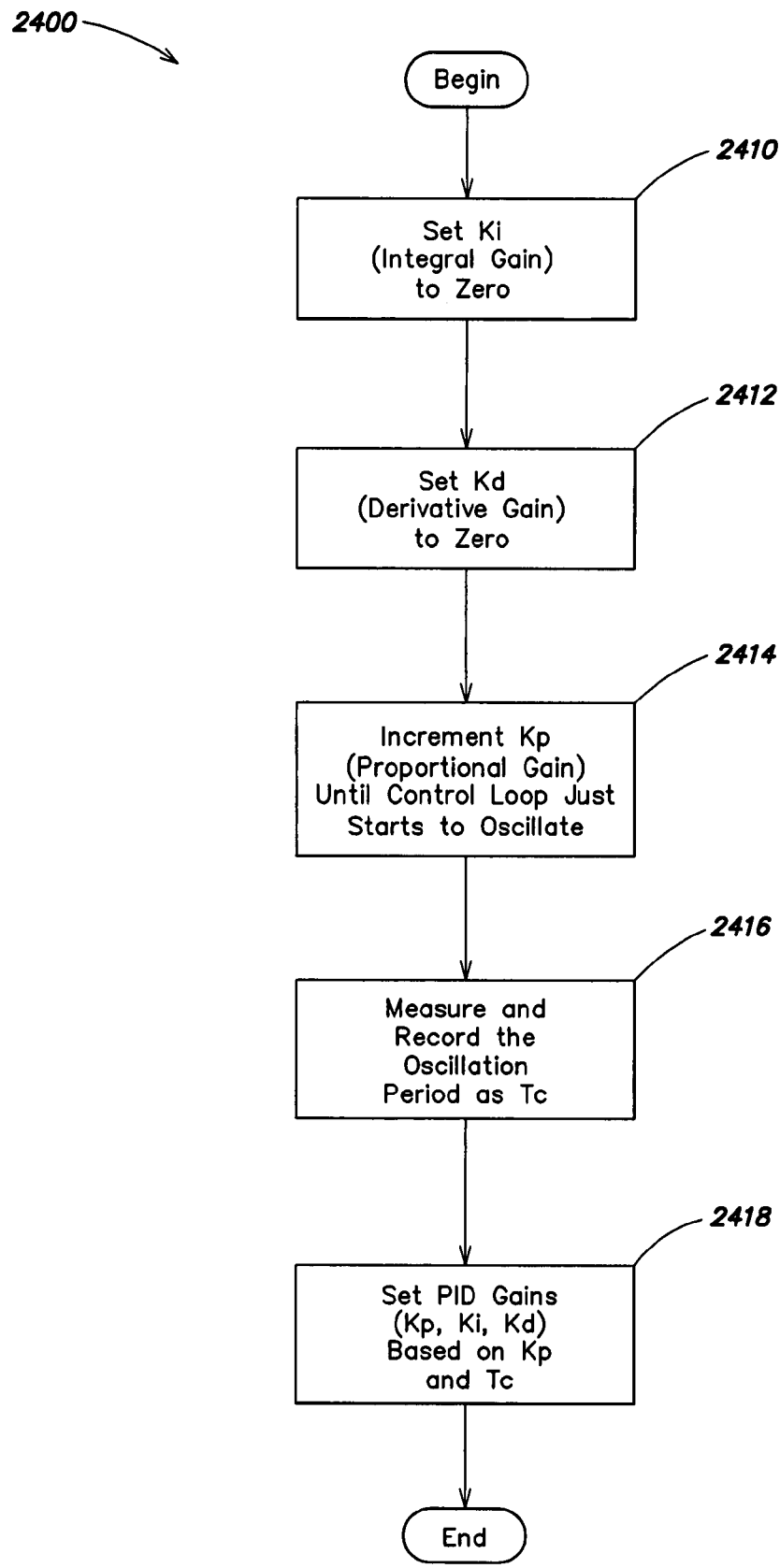
FIG. 24 is a flow chart illustrating an example of a method of implementing PID control loop auto-tuning.

PID control loop auto-tuning may be performed as illustrated in FIG. 24. FIG. 24 is a flow chart that illustrates an example of a method 2400 for implementing PID control loop auto-tuning, for example, as part of step 724. In step 2410, the value of Ki (integral gain) set to zero. In step 2412, the value of Kd (derivative gain) is set to zero. In step 2414, the value of Kp (proportional gain) is incremented until the control loop just starts to oscillate. In step 2416, the oscillation period is measured and recorded as a value Tc. In step 2418, the PID gains (Kp, Ki, Kd) are set based on the values of Kp and Tc.

1.16.4 Fault Detection, Handling and History Log

The controller 102 may be configured to detect faults, and may be configured to take appropriate action should a fault occur. Examples of fault conditions include:

X-ray tube: Arcing, unstable beam current, high leakage current, low x-ray output, improper filament impedance HV power supply 620: Unstable accelerating voltage Microcontroller System: Memory faults, communications faults In response to detecting a fault, the controller 102 may be configured to take appropriate action. Such action may include any of: shutting off x-ray output (if active), setting a fault flag and updating the fault history log stored in non-volatile memory.

Figure 25:
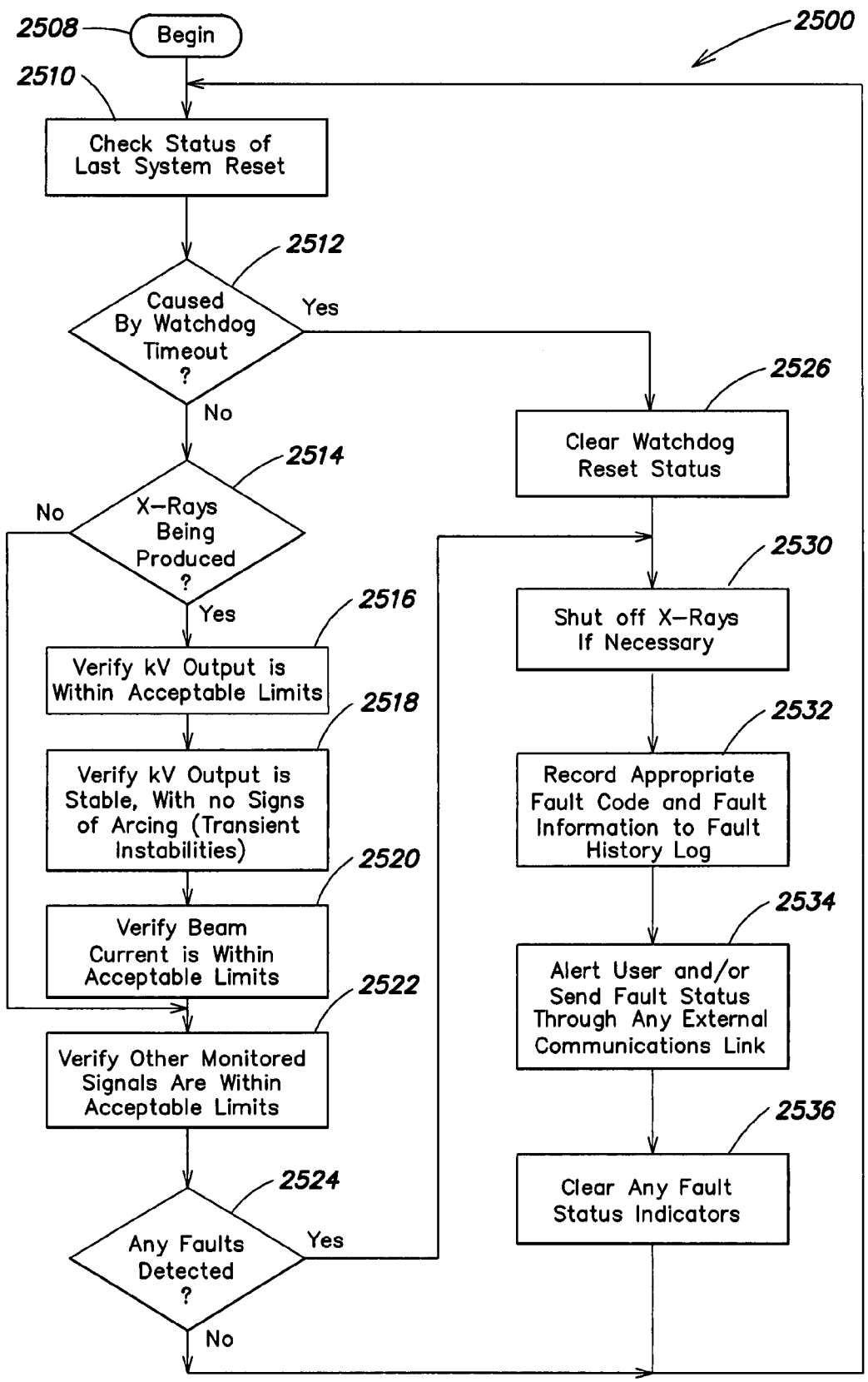
FIG. 25 is a flow chart illustrating an example of a method of implementing fault detection.

Fault detection may be implemented as shown in FIG. 25. FIG. 25 is a flow chart that illustrates an example of a method 2500 for implementing fault detection, for example, as part of step 730. Fault detection begins in step 2508. In step 2510, status of the last system reset is checked. If the last system reset was not caused by watchdog timeout, as determined in step 2512, a determination is made in step 2514 as to whether x-rays are being produced. If x-rays are being produced, the high voltage output is verified in step 2516 to be within acceptable limits. In step 2518 the high voltage output is verified to be stable, with no signs of arcing (transient instabilities). In step 2520, the beam current is verified to be within acceptable limits. If x-rays are not being produced, step 2514 proceeds to step 2522. In step 2522, other monitored signals are verified to be within acceptable limits. If faults have been detected in step 2524, the process proceeds to step 2530. If the last system reset was determined in step 2512 to be caused by a watchdog timeout, the watchdog reset status is cleared in step 2526 and the process proceeds to step 2530. In step 2530, the x-rays are shut off if necessary. In step 2532, the appropriate fault code and fault information are recorded in a fault history log. In step 2534, the user is alerted and/or a fault status is sent through an external communications link. In step 2536, any fault status indicators are cleared. The process returns from step 2524 or step 2536 to step 2510.

1.16.5 Self-Test

Figure 26:
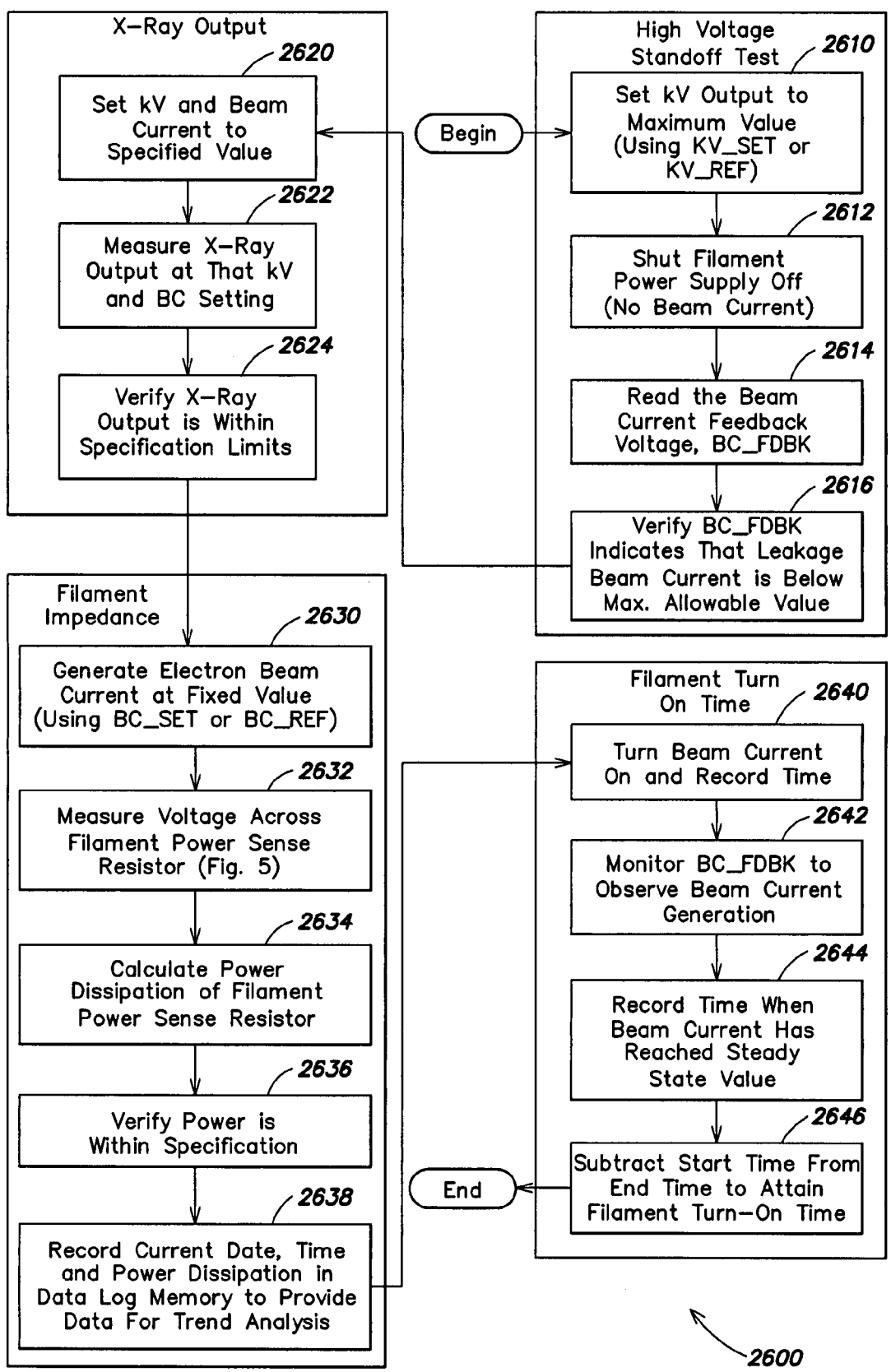
FIG. 26 is a flow chart illustrating an example of a method of implementing self-testing.

The controller 102 may be configured to perform self-test functions to verify proper operation of the x-ray module and module sub-assemblies. Such self-test functions may include any of:

ROM Program Verification
Memory Checks
Control Components Tests
X-ray Module Level Tests Self-Testing, including diagnostics, may be implemented as shown in FIG. 26. FIG. 26 is a flow chart that illustrates an example of a method 2600 for implementing self-testing, including diagnostics, for example, as part of step 728. A high voltage standoff test includes steps 2610-2616. In step 2610, the high voltage output is set to maximum value using KV_SET or KV_REF. In step 2612, the filament power supply is shut off. In step 2614, the beam current feedback voltage BC_FDBK is read. In step 2616, the beam current feedback voltage is verified as indicating that leakage beam current is below a maximum allowable value. An X-ray output test is performed in steps 2620-2624. In step 2620, the high voltage and beam current are set to specified values. In step 2622, the x-ray output is measured at the specified high voltage and beam current settings. In step 2624, the x-ray output is verified to be within specification limits. A filament impedance test is performed in steps 2630-2638. In step 2630, an electron beam current is generated at a fixed value using BC_SET or BC_REF. In step 2632, the voltage across filament power sense resistor 508 is measured. In step 2634, the power dissipation of filament power sense resistor 508 is calculated. In step 2636, the power dissipation is verified to be within specification. In step 2638, the current date, time and power dissipation are recorded in a data log memory to provide data for trend analysis. A filament turn-on time test is performed in steps 2640-2646. In step 2640, the beam current is turned on and the time is recorded. In step 2642, the beam current feedback voltage BC_FDBK is monitored to observe beam current generation. In step 2644, the time when the beam current has reached a steady state value is recorded. In step 2646, the start time is subtracted from the end time to obtain filament turn-on time.

1.16.6 X-Ray Tube Performance Checks

The controller 102 may be configured to perform checks of the x-ray tube 306. Such performance checks may include any of the performance checks listed in the following eight sub-sections.

1.16.6.1 High Voltage Standoff

Measure the tube leakage current (BC_FDBK 364) when high voltage is applied across the tube 306 while the tube filament is below emission temperature.

1.16.6.2 X-Ray Output

In embodiments which are interfaced to an x-ray detector for output monitoring and/or control, verify that the x-ray output is within acceptable limits for specified values of accelerating voltage and beam current.

1.16.6.3 Filament Impedance and Lifetime

Measure filament voltage and current to determine filament impedance and verify that impedance is within acceptable limits. Filament impedance can be used as a quality control indicator to verify an in-specification filament, and can also be used as a predictor of filament lifetime.

1.16.6.4 Filament Turn-On Time

Measure the time from turn on of the filament driver power supply 516 to the time that beam current is produced. Verify that the turn-on time is within acceptable limits.

1.16.7 Data Logging and Output

The controller 102 may be configured to store and output data, including data described in the following two sub-sections:

1.16.7.1 Usage History Log

Record data on usage, including total powered on time, total time that filament has been operating, high voltage and beam current settings, and other parameters pertinent to identifying how the device is being utilized. Data can be used for warranty and service purposes, and other applications as necessary.

1.16.7.2 Fault History Log

Record each detected fault along with a time stamp. This information can be used to help assess failure modes of the device, or typical failure modes of the design.

Figure 27:
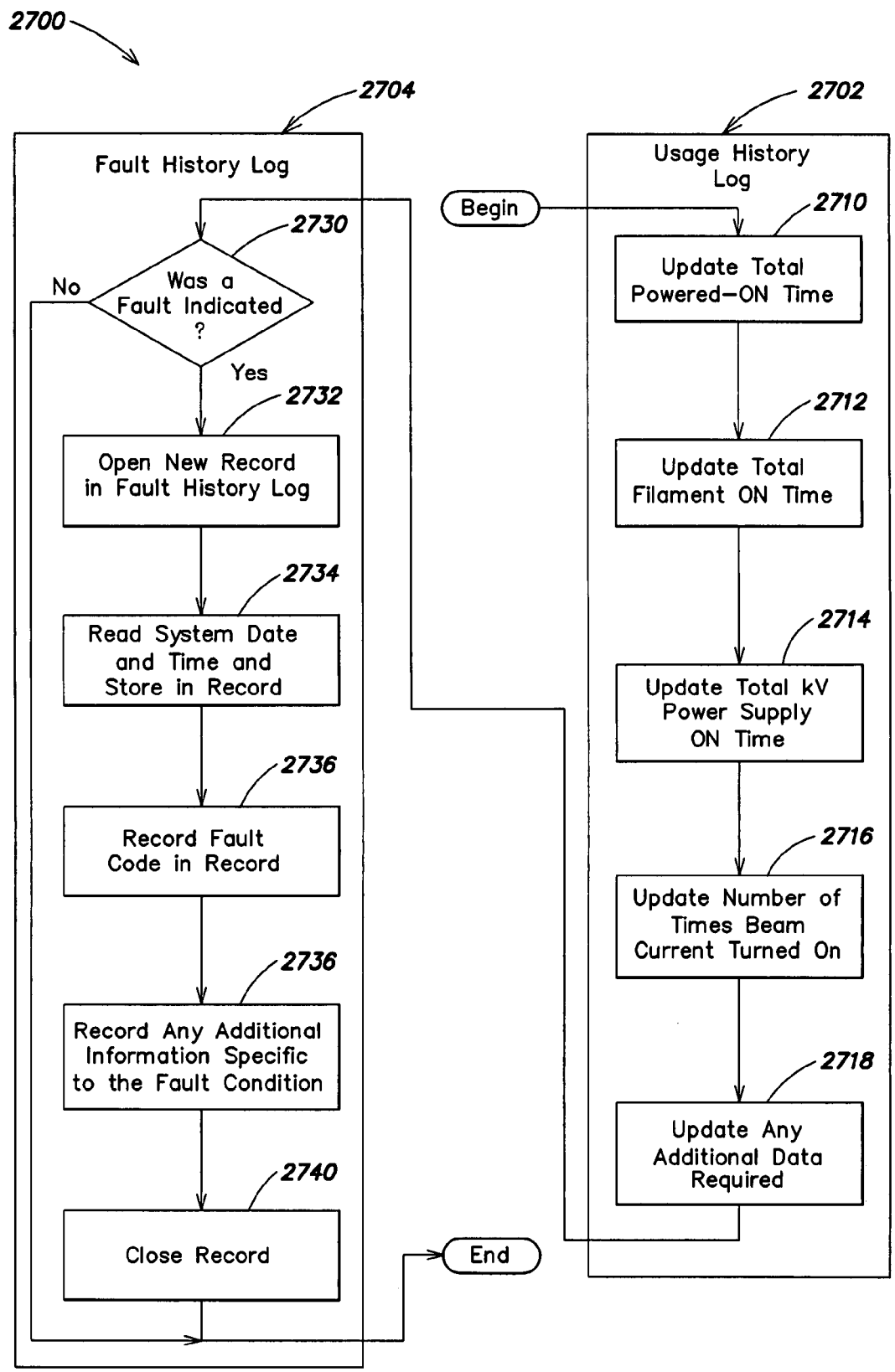
FIG. 27 is a flow chart illustrating an example of a method of implementing data logging and output.

Data logging and output may be implemented as shown in FIG. 27. FIG. 27 is a flow chart that illustrates an example of a method 2700 for implementing data logging and output, for example, as part of step 734. Blocks 2702 and 2704 may be implemented as described in Sections 2.16.7.1 and 2.16.7.2, respectively. A usage history log is maintained in block 2702, which includes steps 2710-2718. In step 2710, a total powered-on time is updated. In step 2712, a total filament on time is updated. In step 2714, a total high voltage power supply on time is updated. In step 2716, a number of times the beam current was turned on is updated. In step 2718, any additional required data is updated. A fault history log is maintained in block 2704, which includes step 2730-2740. If a fault is indicated in step 2730, a new record is opened in the fault history log in step 2732. In step 2734, the system date and time are read and stored in the record. In step 2736, a fault code is stored in the record. In step 2738, any additional information specific to the fault condition is recorded. In step 2740, the record is closed.

1.16.8 Communications

The controller 102 may be configured to provide digital communications capability, enabling the controller 102 to communicate with an external host.

A set of commands may be implemented by the controller 102, such that when a command is received through the communications port, the controller 102 recognizes it as a task to be performed and initiates the commanded action. In this manner, an external host can communicate with the system for purposes of remote control, monitoring or diagnostics. These tasks may include any of: setting and monitoring the accelerating voltage, beam current and x-ray output, initiating self-tests and acquiring test results and outputting selected data on an as-requested or continuous basis (data-logging mode) and reprogramming the controller 102.

1.16.8.1 Modem Communications

In various embodiments of this invention, a modem 320 may be included which permits communications between the x-ray module and an external host through telephony. Drivers, capable of communicating with and controlling the modem hardware may be included as part of the controller 102.

The controller 102 may be configured to provide the requisite functions for any of: placing or receiving a telephone call, monitoring the status of the connection, and taking appropriate action as necessary, for example in the case of a dropped connection (hang up).

Features and functions as discussed previously, such as x-ray module control and monitoring, data upload and download, and the ability to reprogram the x-ray module through upload of new software also may be provided through this communications link.

1.16.8.2 Communications Interfaces

It should be appreciated that a variety of different communication interfaces may be implemented in various embodiments of this invention, for example, as part of controller 102. These communications interfaces may include any of: a Universal Serial Bus (USB) interface, Bluetooth® Wireless interface, I²C-Bus interface, CAN (Controller Area Network) interface, and RS-232 serial communications interface, other types of communications interfaces, or any combination thereof.

Figure 28:
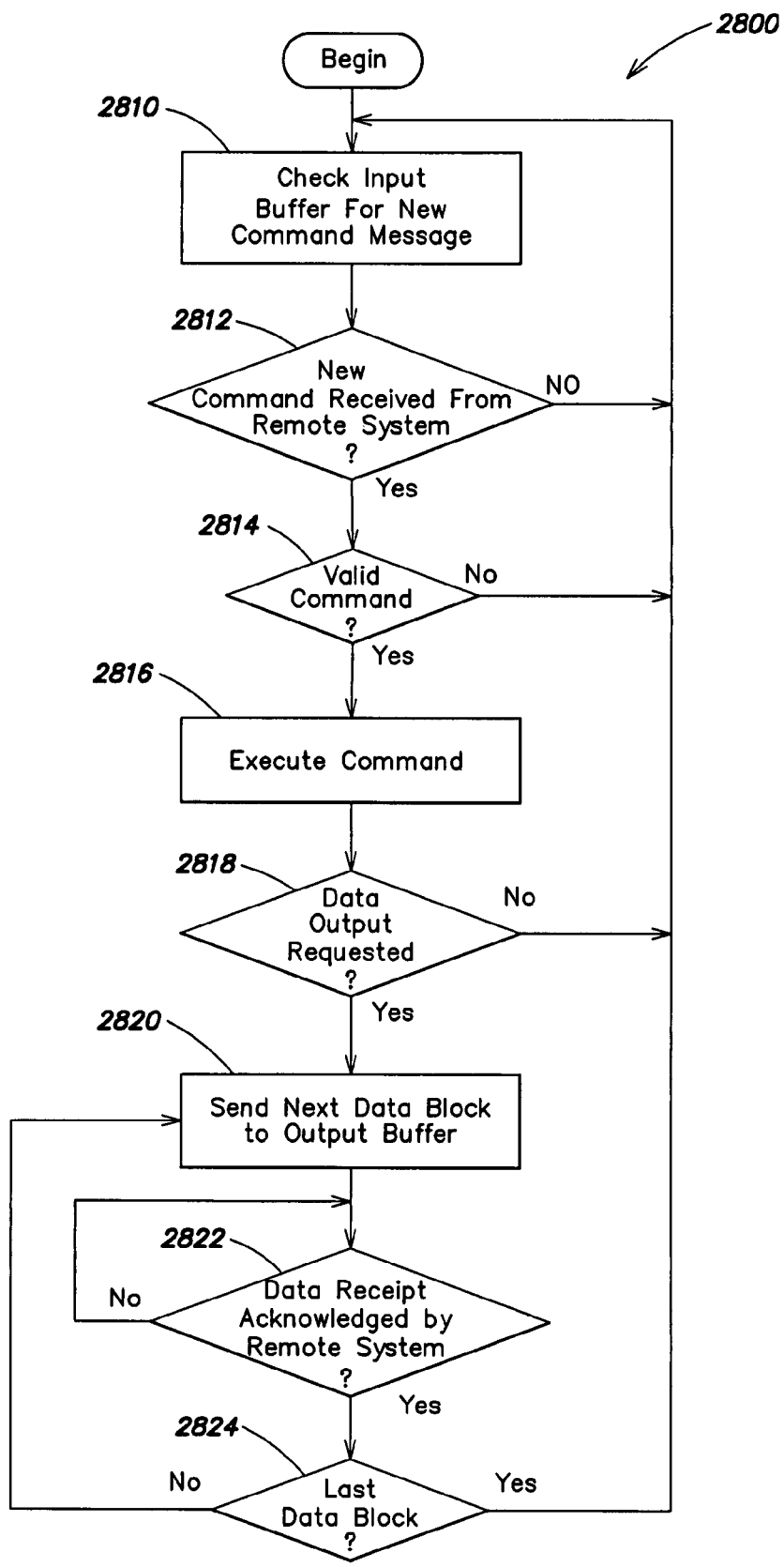
FIG. 28 is a block diagram illustrating an example of a method of implementing communications.

Communications may be implemented as illustrated in FIG. 28. FIG. 28 is a flow chart that illustrates an example of a method 2800 for implementing communications, for example, as part of step 732. In step 2810, the input buffer is checked for a new command message. In step 2812, a determination is made as to whether a new command was received from a remote system. If a new command is received, a test for a valid command is made in step 2814. A valid command is executed in step 2816. If data output is requested, as determined in step 2818, the next data block is sent to the output buffer in step 2820. Step 2822 determines if data receipt has been acknowledged by the remote system. If data receipt has been acknowledged, a determination is made in step 2824 if the last data block has been transmitted. If the last data block has not been transmitted, the process returns to step 2820. If the last data block has been transmitted, as determined in step 2824, the process returns to step 2810. If a new command was not received from the remote system in step 2812, if an invalid command was received as determined in step 2814 or if data output was not requested as determined in step 2818, the process returns to step 2810.

1.17 Safety Features

Several safety features may be included in the invention. Implementation of these safety features in many cases may be simplified by the use of a controller (e.g., controller 102) and associated software and/or firmware. Any or all of these features may be included in various embodiments of the invention.

1.17.1 Reset

The system 300 may be designed to ensure that after coming out of a reset state, all registers, control lines, etc. are initialized to a state that prevents x-ray production.

1.17.2 Power-On Self Test

A power-on self test (POST) may function to verify proper operation of the system prior to initiation of x-ray production. Any detected failures during this test may be used to prohibit x-ray production until the failure mechanism has been corrected.

Figure 29:
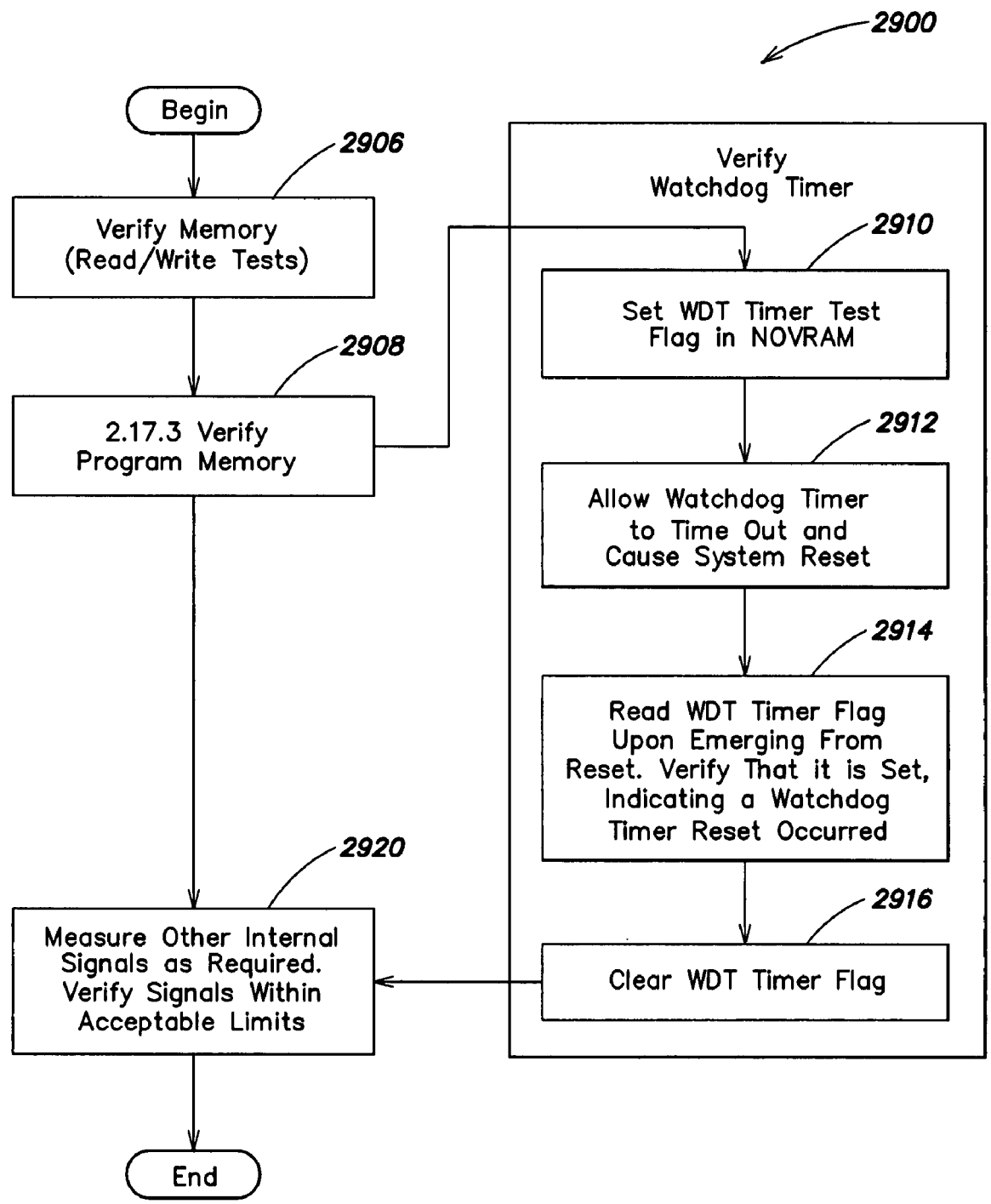
FIG. 29 is a block diagram illustrating an example of a method of implementing a power-on self test.

A power-on self test may be implemented as shown in FIG. 29. FIG. 29 is a flow chart that illustrates an example of a method 2900 for implementing a power-on self test, for example, as part of step 720. In step 2906, memory is verified by read/write tests. In step 2908, program memory is verified. A verification of the watchdog timer includes steps 2910-2916. In step 2910, a watchdog timer test flag is set. In step 2912, the watchdog timer is allowed to time out and cause a system reset. In step 2914, the watchdog timer flag is read upon emerging from reset. If the watchdog timer flag is set, a watchdog timer reset has occurred. In step 2916, the watchdog timer flag is cleared. In step 2920, other internal signals are measured as required and are verified to be within acceptable limits.

1.17.3 Program Memory Integrity Test

To verify integrity of the controller 102, a checksum approach may be used whereby the checksum of memory is calculated and compared to a stored value. Any difference may be identified as a memory fault condition which may be used to prevent x-ray production.

1.17.4 Watchdog Timer

To verify that the controller 102 is functioning properly to ensure that x-ray production is terminated in the event of a software crash, a watchdog timer may be utilized. The system watchdog counts down from a preset value toward zero, at which time a system reset may be generated. If the controller 102 is functioning properly, it may continually initialize the watchdog to the preset value avoiding the generation of the reset.

1.17.5 X-Ray Status Indicators

Illuminated status indicator outputs may be provided that indicate the status of x-ray production. In various embodiments, these outputs may include indicators 316 for each of the x-ray production modes indicated previously (READY, ARMED, XRAYS-ON)

1.17.6 X-Rays On Time Delay

In certain embodiments, and as may be required by external product safety regulations, initiation of x-ray production may require a time delay to be introduced between activation of the signal to request x-ray production and onset of the actual x-ray output. Accordingly, the system 300 may be configured to provide such time delay.

1.17.7 External Hardware Interlock

In certain embodiments, a hardware interface to an external interlock input signal may be included. Such interlock may enable use of an external switch, signal or similar input to prevent x-ray production from being initiated until the interlock input signal is asserted, and/or to terminate x-ray production if the interlock input signal is deasserted.

1.17.8 X-Ray Output Limits

Maximum upper limits may be established on high voltage, beam current and x-ray output to prevent x-ray output from exceeding safe upper limits. If an x-ray detector is utilized, maximum limits on measured parameters, such as absorbed dose may be implemented depending on the embodiment as adapted to a specific application.

These limits may be implemented in hardware, software, firmware or any suitable combination thereof, such that the parameter being limited may be prevented from exceeding that value. Any attempt to exceed the value may be detected by the controller 102 and a fault indicated, which may be utilized to terminate x-ray production.

1.17.9 X-Ray Production Timeout

An upper limit on the duration of X-ray production may be provided to prevent indefinite generation of x-rays.

1.17.10 Power Fail Monitor

A power fail monitor device also may be included in the system high-voltage sense. This device senses an impending loss of input power, causing an interrupt which permits the controller 102 to save important data and shut down in an orderly way.

1.17.11 Password Protection

Password protection may be employed to prevent unauthorized access to or operation of the x-ray module. Passwords may take the form of a digital signature communicated to the controller 102 via a communications input. Multi-level passwords may be utilized to permit or prevent access to different areas of the data, or different control modes. For example, a service password might permit complete access to all functional aspects of the module and access to all data, and could also allow access to special test and diagnostics modes intended only for factory use. User-level passwords might prohibit access to certain data or other functionality reserved for factory use, but may otherwise permit operation of the device.

User-level passwords may be used to prohibit unauthorized operation of the x-ray module including initiation of x-ray production, access to data, or removal of data.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A control system for an X-ray source, the X-ray source including an X-ray tube, comprising:

a high voltage power supply including a resonant converter-based power supply having a resonant converter that drives a transformer for operating the X-ray source, the high voltage power supply further including a temperature-sensitive high voltage resistive divider to sense the high voltage of the high voltage power supply and to produce a voltage feedback signal;

a temperature sensor to sense the temperature of the high voltage resistive divider and to provide a temperature feedback signal;

a sensor interface operative to receive the voltage feedback signal and the temperature feedback signal; and a programmable controller operative, in the response to the voltage feedback signal and the temperature feedback signal, to compensate for temperature effects and to generate a control signal for controlling the resonant converter-based power supply to maintain the input voltage to the X-ray tube over a temperature range.

* * * * *